(12) United States Patent
Kreek et al.

(10) Patent No.: US 7,071,315 B2
(45) Date of Patent: Jul. 4, 2006

(54) ALLELES OF THE HUMAN MU OPIOID RECEPTOR, DIAGNOSTIC METHODS USING SAID ALLELES, AND METHODS OF TREATMENT BASED THEREON

(75) Inventors: Mary Jeanne Kreek, New York, NY (US); Karl Steven LaForge, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/883,839

(22) Filed: Jun. 18, 2001

(65) Prior Publication Data

US 2004/0209250 A1    Oct. 21, 2004

Related U.S. Application Data

(60) Provisional application No. 60/212,225, filed on Jun. 16, 2000.

(51) Int. Cl.
*C07H 21/04* (2006.01)
(52) U.S. Cl. ................. 536/23.1; 435/69.1; 435/320.1; 435/252.3; 435/455; 435/471; 435/325; 536/23.5
(58) Field of Classification Search ................. None
See application file for complete search history.

(56) References Cited

U.S. PATENT DOCUMENTS 5,474,796 A * 12/1995 Brennan .................... 427/2.13

FOREIGN PATENT DOCUMENTS

WO    WO 95/07983    3/1995

OTHER PUBLICATIONS

Bond et al. (PNAS USA, vol. 95, p. 9608-9613, Aug. 1998).*
Ahern (The Scientist, vol. 9, No. 15, p. 20, Jul. 1995; computer print out provided, page numbers refer to the print out).*
Berrettini, Wade H. et al. Addiction Biology vol. 2: pp. 303-308 (1997).
Wang, J.B., et al. GenBank Accession No. L25119, Aug. 8, 1994.
Bare, L.A., et al. GenBank Accession No. U12569, Apr. 12, 1995.

* cited by examiner

*Primary Examiner*—Juliet C Switzer
(74) *Attorney, Agent, or Firm*—Klauber & Jackson

(57) ABSTRACT

Provided herein are variant alleles of a gene encoding a mu opioid receptor, along with cloning vectors for replicating such variant alleles, expressing vectors for expressing the variant alleles to produce variant mu opioid receptors, and antibodies to such variant receptors. Also disclosed are binding characteristics of such variant receptors regarding binding to opioid ligands, and the using of such binding characteristics to diagnose a subjects susceptibility to pain, susceptibility to an addictive disease, selecting an appropriate pain reliever along with a therapeutically effective amount of the reliever to administer to a subject suffering from pain. In addition, diagnostic methods for diagnosing a disease or disorder such as infertility, constipation, diarrhea, decreased immune response relative to a standard, and decreased ability to withstand stress relative to a standard, along with commercial kits for diagnosing such diseases or disorders. Furthermore, the invention is also directed to identification of targeted prevention methods, early therapeutic intervention, and improved treatment of opioid addiction, infertility, constipation, diarrhea, impaired immune responsiveness, and stress.

11 Claims, 20 Drawing Sheets

600-1-266        FIGURE 1A

SEQ ID NO:1

```
   1 ggaattccgg ctataggcag aggagaatgt cagatgctca gctcggtccc ctccgcctga
  61 cgctcctctc tgtctcagcc aggactggtt tctgtaagaa acagcaggag ctgtggcagc
 121 ggcgaaagga agcggctgag gcgcttggaa cccgaaaagt ctcggtgctc ctggctacct
 181 cgcacagcgg tgcccgcccg gccgtcagta ccatggacag cagcgctgcc cccacgaacg
 241 ccagcaattg cactgatgcc ttggcgtact caagttgctc cccagcaccc agcccggtt
 301 cctgggtcaa cttgtcccac ttagatggca acctgtccga cccatgcggt ccgaaccgca
 361 ccaacctggg cgggagagac agcctgtgcc ctccgaccgg cagtccctcc atgatcacgg
 421 ccatcacgat catggccctc tactccatcg tgtgcgtggt ggggctcttc ggaaacttcc
 481 tggtcatgta tgtgattgtc agatacacca agatgaagac tgccaccaac atctacattt
 541 tcaaccttgc tctggcagat gccttagcca ccagtaccct gcccttccag agtgtgaatt
 601 acctaatggg aacatggcca tttggaacca tcctttgcaa gatagtgatc tccatagatt
 661 actataacat gttcaccagc atattcaccc tctgcaccat gagtgttgat cgatacattg
 721 cagtctgcca ccctgtcaag gccttagatt tccgtactcc ccgaaatgcc aaaattatca
 781 atgtctgcaa ctggatcctc tcttcagcca ttggtcttcc tgtaatgttc atggctacaa
 841 caaaatacag gcaaggttcc atagattgta cactaacatt ctctcatcca acctggtact
 901 gggaaaacct cgtgaagatc tgtgtttttca tcttcgcctt cattatgcca gtgctcatca
 961 ttaccgtgtg ctatggactg atgatcttgc gcctcaagag tgtccgcatg ctctctggct
1021 ccaaagaaaa ggacaggaat cttcgaagga tcaccaggat ggtgctggtg gtggtggctg
1081 tgttcatcgt ctgctggact cccattcaca tttacgtcat cattaaagcc ttggttacaa
1141 tcccagaaac tacgttccag actgtttctt ggcacttctg cattgctcta ggttacacaa
1201 acagctgcct caacccagtc ctttatgcat ttctggatga aaacttcaaa cgatgcttca
1261 gagagttctg tatcccaacc tcttccaaca ttgagcaaca aaactccact cgaattcgtc
1321 agaacactag agaccacccc tccacggcca atacagtgga tagaactaat catcagctag
1381 aaaatctgga agcagaaact gtccgttgc cctaacaggg tctcatgcca ttccgacctt
1441 caccaagctt agaagccacc atgtatgtgg aagcaggttg cttcaagaat gtgtaggagg
1501 ctctaattct ctaggaaagt gcctacttt aggtcatcca acctctttcc tctctggcca
1561 ctctgctctg cacattagag ggacagccaa aagtaagtgg agcatttgga aggaaaggaa
1621 tataccacac cgaggagtcc agtttgtgca agacacccag tggaaccaaa acccatcgtg
1681 gtatgtgaat tgaagtcatc ataaaaggtg acccttctgt ctgtaagatt ttattttcaa
1741 gcaaatattt atgacctcaa caaagaagaa ccatcttttg ttaagttcac cgtagtaaca
1801 cataaagtaa atgctacctc tgatcaaagc accttgaatg gaaggtccga gtctttttag
1861 tgttttgca agggaatgaa tccattattc tatttagac ttttaacttc aacttaaaat
1921 tagcatctgg ctaaggcatc attttcacct ccatttcttg gttttgtatt gtttaaaaaa
1981 aataacatct ctttcatcta gctccataat tgcaagggaa gagattagca tgaaaggtaa
2041 tctgaaacac agtcatgtgt canctgtaga aaggttgatt ctcatgcact ncaaatactt
2101 ccaaagagtc atcatggggg attttcatt cttaggcttt cagtggtttg ttcctggaat
2161 tc
```

600-1-266
SEQ ID NO:2

FIGURE 1B

| | | | | | | | | | | | | | | |
|---|---|---|---|---|---|---|---|---|---|---|---|---|---|---|
| Met | Asp | Ser | Ser | Ala | Ala | Pro | Thr | Asn | Ala | Ser | Asn | Cys | Thr | Asp | Ala |
| 1 | | | | 5 | | | | | 10 | | | | | 15 | |
| Leu | Ala | Tyr | Ser | Ser | Cys | Ser | Pro | Ala | Pro | Ser | Pro | Gly | Ser | Trp | Val |
| | | | 20 | | | | | 25 | | | | | 30 | | |
| Asn | Leu | Ser | His | Leu | Asp | Gly | Asn | Leu | Ser | Asp | Pro | Cys | Gly | Pro | Asn |
| | | 35 | | | | | 40 | | | | | 45 | | | |
| Arg | Thr | Asn | Leu | Gly | Gly | Arg | Asp | Ser | Leu | Cys | Pro | Pro | Thr | Gly | Ser |
| | 50 | | | | | 55 | | | | | 60 | | | | |
| Pro | Ser | Met | Ile | Thr | Ala | Ile | Thr | Ile | Met | Ala | Leu | Tyr | Ser | Ile | Val |
| 65 | | | | | 70 | | | | | 75 | | | | | 80 |
| Cys | Val | Val | Gly | Leu | Phe | Gly | Asn | Phe | Leu | Val | Met | Tyr | Val | Ile | Val |
| | | | | 85 | | | | | 90 | | | | | 95 | |
| Arg | Tyr | Thr | Lys | Met | Lys | Thr | Ala | Thr | Asn | Ile | Tyr | Ile | Phe | Asn | Leu |
| | | | 100 | | | | | 105 | | | | | 110 | | |
| Ala | Leu | Ala | Asp | Ala | Leu | Ala | Thr | Ser | Thr | Leu | Pro | Phe | Gln | Ser | Val |
| | | 115 | | | | | 120 | | | | | 125 | | | |
| Asn | Tyr | Leu | Met | Gly | Thr | Trp | Pro | Phe | Gly | Thr | Ile | Leu | Cys | Lys | Ile |
| | 130 | | | | | 135 | | | | | 140 | | | | |
| Val | Ile | Ser | Ile | Asp | Tyr | Tyr | Asn | Met | Phe | Thr | Ser | Ile | Phe | Thr | Leu |
| 145 | | | | | 150 | | | | | 155 | | | | | 160 |
| Cys | Thr | Met | Ser | Val | Asp | Arg | Tyr | Ile | Ala | Val | Cys | His | Pro | Val | Lys |
| | | | | 165 | | | | | 170 | | | | | 175 | |
| Ala | Leu | Asp | Phe | Arg | Thr | Pro | Arg | Asn | Ala | Lys | Ile | Ile | Asn | Val | Cys |
| | | | 180 | | | | | 185 | | | | | 190 | | |
| Asn | Trp | Ile | Leu | Ser | Ser | Ala | Ile | Gly | Leu | Pro | Val | Met | Phe | Met | Ala |
| | | 195 | | | | | 200 | | | | | 205 | | | |
| Thr | Thr | Lys | Tyr | Arg | Gln | Gly | Ser | Ile | Asp | Cys | Thr | Leu | Thr | Phe | Ser |
| | 210 | | | | | 215 | | | | | 220 | | | | |
| His | Pro | Thr | Trp | Tyr | Trp | Glu | Asn | Leu | Val | Lys | Ile | Cys | Val | Phe | Ile |
| 225 | | | | | 230 | | | | | 235 | | | | | 240 |
| Phe | Ala | Phe | Ile | Met | Pro | Val | Leu | Ile | Ile | Thr | Val | Cys | Tyr | Gly | Leu |
| | | | | 245 | | | | | 250 | | | | | 255 | |
| Met | Ile | Leu | Arg | Leu | Lys | Ser | Val | Arg | Met | Leu | Ser | Gly | Ser | Lys | Glu |
| | | | 260 | | | | | 265 | | | | | 270 | | |
| Lys | Asp | Arg | Asn | Leu | Arg | Arg | Ile | Thr | Arg | Met | Val | Leu | Val | Val | Val |
| | | 275 | | | | | 280 | | | | | 285 | | | |
| Ala | Val | Phe | Ile | Val | Cys | Trp | Thr | Pro | Ile | His | Ile | Tyr | Val | Ile | Ile |
| | 290 | | | | | 295 | | | | | 300 | | | | |
| Lys | Ala | Leu | Val | Thr | Ile | Pro | Glu | Thr | Thr | Phe | Gln | Thr | Val | Ser | Trp |
| 305 | | | | | 310 | | | | | 315 | | | | | 320 |
| His | Phe | Cys | Ile | Ala | Leu | Gly | Tyr | Thr | Asn | Ser | Cys | Leu | Asn | Pro | Val |
| | | | | 325 | | | | | 330 | | | | | 335 | |
| Leu | Tyr | Ala | Phe | Leu | Asp | Glu | Asn | Phe | Lys | Arg | Cys | Phe | Arg | Glu | Phe |
| | | | 340 | | | | | 345 | | | | | 350 | | |
| Cys | Ile | Pro | Thr | Ser | Ser | Asn | Ile | Glu | Gln | Gln | Asn | Ser | Thr | Arg | Ile |
| | | 355 | | | | | 360 | | | | | 365 | | | |
| Arg | Gln | Asn | Thr | Arg | Asp | His | Pro | Ser | Thr | Ala | Asn | Thr | Val | Asp | Arg |
| | 370 | | | | | 375 | | | | | 380 | | | | |
| Thr | Asn | His | Gln | Leu | Glu | Asn | Leu | Glu | Ala | Glu | Thr | Ala | Pro | Leu | Pro |
| 385 | | | | | 390 | | | | | 395 | | | | | 400 |

600-1-266    FIGURE 2A

SEQ ID NO:3

```
   1 ggaattccgg ctataggcag aggagaatgt cagatgctca gctcggtccc ctccgcctga
  61 cgctcctctc tgtctcagcc aggactggtt tctgtaagaa acagcaggag ctgtggcagc
 121 ggcgaaagga agcggctgag gcgcttggaa cccgaaaagt ctcggtgctc ctggctacct
 181 cgcacagcgg tgcccgcccg gccgtcagta ccatggacag cagcgctgcc cccacgaacg
 241 ccagcaattg cactgatgcc ttggcgtact caagttgcgc cccagcaccc agcccggtt
 301 cctgggtcaa cttgtcccac ttagatggca acctgtccga cccatgcggt ccgaaccgca
 361 ccaacctggg cgggagagac agcctgtgcc ctccgaccgg cagtccctcc atgatcacgg
 421 ccatcacgat catggccctc tactccatcg tgtgcgtggt ggggctcttc ggaaacttcc
 481 tggtcatgta tgtgattgtc agatacacca agatgaagac tgccaccaac atctacattt
 541 tcaaccttgc tctggcagat gccttagcca ccagtaccct gcccttccag agtgtgaatt
 601 acctaatggg aacatggcca tttggaacca tcctttgcaa gatagtgatc tccatagatt
 661 actataacat gttcaccagc atattcaccc tctgccacat gagtgttgat cgatacattg
 721 cagtctgcca ccctgtcaag gccttagatt tccgtactcc ccgaaatgcc aaaattatca
 781 atgtctgcaa ctggatcctc tcttcagcca ttggtcttcc tgtaatgttc atggctacaa
 841 caaaatacag gcaaggttcc atagattgta cactaacatt ctctcatcca acctggtact
 901 gggaaaacct cgtgaagatc tgtgttttca tcttcgcctt cattatgcca gtgctcatca
 961 ttaccgtgtg ctatggactg atgatcttgc gcctcaagag tgtccgcatg ctctctggct
1021 ccaaagaaaa ggacaggaat cttcgaagga tcaccaggat ggtgctggtg gtggtggctg
1081 tgttcatcgt ctgctggact cccattcaca tttacgtcat cattaaagcc ttggttacaa
1141 tcccagaaac tacgttccag actgtttctt ggcacttctg cattgctcta ggttacacaa
1201 acagctgcct caacccagtc ctttatgcat ttctggatga aaacttcaaa cgatgcttca
1261 gagagttctg tatcccaacc tcttccaaca ttgagcaaca aaactccact cgaattcgtc
1321 agaacactag agaccacccc tccacggcca atacagtgga tagaactaat catcagctag
1381 aaaatctgga agcagaaact gctccgttgc cctaacaggg tctcatgcca ttccgacctt
1441 caccaagctt agaagccacc atgtatgtgg aagcaggttg cttcaagaat gtgtaggagg
1501 ctctaattct ctaggaaagt gcctactttt aggtcatcca acctctttcc tctctggcca
1561 ctctgctctg cacattagag ggacagccaa aagtaagtgg agcatttgga aggaaaggaa
1621 tataccacac cgaggagtcc agtttgtgca agacacccag tggaaccaaa acccatcgtg
1681 gtatgtgaat tgaagtcatc ataaaggtg acccttctgt ctgtaagatt ttatttttcaa
1741 gcaaatattt atgacctcaa caaagaagaa ccatctttg ttaagttcac cgtagtaaca
1801 cataaagtaa atgctacctc tgatcaaagc accttgaatg gaaggtccga gtctttttag
1861 tgttttgca agggaatgaa tccattattc tattttagac ttttaacttc aacttaaaat
1921 tagcatctgg ctaaggcatc attttcacct ccatttcttg gttttgtatt gtttaaaaaa
1981 aataacatct ctttcatcta gctccataat tgcaagggaa gagattagca tgaaaggtaa
2041 tctgaaacac agtcatgtgt canctgtaga aaggttgatt ctcatgcact ncaaatactt
2101 ccaaagagtc atcatggggg attttcatt cttaggcttt cagtggtttg ttcctggaat
2161 tc
```

600-1-266             FIGURE 2B
SEQ ID NO:4

Met Asp Ser Ser Ala Ala Pro Thr Asn Ala Ser Asn Cys Thr Asp Ala
 1               5                  10                  15
Leu Ala Tyr Ser Ser Cys Pro Pro Ala Pro Ser Pro Gly Ser Trp Val
             20              25                  30
Asn Leu Ser His Leu Asp Gly Asn Leu Ser Asp Pro Cys Gly Pro Asn
             35                  40              45
Arg Thr Asn Leu Gly Gly Arg Asp Ser Leu Cys Pro Pro Thr Gly Ser
     50                  55                  60
Pro Ser Met Ile Thr Ala Ile Thr Ile Met Ala Leu Tyr Ser Ile Val
 65              70                  75                      80
Cys Val Val Gly Leu Phe Gly Asn Phe Leu Val Met Tyr Val Ile Val
                 85                  90                  95
Arg Tyr Thr Lys Met Lys Thr Ala Thr Asn Ile Tyr Ile Phe Asn Leu
             100                 105                 110
Ala Leu Ala Asp Ala Leu Ala Thr Ser Thr Leu Pro Phe Gln Ser Val
             115                 120                 125
Asn Tyr Leu Met Gly Thr Trp Pro Phe Gly Thr Ile Leu Cys Lys Ile
     130                 135                 140
Val Ile Ser Ile Asp Tyr Tyr Asn Met Phe Thr Ser Ile Phe Thr Leu
145                 150                 155                 160
Cys Thr Met Ser Val Asp Arg Tyr Ile Ala Val Cys His Pro Val Lys
                 165                 170                 175
Ala Leu Asp Phe Arg Thr Pro Arg Asn Ala Lys Ile Ile Asn Val Cys
             180                 185                 190
Asn Trp Ile Leu Ser Ser Ala Ile Gly Leu Pro Val Met Phe Met Ala
     195                 200                 205
Thr Thr Lys Tyr Arg Gln Gly Ser Ile Asp Cys Thr Leu Thr Phe Ser
210                 215                 220
His Pro Thr Trp Tyr Trp Glu Asn Leu Val Lys Ile Cys Val Phe Ile
225                 230                 235                 240
Phe Ala Phe Ile Met Pro Val Leu Ile Ile Thr Val Cys Tyr Gly Leu
                 245                 250                 255
Met Ile Leu Arg Leu Lys Ser Val Arg Met Leu Ser Gly Ser Lys Glu
             260                 265                 270
Lys Asp Arg Asn Leu Arg Arg Ile Thr Arg Met Val Leu Val Val Val
         275                 280                 285
Ala Val Phe Ile Val Cys Trp Thr Pro Ile His Ile Tyr Val Ile Ile
290                 295                 300
Lys Ala Leu Val Thr Ile Pro Glu Thr Thr Phe Gln Thr Val Ser Trp
305                 310                 315                 320
His Phe Cys Ile Ala Leu Gly Tyr Thr Asn Ser Cys Leu Asn Pro Val
             325                 330                 335
Leu Tyr Ala Phe Leu Asp Glu Asn Phe Lys Arg Cys Phe Arg Glu Phe
             340                 345                 350
Cys Ile Pro Thr Ser Ser Asn Ile Glu Gln Gln Asn Ser Thr Arg Ile
             355                 360                 365
Arg Gln Asn Thr Arg Asp His Pro Ser Thr Ala Asn Thr Val Asp Arg
     370                 375                 380
Thr Asn His Gln Leu Glu Asn Leu Glu Ala Glu Thr Ala Pro Leu Pro
385                 390                 395                 400

600-1-266     FIGURE 3A

SEQ ID NO:5
```
   1 ggaattccgg ctataggcag aggagaatgt cagatgctca gctcggtccc ctccgcctga
  61 cgctcctctc tgtctcagcc aggactggtt tctgtaagaa acagcaggag ctgtggcagc
 121 ggcgaaagga agcggctgag gcgcttggaa cccgaaaagt ctcggtgctc ctggctacct
 181 cgcacagcgg tgcccgcccg gccgtcagta ccatggacag cagcgctgcc cccacgaacg
 241 ccagcaattg cactgatgcc ttggcgtact caagttgctc cccagcaccc agccccggtt
 301 cctgggtcaa cttgtcccac ttagatggca acctgaccga cccatgcggt ccgaaccgca
 361 ccaacctggg cgggagagac agcctgtgcc ctccgaccgg cagtccctcc atgatcacgg
 421 ccatcacgat catggccctc tactccatcg tgtgcgtggt ggggctcttc ggaaacttcc
 481 tggtcatgta tgtgattgtc agatacacca agatgaagac tgccaccaac atctacattt
 541 tcaaccttgc tctggcagat gccttagcca ccagtaccct gcccttccag agtgtgaatt
 601 acctaatggg aacatggcca tttggaacca tcctttgcaa gatagtgatc tccatagatt
 661 actataacat gttcaccagc atattcaccc tctgcaccat gagtgttgat cgatacattg
 721 cagtctgcca ccctgtcaag gccttagatt tccgtactcc ccgaaatgcc aaaattatca
 781 atgtctgcaa ctggatcctc tcttcagcca ttggtcttcc tgtaatgttc atggctacaa
 841 caaaatacag gcaaggttcc atagattgta cactaacatt ctctcatcca acctggtact
 901 gggaaaacct cgtgaagatc tgtgttttca tcttcgcctt cattatgcca gtgctcatca
 961 ttaccgtgtg ctatggactg atgatcttgc gcctcaagag tgtccgcatg ctctctggct
1021 ccaaagaaaa ggacaggaat cttcgaagga tcaccaggat ggtgctggtg gtggtggctg
1081 tgttcatcgt ctgctggact cccattcaca tttacgtcat cattaaagcc ttggttacaa
1141 tcccagaaac tacgttccag actgtttctt ggcacttctg cattgctcta ggttacacaa
1201 acagctgcct caacccagtc ctttatgcat ttctggatga aaacttcaaa cgatgcttca
1261 gagagttctg tatcccaacc tcttccaaca ttgagcaaca aaactccact cgaattcgtc
1321 agaagactag agaccacccc tccacggcca atacagtgga tagaactaat catcagctag
1381 aaaatctgga agcagaaact gctccgttgc cctaacaggg tctcatgcca ttccgacctt
1441 caccaagctt agaagccacc atgtatgtgg aagcaggttg cttcaagaat gtgtaggagg
1501 ctctaattct ctaggaaagt gcctactttt aggtcatcca acctctttcc tctctggcca
1561 ctctgctctg cacattagag ggacagccaa aagtaagtgg agcatttgga aggaaaggaa
1621 tataccacac cgaggagtcc agtttgtgca agacacccag tggaaccaaa acccatcgtg
1681 gtatgtgaat tgaagtcatc ataaaaggtg acccttctgt ctgtaagatt ttattttcaa
1741 gcaaatattt atgacctcaa caaagaagaa ccatcttttg ttaagttcac cgtagtaaca
1801 cataaagtaa atgctacctc tgatcaaagc accttgaatg gaaggtccga gtctttttag
1861 tgttttttgca agggaatgaa tccattattc tatttagac ttttaacttc aacttaaaat
1921 tagcatctgg ctaaggcatc attttcacct ccatttcttg gttttgtatt gtttaaaaaa
1981 aataacatct ctttcatcta gctccataat tgcaagggaa gagattagca tgaaaggtaa
2041 tctgaaacac agtcatgtgt canctgtaga aaggttgatt ctcatgcact ncaaatactt
2101 ccaaagagtc atcatgggggg atttttcatt cttaggcttt cagtggtttg ttcctggaat
2161 tc
```

600-1-266  FIGURE 3B
SEQ ID NO:6

| | | | | | | | | | | | | | | |
|---|---|---|---|---|---|---|---|---|---|---|---|---|---|---|
| Met | Asp | Ser | Ser | Ala | Ala | Pro | Thr | Asn | Ala | Ser | Asn | Cys | Thr | Asp | Ala |
| 1 | | | | 5 | | | | | 10 | | | | | 15 | |
| Leu | Ala | Tyr | Ser | Ser | Cys | Ser | Pro | Ala | Pro | Ser | Pro | Gly | Ser | Trp | Val |
| | | | 20 | | | | | 25 | | | | | 30 | | |
| Asn | Leu | Ser | His | Leu | Asp | Gly | Asn | Leu | *Thr* | Asp | Pro | Cys | Gly | Pro | Asn |
| | | 35 | | | | | 40 | | | | | 45 | | | |
| Arg | Thr | Asn | Leu | Gly | Gly | Arg | Asp | Ser | Leu | Cys | Pro | Pro | Thr | Gly | Ser |
| | 50 | | | | | 55 | | | | | 60 | | | | |
| Pro | Ser | Met | Ile | Thr | Ala | Ile | Thr | Ile | Met | Ala | Leu | Tyr | Ser | Ile | Val |
| 65 | | | | 70 | | | | | 75 | | | | | 80 | |
| Cys | Val | Val | Gly | Leu | Phe | Gly | Asn | Phe | Leu | Val | Met | Tyr | Val | Ile | Val |
| | | | | 85 | | | | | 90 | | | | | 95 | |
| Arg | Tyr | Thr | Lys | Met | Lys | Thr | Ala | Thr | Asn | Ile | Tyr | Ile | Phe | Asn | Leu |
| | | | 100 | | | | | 105 | | | | | 110 | | |
| Ala | Leu | Ala | Asp | Ala | Leu | Ala | Thr | Ser | Thr | Leu | Pro | Phe | Gln | Ser | Val |
| | | 115 | | | | | 120 | | | | | 125 | | | |
| Asn | Tyr | Leu | Met | Gly | Thr | Trp | Pro | Phe | Gly | Thr | Ile | Leu | Cys | Lys | Ile |
| | 130 | | | | | 135 | | | | | 140 | | | | |
| Val | Ile | Ser | Ile | Asp | Tyr | Tyr | Asn | Met | Phe | Thr | Ser | Ile | Phe | Thr | Leu |
| 145 | | | | | 150 | | | | | 155 | | | | | 160 |
| Cys | Thr | Met | Ser | Val | Asp | Arg | Tyr | Ile | Ala | Val | Cys | His | Pro | Val | Lys |
| | | | | 165 | | | | | 170 | | | | | 175 | |
| Ala | Leu | Asp | Phe | Arg | Thr | Pro | Arg | Asn | Ala | Lys | Ile | Ile | Asn | Val | Cys |
| | | | 180 | | | | | 185 | | | | | 190 | | |
| Asn | Trp | Ile | Leu | Ser | Ser | Ala | Ile | Gly | Leu | Pro | Val | Met | Phe | Met | Ala |
| | | 195 | | | | | 200 | | | | | 205 | | | |
| Thr | Thr | Lys | Tyr | Arg | Gln | Gly | Ser | Ile | Asp | Cys | Thr | Leu | Thr | Phe | Ser |
| | 210 | | | | | 215 | | | | | 220 | | | | |
| His | Pro | Thr | Trp | Tyr | Trp | Glu | Asn | Leu | Val | Lys | Ile | Cys | Val | Phe | Ile |
| 225 | | | | | 230 | | | | | 235 | | | | | 240 |
| Phe | Ala | Phe | Ile | Met | Pro | Val | Leu | Ile | Ile | Thr | Val | Cys | Tyr | Gly | Leu |
| | | | | 245 | | | | | 250 | | | | | 255 | |
| Met | Ile | Leu | Arg | Leu | Lys | Ser | Val | Arg | Met | Leu | Ser | Gly | Ser | Lys | Glu |
| | | | 260 | | | | | 265 | | | | | 270 | | |
| Lys | Asp | Arg | Asn | Leu | Arg | Arg | Ile | Thr | Arg | Met | Val | Leu | Val | Val | Val |
| | | 275 | | | | | 280 | | | | | 285 | | | |
| Ala | Val | Phe | Ile | Val | Cys | Trp | Thr | Pro | Ile | His | Ile | Tyr | Val | Ile | Ile |
| | 290 | | | | | 295 | | | | | 300 | | | | |
| Lys | Ala | Leu | Val | Thr | Ile | Pro | Glu | Thr | Thr | Phe | Gln | Thr | Val | Ser | Trp |
| 305 | | | | | 310 | | | | | 315 | | | | | 320 |
| His | Phe | Cys | Ile | Ala | Leu | Gly | Tyr | Thr | Asn | Ser | Cys | Leu | Asn | Pro | Val |
| | | | | 325 | | | | | 330 | | | | | 335 | |
| Leu | Tyr | Ala | Phe | Leu | Asp | Glu | Asn | Phe | Lys | Arg | Cys | Phe | Arg | Glu | Phe |
| | | | 340 | | | | | 345 | | | | | 350 | | |
| Cys | Ile | Pro | Thr | Ser | Ser | Asn | Ile | Glu | Gln | Gln | Asn | Ser | Thr | Arg | Ile |
| | | 355 | | | | | 360 | | | | | 365 | | | |
| Arg | Gln | Asn | Thr | Arg | Asp | His | Pro | Ser | Thr | Ala | Asn | Thr | Val | Asp | Arg |
| | 370 | | | | | 375 | | | | | 380 | | | | |
| Thr | Asn | His | Gln | Leu | Glu | Asn | Leu | Glu | Ala | Glu | Thr | Ala | Pro | Leu | Pro |
| 385 | | | | | 390 | | | | | 395 | | | | | 400 |

FIGURE 4

SEQ ID NO:7

```
   1 ggaattccgg ctataggcag aggagaatgt cagatgctca gctcggtccc ctccgcctga
  61 cgctcctctc tgtctcagcc aggactggtt tctgtaagaa acagcaggag ctgtggcagc
 121 ggcgaaagga agcggctgag gcgcttggaa cccgaaaagt ctcggtgctc ctggctacct
 181 cgcacagcgg tgcccgcccg gccgtcagta ccatggacag cagcgctgcc cccacgaacg
 241 ccagcaattg cactgatgcc ttggcgtact caagttgctc cccagcaccc agcccggtt
 301 cctgggtcaa cttgtcccac ttagatggca acctgtccga cccatgcggt ccgaaccgca
 361 ccaatctggg cgggagagac agcctgtgcc ctccgaccgg cagtccctcc atgatcacgg
 421 ccatcacgat catggccctc tactccatcg tgtgcgtggt ggggctcttc ggaaacttcc
 481 tggtcatgta tgtgattgtc agatacacca agatgaagac tgccaccaac atctacattt
 541 tcaaccttgc tctggcagat gcctagcca ccagtaccct gcccttccag agtgtgaatt
 601 acctaatggg aacatggcca tttggaacca tcctttgcaa gatagtgatc tccatagatt
 661 actataacat gttcaccagc atattcaccc tctgcaccat gagtgttgat cgatacattg
 721 cagtctgcca ccctgtcaag gccttagatt tccgtactcc ccgaaatgcc aaaattatca
 781 atgtctgcaa ctggatcctc tcttcagcca ttggtcttcc tgtaatgttc atggctacaa
 841 caaaatacag gcaaggttcc atagattgta cactaacatt ctctcatcca acctggtact
 901 gggaaaacct cgtgaagatc tgtgtttca tcttcgcctt cattatgcca gtgctcatca
 961 ttaccgtgtg ctatggactg atgatcttgc gcctcaagag tgtccgcatg ctctctggct
1021 ccaaagaaaa ggacaggaat cttcgaagga tcaccaggat ggtgctggtg gtggtggctg
1081 tgttcatcgt ctgctggact cccattcaca tttacgtcat cattaaagcc ttggttacaa
1141 tcccagaaac tacgttccag actgtttctt ggcacttctg cattgctcta ggttacacaa
1201 acagctgcct caacccagtc ctttatgcat ttctggatga aaacttcaaa cgatgcttca
1261 gagagttctg tatcccaacc tcttccaaca ttgagcaaca aaactccact cgaattcgtc
1321 agaacactag agaccacccc tccacggcca atacagtgga tagaactaat catcagctag
1381 aaaatctgga agcagaaact gctccgttgc cctaacaggg tctcatgcca ttccgacctt
1441 caccaagctt agaagccacc atgtatgtgg aagcaggttg cttcaagaat gtgtaggagg
1501 ctctaattct ctaggaaagt gcctactttt aggtcatcca acctctttcc tctctggcca
1561 ctctgctctg cacattagag ggacagccaa aagtaagtgg agcatttgga aggaaaggaa
1621 tataccacac cgaggagtcc agtttgtgca agacacccag tggaaccaaa acccatcgtg
1681 gtatgtgaat tgaagtcatc ataaaaggtg acccttctgt ctgtaagatt ttattttcaa
1741 gcaaatattt atgacctcaa caagaagaa ccatctttgt taagttcac cgtagtaaca
1801 cataaagtaa atgctacctc tgatcaaagc accttgaatg gaaggtccga gtcttttag
1861 tgttttgca agggaatgaa tccattattc tatttagac ttttaacttc aacttaaaat
1921 tagcatctgg ctaaggcatc attttcacct ccatttcttg gttttgtatt gtttaaaaaa
1981 aataacatct ctttcatcta gctccataat tgcaagggaa gagattagca tgaaaggtaa
2041 tctgaaacac agtcatgtgt canctgtaga aaggttgatt ctcatgcact ncaaatactt
2101 ccaaagagtc atcatggggg atttttcatt cttaggcttt cagtggtttg ttcctggaat
2161 tc
```

600-1-266        FIGURE 5

SEQ ID NO:8
```
    1 ggaattccgg ctataggcag aggagaatgt cagatgctca gctcggtccc ctccgcctga
   61 cgctcctctc tgtctcagcc aggactggtt tctgtaagaa acagcaggag ctgtggcagc
  121 ggcgaaagga agcggctgag gcgcttggaa cccgaaaagt ctcggtgctc ctggctacct
  181 cgcacagcgg tgcccgcccg gccgtcagta ccatggacag cagcgctgcc cccacgaacg
  241 ccagcaattg cactgatgcc ttggcgtact caagttgctc cccagcaccc agccccggtt
  301 cctgggtcaa cttgtcccac ttagatggca acctgtccga cccatgcggt ccgaaccgca
  361 ccaacctggg cgggagagac agcctatgcc ctccgaccgg cagtccctcc atgatcacgg
  421 ccatcacgat catggccctc tactccatcg tgtgcgtggt ggggctcttc ggaaacttcc
  481 tggtcatgta tgtgattgtc agatacacca agatgaagac tgccaccaac atctacattt
  541 tcaaccttgc tctggcagat gccttagcca ccagtaccct gcccttccag agtgtgaatt
  601 acctaatggg aacatggcca tttggaacca tcctttgcaa gatagtgatc tccatagatt
  661 actataacat gttcaccagc atattcaccc tctgcaccat gagtgttgat cgatacattg
  721 cagtctgcca ccctgtcaag gccttagatt tccgtactcc ccgaaatgcc aaaattatca
  781 atgtctgcaa ctggatcctc tcttcagcca ttggtcttcc tgtaatgttc atggctacaa
  841 caaaatacag gcaaggttcc atagattgta cactaacatt ctctcatcca acctggtact
  901 gggaaaacct cgtgaagatc tgtgttttca tcttcgcctt cattatgcca gtgctcatca
  961 ttaccgtgtg ctatggactg atgatcttgc gcctcaagag tgtccgcatg ctctctggct
 1021 ccaaagaaaa ggacaggaat cttcgaagga tcaccaggat ggtgctggtg gtggtggctg
 1081 tgttcatcgt ctgctggact cccattcaca tttacgtcat cattaaagcc ttggttacaa
 1141 tcccagaaac tacgttccag actgtttctt ggcacttctg cattgctcta ggttacacaa
 1201 acagctgcct caacccagtc ctttatgcat ttctggatga aaacttcaaa cgatgcttca
 1261 gagagttctg tatcccaacc tcttccaaca ttgagcaaca aaactccact cgaattcgtc
 1321 agaacactag agaccacccc tccacggcca atacagtgga tagaactaat catcagctag
 1381 aaaatctgga agcagaaact gctccgttgc cctaacaggg tctcatgcca ttccgacctt
 1441 caccaagctt agaagccacc atgtatgtgg aagcaggttg cttcaagaat gtgtaggagg
 1501 ctctaattct ctaggaaagt gcctactttt aggtcatcca acctctttcc tctctggcca
 1561 ctctgctctg cacattagag ggacagccaa aagtaagtgg agcatttgga aggaaaggaa
 1621 tataccacac cgaggagtcc agtttgtgca agacacccag tggaaccaaa acccatcgtg
 1681 gtatgtgaat tgaagtcatc ataaaaggtg accttctgt ctgtaagatt ttattttcaa
 1741 gcaaatattt atgacctcaa caaagaagaa ccatcttttg ttaagttcac cgtagtaaca
 1801 cataaagtaa atgctacctc tgatcaaagc accttgaatg gaaggtccga gtcttttag
 1861 tgttttgca agggaatgaa tccattattc tatttagac tttaacttc aacttaaaat
 1921 tagcatctgg ctaaggcatc atttcacct ccatttcttg gttttgtatt gtttaaaaaa
 1981 aataacatct ctttcatcta gctccataat tgcaagggaa gagattagca tgaaaggtaa
 2041 tctgaaacac agtcatgtgt canctgtaga aaggttgatt ctcatgcact ncaaatactt
 2101 ccaaagagtc atcatggggg atttttcatt cttaggcttt cagtggtttg ttcctggaat
 2161 tc
```

600-1-266        FIGURE 6A

SEQ ID NO:9

```
   1 ggaattccgg ctataggcag aggagaatgt cagatgctca gctcggtccc ctccgcctga
  61 cgctcctctc tgtctcagcc aggactggtt tctgtaagaa acagcaggag ctgtggcagc
 121 ggcgaaagga agcggctgag gcgcttggaa cccgaaaagt ctcggtgctc ctggctacct
 181 cgcacagcgg tgcccgcccg gccgtcagta ccatggacag cagcgctgcc cccacgaacg
 241 ccagcaattg cactgatgcc ttggcgtact caagttgctc cccagcaccc agcccggtt
 301 cctgggtcaa cttgtcccac ttagatggca acctgtccga cccatgcggt ccgaaccgca
 361 ccaacctggg cgggagagac agcctgtgcc ctccgaccgg cggcagtccctcc atgatcacgg
 424 ccatcacgat catggccctc tactccatcg tgtgcgtggt ggggctcttc ggaaacttcc
 484 tggtcatgta tgtgattgtc agatacacca agatgaagac tgccaccaac atctacattt
 544 tcaaccttgc tctggcagat gccttagcca ccagtaccct gcccttccag agtgtgaatt
 604 acctaatggg aacatggcca tttggaacca tcctttgcaa gatagtgatc tccatagatt
 664 actataacat gttcaccagc atattcaccc tctgcaccat gagtgttgat cgatacattg
 724 cagtctgcca ccctgtcaag gccttagatt tccgtactcc ccgaaatgcc aaaattatca
 784 atgtctgcaa ctggatcctc tcttcagcca ttggtcttcc tgtaatgttc atggctacaa
 844 caaaatacag gcaaggttcc atagattgta cactaacatt ctctcatcca acctggtact
 904 gggaaaacct cgtgaagatc tgtgttttca tcttcgcctt cattatgcca gtgctcatca
 964 ttaccgtgtg ctatggactg atgatcttgc gcctcaagag tgtccgcatg ctctctggct
1024 ccaaagaaaa ggacaggaat cttcgaagga tcaccaggat ggtgctggtg gtggtggctg
1084 tgttcatcgt ctgctggact cccattcaca tttacgtcat cattaaagcc ttggttacaa
1144 tcccagaaac tacgttccag actgtttctt ggcacttctg cattgctcta ggttacacaa
1204 acagctgcct caacccagtc ctttatgcat ttctggatga aaacttcaaa cgatgcttca
1264 gagagttctg tatcccaacc tcttccaaca ttgagcaaca aaactccact cgaattcgtc
1324 agaacactag agaccacccc tccacggcca atacagtgga tagaactaat catcagctag
1384 aaaatctgga agcagaaact gctccgttgc cctaacaggg tctcatgcca ttccgacctt
1444 caccaagctt agaagccacc atgtatgtgg aagcaggttg cttcaagaat gtgtaggagg
1504 ctctaattct ctaggaaagt gcctactttt aggtcatcca acctctttcc tctctggcca
1564 ctctgctctg cacattagag ggacagccaa aagtaagtgg agcatttgga aggaaaggaa
1624 tataccacac cgaggagtcc agtttgtgca agacacccag tggaaccaaa acccatcgtg
1684 gtatgtgaat tgaagtcatc ataaaaggtg acccttctgt ctgtaagatt ttattttcaa
1744 gcaaatattt atgacctcaa caaagaagaa ccatcttttg ttaagttcac cgtagtaaca
1804 cataaagtaa atgctacctc tgatcaaagc accttgaatg gaaggtccga gtcttttag
1864 tgttttttgca agggaatgaa tccattattc tattttagac ttttaacttc aacttaaaat
1924 tagcatctgg ctaaggcatc attttcacct ccatttcttg gttttgtatt gtttaaaaaa
1984 aataacatct ctttcatcta gctccataat tgcaagggaa gagattagca tgaaaggtaa
2044 tctgaaacac agtcatgtgt canctgtaga aaggttgatt ctcatgcact ncaaatactt
2104 ccaaagagtc atcatggggg attttttcatt cttaggcttt cagtggtttg ttcctggaat
2164 tc
```

600-1-266  FIGURE 6B
SEQ ID NO:10

| | | | | | | | | | | | | | | |
|---|---|---|---|---|---|---|---|---|---|---|---|---|---|---|
|Met|Asp|Ser|Ser|Ala|Ala|Pro|Thr|Asn|Ala|Ser|Asn|Cys|Thr|Asp|Ala|
|1| | | |5| | | |10| | | |15| | | |
|Leu|Ala|Tyr|Ser|Ser|Cys|Ser|Pro|Ala|Pro|Ser|Pro|Gly|Ser|Trp|Val|
| | | |20| | | | |25| | | | |30| | |
|Asn|Leu|Ser|His|Leu|Asp|Gly|Asn|Leu|Ser|Asp|Pro|Cys|Gly|Pro|Asn|
| | |35| | | | |40| | | | |45| | | |
|Arg|Thr|Asn|Leu|Gly|Gly|Arg|Asp|Ser|Leu|Cys|Pro|Pro|Thr|Gly|Gly Ser|
| |50| | | | |55| | | | |60| | | | |
|Pro|Ser|Met|Ile|Thr|Ala|Ile|Thr|Ile|Met|Ala|Leu|Tyr|Ser|Ile|Val|
|66| | | | |71| | | | |76| | | | |81|
|Cys|Val|Val|Gly|Leu|Phe|Gly|Asn|Phe|Leu|Val|Met|Tyr|Val|Ile|Val|
| | | | |86| | | | |91| | | | |96| |
|Arg|Tyr|Thr|Lys|Met|Lys|Thr|Ala|Thr|Asn|Ile|Tyr|Ile|Phe|Asn|Leu|
| | | |101| | | | |106| | | | |111| | |
|Ala|Leu|Ala|Asp|Ala|Leu|Ala|Thr|Ser|Thr|Leu|Pro|Phe|Gln|Ser|Val|
| | |116| | | | |121| | | | |126| | | |
|Asn|Tyr|Leu|Met|Gly|Thr|Trp|Pro|Phe|Gly|Thr|Ile|Leu|Cys|Lys|Ile|
| |131| | | | |136| | | | |141| | | | |
|Val|Ile|Ser|Ile|Asp|Tyr|Tyr|Asn|Met|Phe|Thr|Ser|Ile|Phe|Thr|Leu|
|146| | | | |151| | | | |156| | | | |161|
|Cys|Thr|Met|Ser|Val|Asp|Arg|Tyr|Ile|Ala|Val|Cys|His|Pro|Val|Lys|
| | | | |166| | | | |171| | | | |176| |
|Ala|Leu|Asp|Phe|Arg|Thr|Pro|Arg|Asn|Ala|Lys|Ile|Ile|Asn|Val|Cys|
| | |181| | | | |186| | | | |191| | | |
|Asn|Trp|Ile|Leu|Ser|Ser|Ala|Ile|Gly|Leu|Pro|Val|Met|Phe|Met|Ala|
| |196| | | | |201| | | | |206| | | | |
|Thr|Thr|Lys|Tyr|Arg|Gln|Gly|Ser|Ile|Asp|Cys|Thr|Leu|Thr|Phe|Ser|
| |211| | | | |216| | | | |221| | | | |
|His|Pro|Thr|Trp|Tyr|Trp|Glu|Asn|Leu|Val|Lys|Ile|Cys|Val|Phe|Ile|
|226| | | | |231| | | | |236| | | | |241|
|Phe|Ala|Phe|Ile|Met|Pro|Val|Leu|Ile|Ile|Thr|Val|Cys|Tyr|Gly|Leu|
| | | | |246| | | | |251| | | | |256| |
|Met|Ile|Leu|Arg|Leu|Lys|Ser|Val|Arg|Met|Leu|Ser|Gly|Ser|Lys|Glu|
| | | |261| | | | |266| | | | |271| | |
|Lys|Asp|Arg|Asn|Leu|Arg|Arg|Ile|Thr|Arg|Met|Val|Leu|Val|Val|Val|
| | |276| | | | |281| | | | |286| | | |
|Ala|Val|Phe|Ile|Val|Cys|Trp|Thr|Pro|Ile|His|Ile|Tyr|Val|Ile|Ile|
| |291| | | | |296| | | | |301| | | | |
|Lys|Ala|Leu|Val|Thr|Ile|Pro|Glu|Thr|Thr|Phe|Gln|Thr|Val|Ser|Trp|
|306| | | | |311| | | | |316| | | | |321|
|His|Phe|Cys|Ile|Ala|Leu|Gly|Tyr|Thr|Asn|Ser|Cys|Leu|Asn|Pro|Val|
| | | | |326| | | | |331| | | | |336| |
|Leu|Tyr|Ala|Phe|Leu|Asp|Glu|Asn|Phe|Lys|Arg|Cys|Phe|Arg|Glu|Phe|
| | | |341| | | | |346| | | | |351| | |
|Cys|Ile|Pro|Thr|Ser|Ser|Asn|Ile|Glu|Gln|Gln|Asn|Ser|Thr|Arg|Ile|
| | |356| | | | |361| | | | |366| | | |
|Arg|Gln|Asn|Thr|Arg|Asp|His|Pro|Ser|Thr|Ala|Asn|Thr|Val|Asp|Arg|
| |371| | | | |376| | | | |381| | | | |
|Thr|Asn|His|Gln|Leu|Glu|Asn|Leu|Glu|Ala|Glu|Thr|Ala|Pro|Leu|Pro|
|386| | | | |391| | | | |396| | | | |401|

SEQUENCE LISTING

```
<160> NUMBER OF SEQ ID NOS: 10

<210> SEQ ID NO 1
<211> LENGTH: 2162
<212> TYPE: DNA
<213> ORGANISM: Homo sapiens
<220> FEATURE:
<221> NAME/KEY: misc_feature
<222> LOCATION: 2063, 2091
<223> OTHER INFORMATION: n = A,T,C or G

<400> SEQUENCE: 1
ggaattccgg ctataggcag aggagaatgt cagatgctca gctcggtccc ctccgcctga      60
cgctcctctc tgtctcagcc aggactggtt tctgtaagaa acagcaggag ctgtggcagc     120
ggcgaaagga agcggctgag gcgcttggaa cccgaaaagt ctcggtgctc ctggctacct     180
cgcacagcgg tgcccgcccg gccgtcagta ccatggacag cagcgctgcc cccacgaacg     240
ccagcaattg cactgatgcc ttggcgtact caagttgctc cccagcaccc agccccggtt     300
cctgggtcaa cttgtcccac ttagatggca acctgtccga cccatgcggt ccgaaccgca     360
ccaacctggg cggagagac agcctgtgcc ctccgaccgg cagtccctcc atgatcacgg     420
ccatcacgat catggcccctc tactccatcg tgtgcgtggt ggggctcttc ggaaacttcc     480
```

-continued

```
tggtcatgta tgtgattgtc agatacacca agatgaagac tgccaccaac atctacattt   540
tcaaccttgc tctggcagat gccttagcca ccagtaccct gcccttccag agtgtgaatt   600
acctaatggg aacatggcca tttggaacca tcctttgcaa gatagtgatc tccatagatt   660
actataacat gttcaccagc atattcaccc tctgcaccat gagtgttgat cgatacattg   720
cagtctgcca ccctgtcaag gcctagatt tccgtactcc ccgaaatgcc aaaattatca    780
atgtctgcaa ctggatcctc tcttcagcca ttggtcttcc tgtaatgttc atggctacaa   840
caaaatacag gcaaggttcc atagattgta cactaacatt ctctcatcca acctggtact   900
gggaaaacct cgtgaagatc tgtgttttca tcttcgcctt cattatgcca gtgctcatca   960
ttaccgtgtg ctatggactg atgatcttgc gcctcaagag tgtccgcatg ctctctggct  1020
ccaaagaaaa ggacaggaat cttcgaagga tcaccaggat ggtgctggtg gtggtggctg  1080
tgttcatcgt ctgctggact cccattcaca tttacgtcat cattaaagcc ttggttacaa  1140
tcccagaaac tacgttccag actgtttctt ggcacttctg cattgctcta ggttacacaa  1200
acagctgcct caacccagtc ctttatgcat ttctggatga aaacttcaaa cgatgcttca  1260
gagagttctg tatcccaacc tcttccaaca ttgagcaaca aaactccact cgaattcgtc  1320
agaacactag agaccacccc tccacggcca atacagtgga tagaactaat catcagctag  1380
aaaatctgga agcagaaact gctccgttgc cctaacaggg tctcatgcca ttccgacctt  1440
caccaagctt agaagccacc atgtatgtgg aagcaggttg cttcaagaat gtgtaggagg  1500
ctctaattct ctaggaaagt gcctactttt aggtcatcca acctctttcc tctctggcca  1560
ctctgctctg cacattagag ggacagccaa agtaagtgg agcatttgga aggaaaggaa   1620
tataccacac cgaggagtcc agtttgtgca agacacccag tggaaccaaa acccatcgtg   1680
gtatgtgaat tgaagtcatc ataaaaggtg acccttctgt ctgtaagatt ttattttcaa   1740
gcaaatattt atgacctcaa caaagaagaa ccatcttttg ttaagttcac cgtagtaaca   1800
cataaagtaa atgctacctc tgatcaaagc accttgaatg aaggtccga gtcttttag    1860 tgttttttgca agggaatgaa tccattattc tattttagac ttttaacttc aacttaaaat  1920
tagcatctgg ctaaggcatc attttcacct ccatttcttg gttttgtatt gtttaaaaaa   1980
aataacatct ctttcatcta gctccataat tgcaagggaa gagattagca tgaaaggtaa   2040
tctgaaacac agtcatgtgt canctgtaga aaggttgatt ctcatgcact ncaaatactt   2100
ccaaagagtc atcatggggg atttttcatt cttaggcttt cagtggtttg ttcctggaat   2160
tc                                                                   2162
```

<210> SEQ ID NO 2
<211> LENGTH: 400
<212> TYPE: PRT
<213> ORGANISM: Homo sapiens

<400> SEQUENCE: 2

```
Met Asp Ser Ser Ala Ala Pro Thr Asn Ala Ser Asn Cys Thr Asp Ala
  1               5                  10                  15

Leu Ala Tyr Ser Ser Cys Ser Pro Ala Pro Ser Pro Gly Ser Trp Val
             20                  25                  30

Asn Leu Ser His Leu Asp Gly Asn Leu Ser Asp Pro Cys Gly Pro Asn
         35                  40                  45

Arg Thr Asn Leu Gly Gly Arg Asp Ser Leu Cys Pro Pro Thr Gly Ser
     50                  55                  60

Pro Ser Met Ile Thr Ala Ile Thr Ile Met Ala Leu Tyr Ser Ile Val
```

```
                 65                  70                  75                  80
Cys Val Val Gly Leu Phe Gly Asn Phe Leu Val Met Tyr Val Ile Val
                    85                  90                  95
Arg Tyr Thr Lys Met Lys Thr Ala Thr Asn Ile Tyr Ile Phe Asn Leu
                100                 105                 110
Ala Leu Ala Asp Ala Leu Ala Thr Ser Thr Leu Pro Phe Gln Ser Val
                115                 120                 125
Asn Tyr Leu Met Gly Thr Trp Pro Phe Gly Thr Ile Leu Cys Lys Ile
                130                 135                 140
Val Ile Ser Ile Asp Tyr Tyr Asn Met Phe Thr Ser Ile Phe Thr Leu
145                 150                 155                 160
Cys Thr Met Ser Val Asp Arg Tyr Ile Ala Val Cys His Pro Val Lys
                    165                 170                 175
Ala Leu Asp Phe Arg Thr Pro Arg Asn Ala Lys Ile Ile Asn Val Cys
                180                 185                 190
Asn Trp Ile Leu Ser Ser Ala Ile Gly Leu Pro Val Met Phe Met Ala
                195                 200                 205
Thr Thr Lys Tyr Arg Gln Gly Ser Ile Asp Cys Thr Leu Thr Phe Ser
                210                 215                 220
His Pro Thr Trp Tyr Trp Glu Asn Leu Val Lys Ile Cys Val Phe Ile
225                 230                 235                 240
Phe Ala Phe Ile Met Pro Val Leu Ile Ile Thr Val Cys Tyr Gly Leu
                    245                 250                 255
Met Ile Leu Arg Leu Lys Ser Val Arg Met Leu Ser Gly Ser Lys Glu
                260                 265                 270
Lys Asp Arg Asn Leu Arg Arg Ile Thr Arg Met Val Leu Val Val Val
                275                 280                 285
Ala Val Phe Ile Val Cys Trp Thr Pro Ile His Ile Tyr Val Ile Ile
                290                 295                 300
Lys Ala Leu Val Thr Ile Pro Glu Thr Thr Phe Gln Thr Val Ser Trp
305                 310                 315                 320
His Phe Cys Ile Ala Leu Gly Tyr Thr Asn Ser Cys Leu Asn Pro Val
                    325                 330                 335
Leu Tyr Ala Phe Leu Asp Glu Asn Phe Lys Arg Cys Phe Arg Glu Phe
                340                 345                 350
Cys Ile Pro Thr Ser Ser Asn Ile Glu Gln Gln Asn Ser Thr Arg Ile
                355                 360                 365
Arg Gln Asn Thr Arg Asp His Pro Ser Thr Ala Asn Thr Val Asp Arg
                370                 375                 380
Thr Asn His Gln Leu Glu Asn Leu Glu Ala Glu Thr Ala Pro Leu Pro
385                 390                 395                 400
```

<210> SEQ ID NO 3
<211> LENGTH: 2162
<212> TYPE: DNA
<213> ORGANISM: Homo sapiens
<220> FEATURE:
<221> NAME/KEY: misc_feature
<222> LOCATION: 2063, 2091
<223> OTHER INFORMATION: n = A,T,C or G

<400> SEQUENCE: 3

```
ggaattccgg ctataggcag aggagaatgt cagatgctca gctcggtccc ctccgcctga    60
cgctcctctc tgtctcagcc aggactggtt tctgtaagaa acagcaggag ctgtggcagc   120
ggcgaaagga agcggctgag gcgcttggaa cccgaaaagt ctcggtgctc ctggctacct   180
```

-continued

```
cgcacagcgg tgcccgcccg gccgtcagta ccatggacag cagcgctgcc cccacgaacg    240
ccagcaattg cactgatgcc ttggcgtact caagttgccc ccagcaccc agccccggtt    300 cctgggtcaa cttgtcccac ttagatggca acctgtccga cccatgcggt ccgaaccgca    360
ccaacctggg cgggagagac agcctgtgcc ctccgaccgg cagtccctcc atgatcacgg    420
ccatcacgat catggccctc tactccatcg tgtgcgtggt ggggctcttc ggaaacttcc    480
tggtcatgta tgtgattgtc agatacacca agatgaagac tgccaccaac atctacattt    540
tcaaccttgc tctggcagat gcctt agcca ccagtaccct gccct tccag agtgtgaatt    600 acctaatggg aacatggcca tttggaacca tcctttgcaa gatagtgatc tccatagatt    660
actataacat gttcaccagc atattcaccc tctgcaccat gagtgttgat cgatacattg    720
cagtctgcca ccctgtcaag gccttagatt ccgtactcc ccgaaatgcc aaaattatca    780
atgtctgcaa ctggatcctc tcttcagcca ttggtcttcc tgtaatgttc atggctacaa    840
caaaatacag gcaaggttcc atagattgta cactaacatt ctctcatcca acctggtact    900
gggaaaacct cgtgaagatc tgtgttttca tcttcgcctt cattatgcca gtgctcatca    960
ttaccgtgtg ctatggactg atgatcttgc gcctcaagag tgtccgcatg ctctctggct    1020
ccaaagaaaa ggacaggaat cttcgaagga tcaccaggat ggtgctggtg gtggtggctg    1080
tgttcatcgt ctgctggact cccattcaca tttacgtcat cattaaagcc ttggttacaa    1140
tcccagaaac tacgttccag actgtttctt ggcacttctg cattgctcta ggttacacaa    1200
acagctgcct caacccagtc ctttatgcat ttctggatga aaacttcaaa cgatgcttca    1260
gagagttctg tatcccaacc tcttccaaca ttgagcaaca aaactccact cgaattcgtc    1320
agaacactag agaccacccc tccacggcca atacagtgga tagaactaat catcagctag    1380
aaaatctgga agcagaaact gctccgttgc cctaacaggg tctcatgcca ttccgaccttt   1440 caccaagctt agaagccacc atgtatgtgg aagcaggttg cttcaagaat gtgtaggagg    1500
ctctaattct ctaggaaagt gcctactttt aggtcatcca acctctttcc tctctggcca    1560
ctctgctctg cacattagag ggacagccaa agtaagtgg agcatttgga aggaaaggaa    1620
tataccacac cgaggagtcc agtttgtgca agacacccag tggaaccaaa acccatcgtg    1680
gtatgtgaat tgaagtcatc ataaaaggtg acccttctgt ctgtaagatt ttattttcaa    1740
gcaaatattt atgacctcaa caaagaagaa ccatcttttg ttaagttcac cgtagtaaca    1800
cataaagtaa atgctacctc tgatcaaagc accttgaatg gaaggtccga gtcttttttag    1860 tgttttttgca agggaatgaa tccattattc tattttagac ttttaacttc aacttaaaat    1920
tagcatctgg ctaaggcatc attttcacct ccatttcttg gttttgtatt gtttaaaaaa    1980
aataacatct cttt catcta gctccataat tgcaaggaa gagattagca tgaaaggtaa    2040
tctgaaacac agtcatgtgt canctgtaga aaggttgatt ctcatgcact ncaaatactt    2100
ccaaagagtc atcatggggg attttt catt cttaggcttt cagtggtttg ttcctggaat    2160
tc                                                                   2162
```

<210> SEQ ID NO 4
<211> LENGTH: 400
<212> TYPE: PRT
<213> ORGANISM: Homo sapiens

<400> SEQUENCE: 4

Met Asp Ser Ser Ala Ala Pro Thr Asn Ala Ser Asn Cys Thr Asp Ala
  1               5                  10                  15

```
Leu Ala Tyr Ser Ser Cys Pro Ala Pro Ser Pro Gly Ser Trp Val
            20                  25                  30

Asn Leu Ser His Leu Asp Gly Asn Leu Ser Asp Pro Cys Gly Pro Asn
            35                  40                  45

Arg Thr Asn Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
            115                 120                 125

Asn Tyr Leu Met Gly Thr Trp Pro Phe Gly Thr Ile Leu Cys Lys Ile
130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
            195                 200                 205

Thr Thr Lys Tyr Arg Gln Gly Ser Ile Asp Cys Thr Leu Thr Phe Ser
        210                 215                 220

His Pro Thr Trp Tyr Trp Glu Asn Leu Val Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
            275                 280                 285

Ala Val Phe Ile Val Cys Trp Thr Pro Ile His Ile Tyr Val Ile Ile
        290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
        370                 375                 380

Thr Asn His Gln Leu Glu Asn Leu Glu Ala Glu Thr Ala Pro Leu Pro
385                 390                 395                 400

<210> SEQ ID NO 5
<211> LENGTH: 2162
<212> TYPE: DNA
<213> ORGANISM: Homo sapiens
<220> FEATURE:
```

<221> NAME/KEY: misc_feature
<222> LOCATION: 2063, 2091
<223> OTHER INFORMATION: n = A,T,C or G

<400> SEQUENCE: 5

```
ggaattccgg ctataggcag aggagaatgt cagatgctca gctcggtccc ctccgcctga      60
cgctcctctc tgtctcagcc aggactggtt tctgtaagaa acagcaggag ctgtggcagc     120
ggcgaaagga agcggctgag gcgcttggaa cccgaaaagt ctcggtgctc ctggctacct     180
cgcacagcgg tgcccgcccg gccgtcagta ccatggacag cagcgctgcc cccacgaacg     240
ccagcaattg cactgatgcc ttggcgtact caagttgctc cccagcaccc agccccggtt     300
cctgggtcaa cttgtcccac ttagatggca acctgaccga cccatgcggt ccgaaccgca     360
ccaacctggg cgggagagac agcctgtgcc ctccgaccgg cagtccctcc atgatcacgg     420
ccatcacgat catggccctc tactccatcg tgtgcgtggt ggggctcttc ggaaacttcc     480
tggtcatgta tgtgattgtc agatacacca agatgaagac tgccaccaac atctacattt     540
tcaaccttgc tctggcagat gccttagcca ccagtaccct gcccttccag agtgtgaatt     600
acctaatggg aacatggcca tttggaacca tcctttgcaa gatagtgatc tccatagatt     660
actataacat gttcaccagc atattcaccc tctgcaccat gagtgttgat cgatacattg     720
cagtctgcca ccctgtcaag gccttagatt tccgtactcc ccgaaatgcc aaaattatca     780
atgtctgcaa ctggatcctc tcttcagcca ttggtcttcc tgtaatgttc atggctacaa     840
caaaatacag gcaaggttcc atagattgta cactaacatt ctctcatcca acctggtact     900
gggaaaacct cgtgaagatc tgtgtttttca tcttcgcctt cattatgcca gtgctcatca     960
ttaccgtgtg ctatggactg atgatcttgc gcctcaagag tgtccgcatg ctctctggct    1020
ccaaagaaaa ggacaggaat cttcgaagga tcaccaggat ggtgctggtg gtggtggctg    1080
tgttcatcgt ctgctggact cccattcaca tttacgtcat cattaaagcc ttggttacaa    1140
tcccagaaac tacgttccag actgtttctt ggcacttctg cattgctcta ggttacacaa    1200
acagctgcct caacccagtc ctttatgcat ttctggatga aaacttcaaa cgatgcttca    1260
gagagttctg tatcccaacc tcttccaaca ttgagcaaca aaactccact cgaattcgtc    1320
agaacactag agaccacccc tccacggcca atacagtgga tagaactaat catcagctag    1380
aaaatctgga agcagaaact gctccgttgc cctaacaggg tctcatgcca ttccgacctt    1440
caccaagctt agaagccacc atgtatgtgg aagcaggttg cttcaagaat gtgtaggagg    1500
ctctaattct ctaggaaagt gcctactttt aggtcatcca acctctttcc tctctggcca    1560
ctctgctctg cacattagag ggacagccaa aagtaagtgg agcatttgga aggaaaggaa    1620
tataccacac cgaggagtcc agtttgtgca agacacccag tggaaccaaa acccatcgtg    1680
gtatgtgaat tgaagtcatc ataaaaggtg acccttctgt ctgtaagatt ttattttcaa    1740
gcaaatattt atgacctcaa caagaagaa ccatctttg ttaagttcac cgtagtaaca    1800
cataaagtaa atgctaccct tgatcaaagc accttgaatg gaaggtccga gtctttttag    1860
tgttttttgca agggaatgaa tccattattc tattttagac ttttaacttc aacttaaaat    1920
tagcatctgg ctaaggcatc attttcacct ccatttcttg gttttgtatt gtttaaaaaa    1980
aataacatct ctttcatcta gctccataat tgcaagggaa gagattagca tgaaaggtaa    2040
tctgaaacac agtcatgtgt canctgtaga aaggttgatt ctcatgcact ncaaatactt    2100
ccaaagagtc atcatggggg attttttcatt cttaggcttt cagtggtttg ttcctggaat    2160
tc                                                                    2162
```

<210> SEQ ID NO 6
<211> LENGTH: 400
<212> TYPE: PRT
<213> ORGANISM: Homo sapiens

<400> SEQUENCE: 6

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Thr Asp Pro Cys Gly Pro Asn
        35                  40                  45

Arg Thr Asn Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
            85                  90                  95

Arg Tyr Thr Lys Met Lys Thr Ala Thr Asn Ile Tyr Ile Phe Asn Leu
        100                 105                 110

Ala Leu Ala Asp Ala Leu Ala Thr Ser Thr Leu Pro Phe Gln Ser Val
    115                 120                 125

Asn Tyr Leu Met Gly Thr Trp Pro Phe Gly Thr Ile Leu Cys Lys Ile
130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
            165                 170                 175

Ala Leu Asp Phe Arg Thr Pro Arg Asn Ala Lys Ile Ile Asn Val Cys
        180                 185                 190

Asn Trp Ile Leu Ser Ser Ala Ile Gly Leu Pro Val Met Phe Met Ala
    195                 200                 205

Thr Thr Lys Tyr Arg Gln Gly Ser Ile Asp Cys Thr Leu Thr Phe Ser
210                 215                 220

His Pro Thr Trp Tyr Trp Glu Asn Leu Val Lys Ile Cys Val Phe Ile
225                 230                 235                 240

Phe Ala Phe Ile Met Pro Val Leu Ile Ile Thr Val Cys Tyr Gly Leu
            245                 250                 255

Met Ile Leu Arg Leu Lys Ser Val Arg Met Leu Ser Gly Ser Lys Glu
        260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
            325                 330                 335

Leu Tyr Ala Phe Leu Asp Glu Asn Phe Lys Arg Cys Phe Arg Glu Phe
        340                 345                 350

Cys Ile Pro Thr Ser Ser Asn Ile Glu Gln Gln Asn Ser Thr Arg Ile
    355                 360                 365

Arg Gln Asn Thr Arg Asp His Pro Ser Thr Ala Asn Thr Val Asp Arg

|  | 370 |  | 375 |  | 380 |  |  |  |
| --- | --- | --- | --- | --- | --- | --- | --- | --- |
| Thr | Asn | His | Gln | Leu | Glu | Asn | Leu | Glu | Ala | Glu | Thr | Ala | Pro | Leu | Pro |
| 385 |  |  |  | 390 |  |  |  | 395 |  |  |  | 400 |  |  |  |

<210> SEQ ID NO 7
<211> LENGTH: 2162
<212> TYPE: DNA
<213> ORGANISM: Homo sapiens
<220> FEATURE:
<221> NAME/KEY: misc_feature
<222> LOCATION: 2063, 2091
<223> OTHER INFORMATION: n = A,T,C or G

<400> SEQUENCE: 7

```
ggaattccgg ctataggcag aggagaatgt cagatgctca gctcggtccc ctccgcctga    60
cgctcctctc tgtctcagcc aggactggtt tctgtaagaa acagcaggag ctgtggcagc   120
ggcgaaagga agcggctgag gcgcttggaa cccgaaaagt ctcggtgctc ctggctacct   180
cgcacagcgg tgcccgcccg gccgtcagta ccatggacag cagcgctgcc cccacgaacg   240
ccagcaattg cactgatgcc ttggcgtact caagttgctc cccagcaccc agccccggtt   300
cctgggtcaa cttgtcccac ttagatggca acctgtccga cccatgcggt ccgaaccgca   360
ccaatctggg cggagagac agcctgtgcc ctccgaccgg cagtccctcc atgatcacgg   420
ccatcacgat catggccctc tactccatcg tgtgcgtggt ggggctcttc ggaaacttcc   480
tggtcatgta tgtgattgtc agatacacca agatgaagac tgccaccaac atctacattt   540
tcaaccttgc tctggcagat gccttagcca ccagtaccct gcccttccag agtgtgaatt   600
acctaatggg aacatggcca tttggaacca tcctttgcaa gatagtgatc tccatagatt   660
actataacat gttcaccagc atattcaccc tctgcaccat gagtgttgat cgatacattg   720
cagtctgcca ccctgtcaag gccttagatt ccgtactcc cgaaatgcc aaaattatca   780
atgtctgcaa ctggatcctc tcttcagcca ttggtcttcc tgtaatgttc atggctacaa   840
caaaatacag gcaaggttcc atagattgta cactaacatt ctctcatcca acctggtact   900
gggaaaacct cgtgaagatc tgtgttttca tcttcgcctt cattatgcca gtgctcatca   960
ttaccgtgtg ctatggactg atgatcttgc gcctcaagag tgtccgcatg ctctctggct  1020
ccaaagaaaa ggacaggaat cttcgaagga tcaccaggat ggtgctggtg gtggtggctg  1080
tgttcatcgt ctgctggact cccattcaca tttacgtcat cattaaagcc ttggttacaa  1140
tcccagaaac tacgttccag actgtttctt ggcacttctg cattgctcta ggttacacaa  1200
acagctgcct caacccagtc ctttatgcat ttctggatga aaacttcaaa cgatgcttca  1260
gagagttctg tatcccaacc tcttccaaca ttgagcaaca aaactccact cgaattcgtc  1320
agaacactag agaccacccc tccacggcca atacagtgga tagaactaat catcagctag  1380
aaaatctgga agcagaaact gctccgttgc cctaacaggg tctcatgcca ttccgacctt  1440
caccaagctt agaagccacc atgtatgtgg aagcaggttg cttcaagaat gtgtaggagg  1500
ctctaattct ctaggaaagt gcctactttt aggtcatcca acctctttcc tctctggcca  1560
ctctgctctg cacattagag ggacagccaa agtaagtgg agcatttgga aggaaaggaa  1620
tataccacac cgaggagtcc agtttgtgca agacacccag tggaaccaaa cccatcgtg  1680
gtatgtgaat tgaagtcatc ataaaaggtg acccttctgt ctgtaagatt ttattttcaa  1740
gcaaatattt atgacctcaa caagaagaa ccatcttttg ttaagttcac cgtagtaaca  1800
cataaagtaa atgctacctc tgatcaaagc acctgaatg gaaggtccga gtcttttag  1860
```

| | |
|---|---|
| tgtttttgca agggaatgaa tccattattc tattttagac ttttaacttc aacttaaaat | 1920 |
| tagcatctgg ctaaggcatc attttcacct ccatttcttg gttttgtatt gtttaaaaaa | 1980 |
| aataacatct ctttcatcta gctccataat tgcaagggaa gagattagca tgaaaggtaa | 2040 |
| tctgaaacac agtcatgtgt canctgtaga aaggttgatt ctcatgcact ncaaatactt | 2100 |
| ccaaagagtc atcatggggg attttcatt cttaggcttt cagtggtttg ttcctggaat | 2160 |
| tc | 2162 |

<210> SEQ ID NO 8
<211> LENGTH: 2162
<212> TYPE: DNA
<213> ORGANISM: Homo sapiens
<220> FEATURE:
<221> NAME/KEY: misc_feature
<222> LOCATION: 2063, 2091
<223> OTHER INFORMATION: n = A,T,C or G

<400> SEQUENCE: 8

| | |
|---|---|
| ggaattccgg ctataggcag aggagaatgt cagatgctca gctcggtccc ctccgcctga | 60 |
| cgctcctctc tgtctcagcc aggactggtt tctgtaagaa acagcaggag ctgtggcagc | 120 |
| ggcgaaagga agcggctgag gcgcttggaa cccgaaaagt ctcggtgctc ctggctacct | 180 |
| cgcacagcgg tgcccgcccg gccgtcagta ccatggacag cagcgctgcc cccacgaacg | 240 |
| ccagcaattg cactgatgcc ttggcgtact caagttgctc cccagcaccc agccccggtt | 300 |
| cctgggtcaa cttgtcccac ttagatggca acctgtccga cccatgcggt ccgaaccgca | 360 |
| ccaacctggg cgggagagac agcctatgcc ctccgaccgg cagtccctcc atgatcacgg | 420 |
| ccatcacgat catggccctc tactccatcg tgtgcgtggt ggggctcttc ggaaacttcc | 480 |
| tggtcatgta tgtgattgtc agatacacca agatgaagac tgccaccaac atctacattt | 540 |
| tcaaccttgc tctggcagat gccttagcca ccagtacccc gccttccag agtgtgaatt | 600 |
| acctaatggg aacatggcca tttggaacca cctttgcaa gatagtgatc tccatagatt | 660 |
| actataacat gttcaccagc atattcaccc tctgcaccat gagtgttgat cgatacattg | 720 |
| cagtctgcca ccctgtcaag gccttagatt tccgtactcc ccgaaatgcc aaaattatca | 780 |
| atgtctgcaa ctggatcctc tcttcagcca ttggtcttcc tgtaatgttc atggctacaa | 840 |
| caaaatacag gcaaggttcc atagattgta cactaacatt ctctcatcca acctggtact | 900 |
| gggaaaacct cgtgaagatc tgtgttttca tcttcgcctt cattatgcca gtgctcatca | 960 |
| ttaccgtgtg ctatggactg atgatcttgc gcctcaagag tgtccgcatg ctctctggct | 1020 |
| ccaaagaaaa ggacaggaat cttcgaagga tcaccaggat ggtgctggtg gtggtggctg | 1080 |
| tgttcatcgt ctgctggact cccattcaca tttacgtcat cattaaagcc ttggttacaa | 1140 |
| tcccagaaac tacgttccag actgtttctt ggcacttctg cattgctcta ggttacacaa | 1200 |
| acagctgcct caacccagtc ctttatgcat ttctggatga aaacttcaaa cgatgcttca | 1260 |
| gagagttctg tatcccaacc tcttccaaca ttgagcaaca aaactccact cgaattcgtc | 1320 |
| agaacactag agaccacccc tccacggcca atacagtgga tagaactaat catcagctag | 1380 |
| aaaatctgga agcagaaact gctccgttgc cctaacaggg tctcatgcca ttccgacctt | 1440 |
| caccaagctt agaagccacc atgtatgtgg aagcaggttg cttcaagaat gtgtaggagg | 1500 |
| ctctaattct ctaggaaagt gcctactttt aggtcatcca acctctttcc tctctggcca | 1560 |
| ctctgctctg cacattagag ggacagccaa agtaagtgg agcatttgga aggaaaggaa | 1620 |
| tataccacac cgaggagtcc agtttgtgca agacacccag tggaaccaaa acccatcgtg | 1680 |

-continued

```
gtatgtgaat tgaagtcatc ataaaaggtg acccttctgt ctgtaagatt ttatttcaa    1740 gcaaatattt atgacctcaa caaagaagaa ccatcttttg ttaagttcac cgtagtaaca    1800
cataaagtaa atgctacctc tgatcaaagc accttgaatg aaggtccga gtcttttag    1860 tgttttgca agggaatgaa tccattattc tattttagac ttttaacttc aacttaaaat    1920
tagcatctgg ctaaggcatc attttcacct ccatttcttg gttttgtatt gtttaaaaaa    1980
aataacatct ctttcatcta gctccataat tgcaagggaa gagattagca tgaaaggtaa    2040
tctgaaacac agtcatgtgt canctgtaga aaggttgatt ctcatgcact ncaaatactt    2100
ccaaagagtc atcatggggg atttttcatt cttaggcttt cagtggtttg ttcctggaat    2160
tc                                                                  2162
```

<210> SEQ ID NO 9
<211> LENGTH: 2165
<212> TYPE: DNA
<213> ORGANISM: Homo sapiens
<220> FEATURE:
<221> NAME/KEY: misc_feature
<222> LOCATION: 2066, 2094
<223> OTHER INFORMATION: n = A,T,C or G

<400> SEQUENCE: 9

```
ggaattccgg ctataggcag aggagaatgt cagatgctca gctcggtccc ctccgcctga     60
cgctcctctc tgtctcagcc aggactggtt tctgtaagaa acagcaggag ctgtggcagc    120
ggcgaaagga agcggctgag gcgcttggaa cccgaaaagt ctcggtgctc ctggctacct    180
cgcacagcgg tgcccgcccg gccgtcagta ccatggacag cagcgctgcc cccacgaacg    240
ccagcaattg cactgatgcc ttggcgtact caagttgctc cccagcaccc agccccggtt    300
cctgggtcaa cttgtcccac ttagatggca acctgtccga cccatgcggt ccgaaccgca    360
ccaacctggg cgggagagac agcctgtgcc tccgaccggg cggcagtccc tccatgatca    420
cggccatcac gatcatggcc ctctactcca tcgtgtgcgt ggtggggctc ttcggaaact    480
tcctggtcat gtatgtgatt gtcagataca ccaagatgaa gactgccacc aacatctaca    540
ttttcaacct tgctctggca gatgccttag ccaccagtac cctgcccttc cagagtgtga    600
attacctaat gggaacatgg ccatttggaa ccatcctttg caagatagtg atctccatag    660
attactataa catgttcacc agcatattca cctctgcac catgagtgtt gatcgataca    720
ttgcagtctg ccacccthtc aaggcttag atttccgtac tccccgaaat gccaaaatta    780
tcaatgtctg caactggatc ctctcttcag ccattggtct tcctgtaatg ttcatggcta    840
caacaaaata caggcaaggt tccatagatt gtacactaac attctctcat ccaacctggt    900
actgggaaaa cctcgtgaag atctgtgttt tcatcttcgc cttcattatg ccagtgctca    960
tcattaccgt gtgctatgga ctgatgatct tgcgcctcaa gagtgtccgc atgctctctg   1020
gctccaaaga aaaggacagg aatcttcgaa ggatcaccag gatggtgctg gtggtggtgg   1080
ctgtgttcat cgtctgctgg actcccattc acatttacgt catcattaaa gccttggtta   1140
caatcccaga aactacgttc cagactgttt cttggcactt ctgcattgct ctaggttaca   1200
caaacagctg cctcaaccca gtcctttatg catttctgga tgaaaacttc aaacgatgct   1260
tcagagagtt ctgtatccca acctcttcca acattgagca acaaaactcc actcgaattc   1320
gtcagaacac tagagaccac ccctccacgg ccaatacagt ggatagaact aatcatcagc   1380
tagaaaatct ggaagcagaa actgctccgt tgccctaaca gggtctcatg ccattccgac   1440
```

-continued

```
cttcaccaag cttagaagcc accatgtatg tggaagcagg ttgcttcaag aatgtgtagg    1500
aggctctaat tctctaggaa agtgcctact tttaggtcat ccaacctctt tcctctctgg    1560
ccactctgct ctgcacatta gagggacagc caaaagtaag tggagcattt ggaaggaaag    1620
gaatatacca caccgaggag tccagtttgt gcaagacacc cagtggaacc aaaacccatc    1680
gtggtatgtg aattgaagtc atcataaaag gtgacccttc tgtctgtaag atttatttt    1740 caagcaaata tttatgacct caacaaagaa gaaccatctt ttgttaagtt caccgtagta    1800
acacataaag taaatgctac ctctgatcaa agcaccttga atggaaggtc cgagtctttt    1860
tagtgttttt gcaagggaat gaatccatta ttctatttta gacttttaac ttcaacttaa    1920
aattagcatc tggctaaggc atcattttca cctccatttc ttggttttgt attgtttaaa    1980
aaaaataaca tctctttcat ctagctccat aattgcaagg gaagagatta gcatgaaagg    2040
taatctgaaa cacagtcatg tgtcanctgt agaaaggttg attctcatgc actncaaata    2100
cttccaaaga gtcatcatgg gggattttc attcttaggc tttcagtggt ttgttcctgg     2160
aattc                                                                2165
```

<210> SEQ ID NO 10
<211> LENGTH: 401
<212> TYPE: PRT
<213> ORGANISM: Homo sapiens

<400> SEQUENCE: 10

```
Met Asp Ser Ser Ala Ala Pro Thr Asn Ala Ser Asn Cys Thr Asp Ala
  1               5                  10                  15

Leu Ala Tyr Ser Ser Cys Ser Pro Ala Pro Ser Pro Gly Ser Trp Val
                 20                  25                  30

Asn Leu Ser His Leu Asp Gly Asn Leu Ser Asp Pro Cys Gly Pro Asn
             35                  40                  45

Arg Thr Asn Leu Gly Gly Arg Asp Ser Leu Cys Pro Pro Thr Gly Gly
         50                  55                  60

Ser Pro Ser Met Ile Thr Ala Ile Thr Ile Met Ala Leu Tyr Ser Ile
 65                  70                  75                  80

Val Cys Val Val Gly Leu Phe Gly Asn Phe Leu Val Met Tyr Val Ile
                 85                  90                  95

Val Arg Tyr Thr Lys Met Lys Thr Ala Thr Asn Ile Tyr Ile Phe Asn
                100                 105                 110

Leu Ala Leu Ala Asp Ala Leu Ala Thr Ser Thr Leu Pro Phe Gln Ser
            115                 120                 125

Val Asn Tyr Leu Met Gly Thr Trp Pro Phe Gly Thr Ile Leu Cys Lys
        130                 135                 140

Ile Val Ile Ser Ile Asp Tyr Tyr Asn Met Phe Thr Ser Ile Phe Thr
145                 150                 155                 160

Leu Cys Thr Met Ser Val Asp Arg Tyr Ile Ala Val Cys His Pro Val
                165                 170                 175

Lys Ala Leu Asp Phe Arg Thr Pro Arg Asn Ala Lys Ile Ile Asn Val
            180                 185                 190

Cys Asn Trp Ile Leu Ser Ser Ala Ile Gly Leu Pro Val Met Phe Met
        195                 200                 205

Ala Thr Thr Lys Tyr Arg Gln Gly Ser Ile Asp Cys Thr Leu Thr Phe
    210                 215                 220

Ser His Pro Thr Trp Tyr Trp Glu Asn Leu Val Lys Ile Cys Val Phe
225                 230                 235                 240
```

-continued

```
Ile Phe Ala Phe Ile Met Pro Val Leu Ile Ile Thr Val Cys Tyr Gly
            245                 250                 255

Leu Met Ile Leu Arg Leu Lys Ser Val Arg Met Leu Ser Gly Ser Lys
            260                 265                 270

Glu Lys Asp Arg Asn Leu Arg Arg Ile Thr Arg Met Val Leu Val Val
            275                 280                 285

Val Ala Val Phe Ile Val Cys Trp Thr Pro Ile His Ile Tyr Val Ile
    290                 295                 300

Ile Lys Ala Leu Val Thr Ile Pro Glu Thr Thr Phe Gln Thr Val Ser
305                 310                 315                 320

Trp His Phe Cys Ile Ala Leu Gly Tyr Thr Asn Ser Cys Leu Asn Pro
                325                 330                 335

Val Leu Tyr Ala Phe Leu Asp Glu Asn Phe Lys Arg Cys Phe Arg Glu
                340                 345                 350

Phe Cys Ile Pro Thr Ser Ser Asn Ile Glu Gln Gln Asn Ser Thr Arg
            355                 360                 365

Ile Arg Gln Asn Thr Arg Asp His Pro Ser Thr Ala Asn Thr Val Asp
    370                 375                 380

Arg Thr Asn His Gln Leu Glu Asn Leu Glu Ala Glu Thr Ala Pro Leu
385                 390                 395                 400

Pro
```

ALLELES OF THE HUMAN MU OPIOID RECEPTOR, DIAGNOSTIC METHODS USING SAID ALLELES, AND METHODS OF TREATMENT BASED THEREON

CROSS-REFERENCE TO RELATED APPLICATION

This Application claims priority to provisional application Ser. No. 60/212,225, filed Jun. 16, 2000, incorporated herein by reference in its entirety.

GOVERNMENTAL SUPPORT

This invention was made government support under Grant Nos. NIH-NIDA P50-DA05130 and NIH-NIDA K05-DA00049 awarded by the National Institute of Drug Addiction. The Government has certain rights in the invention.

FIELD OF THE INVENTION

This invention relates generally to alleles of the human mu opioid receptor gene, along with products derived from such alleles. Also included herein are methods of diagnosing various susceptibilities using such alleles and determining treatment for certain diseases based upon the presence of specific alleles of the human mu opioid receptor gene, and various diseases or disorders related to physiological functions regulated by the hypothalamus pituitary adrenal axis (HPA) or the hypothalamus pituitary gonadal axis (HPG).

BACKGROUND OF THE INVENTION

Opioid drugs have various effects on perception of pain, consciousness, motor control, mood, autonomic function, and can also induce physical dependence. The endogenous opioid system plays an important role in modulating endocrine, cardiovascular, respiratory, gastrointestinal functions, and immune functions. Opioids, either exogenous or endogenous, exert their actions by binding to specific membrane-associated receptors.

Examples of exogenous opioids presently known include, opium, heroin, morphine, codeine, fentanyl, and methadone, to name only a few. Moreover, a family of over 20 endogenous opioid peptides has been identified, wherein the members possess common structural features, including a positive charge juxtaposed with an aromatic ring that is required for interaction with an opioid receptor. It has been determined that most, if not all the endogenous opioid peptides are derived from the proteolytic processing of three precursor proteins, i.e., pro-opiomelanocortin, proenkephalin, and prodynorphin. In addition, a fourth class of endogenous opioids, the endorphins, has been identified (the gene encoding these proteins has not yet been cloned). In the processing of the endogenous opioid precursor proteins, initial cleavages are made by membrane-bound proteases that cut next to pairs of positively charged amino acid residues, and then trimming reactions produce the final endogenous opioids secreted from cells in vivo. Different cell types contain different processing enzymes so that, for example proopiomelanocortin can be processed into different endogenous peptides by different cells. For example, in the anterior lobe of the pituitary gland, only corticotropin (ACTH), β-lipotropin, and β-endorphin are produced. Both pro-enkephalin and pro-dynorphin are similarly processed by specific enzymes in specific cells to yield multiple opioid peptides.

Pharmacological studies have suggested there are numerous classes of opioid receptors which bind to exogenous and endogenous opioids. These classes differ in their affinity for various opioid ligands and in their cellular and organ distribution. Moreover, although the different classes are believed to serve different physiological functions, there is substantial overlap of function, as well as of distribution.

In particular, there are at least three known types of opioid receptors, mu (μ), delta (δ), and kappa (κ), to which morphine, the enkephalins, and the dynorphins can bind. These three opioid receptor types are the sites of action of opioid ligands producing analgesic effects. However, the type of pain inhibited and the secondary functions vary with each receptor type. The mu receptor is generally regarded as primarily associated with pain relief, and drug or other chemical dependence, i.e., addiction and alcoholism.

The human mu opioid receptor, which modulates corticotropin releasing hormone, has been isolated and described in PCT Application WO 95/07983 (Mar. 23, 1995) (SEQ ID NO:1) as well as in Chen, Y., Mestek, A., Hurley, J. A., & Yu, L. (1993) *Mol. Pharmacol.* 44, 8–12, and Wang, et al., *FEBS Letters,* (1994)338:217–222. Furthermore, SEQ ID NO:1 can readily be obtained in GENBANK under accession number L25119. The cDNA therefor contains an open reading frame capable of encoding a protein of 400 amino acid residues with 94% sequence similarity to the rat mu opioid receptor. Hydropathy analysis of the deduced protein indicates the presence of seven hydrophobic domains, typical of G-protein-coupled receptors. The N-terminus contains five potential N-linked glycosylation sites which remain conserved between the human and the rat mu opioid receptor. A variant in which Asn-40 is changed to Asp (N40D) is reported in GENBANK Accession No. U12569. New polymorphisms G24A (silent), G779A (Arg260His), and G942A (silent) of the mu opioid receptor have been described in co-pending application Ser. No. 09/113,426, filed Jul. 10, 1998, and Ser. No. 09/351,198, filed Jul. 9, 1999, both of which are incorporated herein by reference in their entireties.

In the body and brain, heroin is biotransformed to morphine, which acts at the mu opioid receptor and results in an euphoric effect and confers the reinforcing properties of the drug and contributes to development of addiction. Heroin addiction can be managed through treatment, primarily methadone maintenance. However, the biological basis of heroin addiction may include diversity of gene structure. Such genetic diversity of the human mu opioid receptor, and the impact of such diversity on receptor function, could contribute to the success or failure of pharmacological management. Similar problems with respect to patient response to pharmacological treatment could occur in most, if not all addictive diseases, such as heroin addiction, alcohol addiction, or cocaine addiction to name only a few, or a combination thereof.

Moreover, addiction to opioid drugs, especially heroin, is a major social problem in the United States, and throughout the world. For example, recent epidemiological assessments sponsored by the NIH-NIDA and other federal agencies have found that around 2.7 million persons in the United States have used heroin at some time. Moreover, the numbers of "hardcore" long-term heroin addicts (addiction being defined herein as self administration of a regular, multiple, daily dose use of a short-acting opioid, such as heroin, for one year or more, with the development of tolerance, physical dependence and drug-seeking behavior, a definition codified in the Federal guidelines governing pharmacotherapy using long-acting agents such as methadone or LAAM, and used as the minimal requirement for entry into treatment) are now estimated to be approximately one million persons. In addition, it has been estimated that around 24 million persons in the United States have used cocaine for some time, and of that number, approximately one million use cocaine regularly, and at least 600,000–700,000 are cocaine addicts.

In view of the importance of the human mu opioid receptor in the study of addiction, and the epidemic proportions of drug addiction, especially to heroin, alcohol or cocaine, or a combination thereof, in the United States and throughout the world, and its involvement in the neuroendocrine system, and physiological functions regulated thereby, efforts have been made to investigate whether any polymorphisms in the gene encoding the human mu opioid receptor exist in the population, and whether such polymorphisms result in a phenotype that has an increased or decreased susceptibility towards development of addiction to exogenous opioids, such as heroin, or alcohol, cocaine, or other addictive drugs. For example, in an article entitled "Human mu opioid receptor gene polymorphisms and vulnerability to substance abuse" (Berrettini, W. H., Hoehe, M. R., Ferraro, T. N., DeMaria, P. A., and Gottheil, E., *Addiction Biology* 2:303–308 (1997)), two polymorphisms in the human mu opioid receptor gene were reported. One polymorphism (G to T) occurs at nucleotide 175 preceding initiation of translation, and a second coding polymorphism C to T) at nucleotide 229 (with respect to transcription initiation) on exon I results in an Ala to Val residue change. However, data taken from a study indicated the C229T polymorphism does not differ in occurrence with statistical significance in addicts relative to non addicts (idem at 306). No functional studies were reported.

It has been further determined that a receptor for both endogenous and exogenous opioids modulates the activity of the hypothalamus pituitary adrenal axis (HPA) and the hypothalamus pituitary gonadal axis (HPG), which effects the neuroendocrine system and its production of signaling compounds that play important roles in regulation of numerous physiological functions. In particular, the neuroendocrine system involves the integration of the neural and endocrine systems of the body, and is responsible for the coordination of numerous bodily functions. An important part of this system is the hypothalamus, a specialized portion of the brain involved in receiving and relaying messages from the central nervous system to other parts of the body. Upon stimulation by chemical signals from the central nervous system, the hypothalamus secretes hypothalamic hormones, such as corticotropin releasing factor (CRF) or hormone and gonadotropin releasing hormone or luteinizing hormone releasing hormone. These factors in turn stimulate the anterior pituitary gland to secrete tropic hormones, or tropins, which are synthesized as relatively long polypeptides, and then are then biotransformed to produce active peptide hormones. Pro-opiomelanocortin, which is processed into several active peptide hormones, including adrenocorticotropic hormone (ACTH), is an example of a tropic hormone. ACTH stimulates the adrenal cortex to secrete additional hormones, like cortisol, a stress hormone in humans which regulates glucose metabolism, and targets many tissues in the body. In addition, examples of hormones produced by the anterior pituitary glad upon stimulation with gonadotropin releasing hormone include follicle-stimulating hormone and luteinizing hormones. These hormones stimulate the gonads, such as the ovaries and the testes, to secrete androgens, such as testosterone, progesterone, and estrogen, which in turn affect sexual development, sexual behavior, and other reproductive and nonreproductive functions. As a result, the endogenous opioid system plays an important role in modulating endocrine, reproductive, cardiovascular, respiratory, gastrointestinal, immune functions, sexual development and function, as well as a person's response to stress.

More specifically, in humans, it has been determined that chronic administration of opioids has an inhibitory effect on the HPA axis [McDonald et al., Effect of morphine and nalorphine on plasma hydrocortisone levels in man. *J. Pharmacol. Exp. Ther.* 125:241247 (1959)]. Basal levels of ACTH and cortisol are significantly disrupted in active heroin addicts: suppression of ACTH and cortisol and abnormal diurnal rhythms of these hormones are found [Kreek, Medical safety and side effects of methadone in tolerant individuals. *JAMA* 223:665–668 (1973)]. Basal levels and the diurnal rhythm of ACTH and cortisol, which are disrupted in active heroin addicts, have been shown to become normalized in moderate to high dose, long-term methadone-maintained patients when compared to those of healthy volunteer subjects [Kreek, 1973; Kreek et al., Circadian rhythms and levels of beta-endorphin, ACTH, and cortisol during chronic methadone maintenance treatment in humans. *Life Sci.* 33:409–411 (1983); Kreek et al., Prolonged (24 hour) infusion of the opioid antagonist naloxone does not significantly alter plasma levels of cortisol and ACTH in humans. *Proceedings of the 7th International Congress on Endocrinology*, Elsevier Science, p. 1170, 1984].

In healthy volunteers, ACTH and cortisol levels decrease below the basal levels in response to the infusion of β-endorphin indicating feedback of inhibition of pituitary ACTH release or suppression of hypothalamic CRF release by β-endorphin [Taylor et al., Beta-endorphin suppresses adrenocroticotropin and cortisol levels in normal human subjects. *J. Clin. Endocrinol. Metab.* 57:592–596 (1983)], and also naloxone (an opioid antagonist) stimulates a rise in serum ACTH and cortisol, suggesting that the HPA axis is under the tonic inhibitory control of endogenous opioids normalized in steady-state chronic methadone-maintained patients; their HPA axis responses to metyrapone-induced stress appear to be no different from that of healthy volunteer subjects [Kreek, 1973; Kreek et al., *Prolonged* (24 *hour*) *infusion of the opioid antagonist naloxone does not significantly alter plasma levels of cortisol and ACTH in humans. Proceedings of the 7th International Congress on Endocrinology* Elsevier Science, p. 1170, 1984].

Support for the effects of opioids on physiological functions regulated by the HPA and the HPG axes can be found in observations of heroin addicts. More specifically, it has been observed that many heroin addicts are infertile, and in the case of female addicts, their menstrual cycle is dramatically disrupted to the point that they do not ovulate. Furthermore, it has been observed that heroin addicts, and nonaddicted patients taking morphine, become constipated, and that the immune systems of addicts is weakened relative to the immune system of non addicts. However, once therapeutic agents designed to treat addiction, such as methadone, addicts become fertile, are no longer constipated, and have a immune system whose ability to fight foreign bodies is in parity with the immune system of a nonaddict.

Hence, what is needed is discovery of additional, heretofore unknown polymorphisms of the human mu opioid receptor gene that can be used as genetic markers to map the locus of the human mu opioid receptor gene in the genome.

What is also needed are the DNA sequences of heretofore unknown isolated nucleic acid molecules which encode human mu opioid receptors, wherein the DNA sequences include a combination of presently known and subsequently discovered polymorphisms of the human mu opioid receptors.

Furthermore, what is needed is the characterization of the binding properties of heretofore unknown human mu opioid receptors produced from the expression of genes comprising such heretofore unknown polymorphisms of the human mu opioid receptor gene, or combinations of unknown polymorphisms and known polymorphisms.

Furthermore, what is needed is a characterization of the activity of such unknown human mu opioid receptors produced from the expression of nucleic acid molecules comprising such polymorphisms.

What is also needed is a correlation between polymorphisms of the human mu opioid receptor gene, and the susceptibility of a subject to addictive diseases, such as heroin addiction, cocaine addiction, or alcohol addiction, to name only a few.

What is also needed are diagnostic methods to determine a subject's increased or decreased susceptibility to addictive diseases. With the results of such methods, targeted prevention methods, early therapeutic intervention, and improved chronic treatment to opioid addiction can be developed. Physicians armed with the results of such diagnostic methods can determine whether administration to a subject of opioid analgesics is appropriate or whether non-opioid derived analgesics should be administered to the subject. Also, appropriate choice and type of analgesic can be made in treating a subject's pain.

What is also need are methods of determining a subject's susceptibility to pain and responsibility to analgesics, and using that information when prescribing analgesics to the subject.

What is also needed is an ability to determine the binding affinity of the mu opioid receptor to endogenous opioids, such as β-endorphin, and the effect of this binding activity on the neuroendocrine system.

The citation of any reference herein should not be construed as an admission that such reference is available as "Prior Art" to the instant application.

SUMMARY OF THE INVENTION

There is provided, in accordance with the present invention, heretofore unknown polymorphisms of the human mu opioid receptor gene, and their use in mapping the locus of the human mu opioid receptor gene, determining susceptibility to addictive diseases, determining susceptibility to pain, and determining a therapeutically effective amount of pain reliever to administer to a subject suffering from pain, diagnosing a disease or disorder in a subject that is related to a physiological function regulated by the HPA or HPG axes of the neuroendocrine system, and selecting an appropriate therapeutic agent and a therapeutically effective amount of such an agent to administer to a subject suffering from a disease or disorder related to a physiological function regulated by the HPA or HPG.

Hence, the present invention extends to heretofore unknown polymorphisms of the human mu opioid receptor gene that can serve as genetic markers to map the locus of the human mu opioid receptor gene.

The present invention further extends to DNA sequences of heretofore unknown isolated nucleic acid molecules which encode human mu opioid receptors, wherein the DNA sequences include any combination of presently known polymorphisms and polymorphisms of the human mu opioid receptors discovered by Applicants.

The present invention further extends to the characterization of the binding properties of heretofore unknown human mu opioid receptors produced from the expression of isolated nucleic acid molecules comprising DNA sequences with such heretofore unknown polymorphisms of the human mu opioid receptor gene, or combinations of unknown polymorphisms and known polymorphisms.

The present invention further extends to Applicants' discovery that polymorphisms in an allele comprising a DNA sequence of SEQ ID NO:1, such as T67C, T124A, C153T, G174A, and the addition of GGC (a glycine codon) following position 187, hereinafter abbreviated as 187INS:GGC, which are described in further detail infra, are present in the population. The T67C polymorphism changes serine 23 to a proline (hereinafter abbreviated Ser23Pro), the T124A polymorphism changes serine 42 to a threonine (hereinafter abbreviated Ser42Thr), and the 187INS:GGC adds a glycine residue following glycine 63. The C153T and G174A are silent mutations in the coding region of the mu opioid receptor gene.

The present invention further extends to diagnostic methods to determine a subject's increased or decreased susceptibility to addictive diseases. With the results of such methods, targeted prevention methods, early therapeutic intervention, and improved chronic treatment to opioid addiction are set forth herein and encompassed by the present invention. In addition, attending medical professionals armed with the results of such diagnostic methods can determine whether administration of opioid analgesics is appropriate or whether non-opioid derived analgesics should be administered to the subject. Furthermore, appropriate choice and type of analgesic to treat a subject's pain can be made. Such determination may be made by identification of any individual or any combination of the above-mentioned polymorphisms, using such non-limiting methods as DNA sequencing, differential hybridization to biological chip arrays such as an oligonucleotide gelpad microchip, or single nucleotide extension (SNE) on chip arrays such as on oligonucleotide gelpad microchips.

Also, the present invention extends to methods of determining a subject's increased or decreased susceptibility to pain and response to analgesics, and the use of the information in prescribing analgesics to the subject.

In addition, the present invention extends to methods of diagnosing a disease or disorder in a subject, wherein the disease or disorder is related to a physiological function regulated by the HPA or HPG axes of the neuroendocrine system. Examples of such physiological functions include reproductive or sexual functions, gastrointestinal motility, immune response, and ability to withstand stress.

Broadly the present invention extends to an isolated variant allele of a human mu opioid receptor gene which can serve as a genetic marker, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A, C153T, G174A, or 187INS:GGC, or any combination thereof.

Furthermore, the present invention extends to an isolated variant allele of a human mu opioid receptor gene as set forth above, which is detectably labeled. Numerous detectable labels have applications in the present invention, such as radioactive elements, chemicals which fluoresces, or enzymes, to name only a few.

The present invention further extends to an isolated nucleic acid molecule selectively hybridizable to an isolated variant allele of the human mu opioid receptor gene, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A, C153T, G174A, or 187INS:GGC, or any combination thereof.

Moreover, the present invention extends to an isolated nucleic acid molecule selectively hybridizable to an isolated variant allele of the human mu opioid receptor gene, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A, C153T, G174A, or 187INS:GGC, or any combination thereof, wherein the isolated nucleic acid molecule is detectably labeled. Examples of detectable labels that have applications in this embodiment of the present invention are described above.

In addition, the present invention extends to an isolated variant allele of a human mu opioid receptor gene, wherein the predominant or "most common" allele of the human mu opioid receptor gene encodes a human mu opioid receptor comprising an amino acid sequence of SEQ ID NO:2, and the variant allele of the human mu opioid receptor gene encodes a variant human mu opioid receptor comprising an amino acid sequence having a variation in SEQ ID NO:2, wherein the variation comprises Ser23Pro, Ser42Thr or the addition of a Gly residue following Gly63, or the combination thereof.

Furthermore, the present invention extends to an isolated nucleic acid molecule selectively hybridizable to an isolated variant allele of a human mu opioid receptor gene of the present invention, wherein the isolated nucleic acid molecule encodes a variant human mu opioid receptor comprising an amino acid sequence having a variation in SEQ ID NO:2, wherein the variation comprises Ser23Pro, Ser42Thr or the addition of a Gly residue following Gly63, or the combination thereof.

Naturally, the present invention extends to a variant human mu opioid receptor comprising an amino acid sequence having a variation in SEQ ID NO:2, wherein the variation comprises Ser23Pro, Ser42Thr or the addition of a Gly residue following Gly63, or the combination thereof.

Furthermore, the present invention extends to an antibody having as immunogen a variant human mu opioid receptor comprising an amino acid sequence having a variation in SEQ ID NO:2, wherein the variation comprises Ser23Pro, Ser42Thr, or the addition of a Gly residue following Gly63, or both. Such an antibody can be a polyclonal antibody, a monoclonal antibody, or a chimeric antibody. Moreover, an antibody of the present invention can be detectably labeled. Examples of detectable labels which have applications in this embodiment comprises a radioactive element, a chemical which fluoresces, or an enzyme, to name only a few.

In addition, the present invention extends to cloning vectors that can be used to clone copies of a variant alleles of a human mu opioid receptor gene of the present invention. For example, the present invention extends to a cloning vector comprising an isolated variant allele of a human mu opioid receptor gene and an origin of replication, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A, C153T, G174A, or 187INS:GGC, or any combination thereof.

In another embodiment, the present invention extends to a cloning vector comprising an isolated nucleic acid molecule selectively hybridizable to an isolated variant allele of a human mu opioid receptor gene, and an origin of replication, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A, C153T, G174A, or 187INS:GGC, or any combination thereof.

Numerous cloning vectors have applications in the present invention. For example, a cloning vector having applications in the present invention includes *E. coli*, bacteriophages such as lambda derivatives, plasmids such as pBR322 derivatives, and pUC plasmid derivatives such as pGEX vectors or pmal-c or pFLAG, to name only a few.

Naturally, the present invention extends to expression vectors comprising an isolated variant allele a human mu opioid receptor gene operatively associated with a promoter, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises: T67C, T124A, C153T, G174A, or 187INS:GGC, or any combination thereof.

Furthermore, the present invention extends to an expression vector comprising an isolated nucleic acid molecule selectively hybridizable to an isolated variant allele a human mu opioid receptor gene, wherein the isolated nucleic acid molecule is operatively associated with a promoter. As set forth above, the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A, C153T, G174A, or 187INS:GGC, or any combination thereof.

Numerous promoters have applications in an expression vector of the present invention, including but not limited to immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the tip system, the TAC system, the TRC system, the major operator and promoter regions of phage lambda, control regions of fd coat protein, 3-phosphoglycerate kinase promoter, acid phosphatase promoter, or promoters of yeast α mating factor, to name only a few.

In addition, the present invention extends to a unicellular host transformed or transfected with an expression vector of the present invention. Examples of hosts which can be transformed or transfected with an expression vector of the present invention, and have applications in the present invention, include, but are not limited to, *E. coli, Pseudomonas, Bacillus, Streptomyces*, yeast, CHO, R1.1, B-W, L-M, COS1, COS7, BSC1, BSC40, BMT10 or Sf9 cells.

Naturally, the present invention extends to a method of producing a variant human mu opioid receptor comprising an amino acid sequence having a variation in SEQ ID NO:2, wherein the variation comprises Ser23Pro, Ser42Thr, or the addition of a Gly residue following Gly63, or the combination thereof. An example of such a method comprises the steps of culturing a unicellular host transformed or transfected with an expression vector comprising an isolated variant allele a human mu opioid receptor gene, wherein the predominant or "most common" allele of a human mu opioid receptor gene found in the population comprises a DNA sequence of SEQ ID NO:1, and a variant allele of the present invention comprises a DNA sequence having a variation in SEQ ID NO:1, wherein the variation comprises T67C, T124A or 187INS:GGC, or the combination thereof, operatively associated with a promoter. The transformed or transfected unicellular host is then cultured under conditions that provide for expression of the variant allele of the human mu opioid receptor gene. The variant human mu opioid receptor produced from such induced expression is then recovered from the unicellular host.

Another example comprises the steps of culturing a unicellular host transformed or transfected with an expression vector comprising an isolated nucleic acid molecule operatively associated with a promoter, wherein the isolated nucleic acid molecule is selectively hybridizable to a variant allele a human mu opioid receptor gene, and the predominant or "most common" allele of a human mu opioid receptor gene found in the population comprises a DNA sequence of SEQ ID NO:1, and the variant allele comprises a DNA sequence having at least one variation in SEQ ID NO:1, wherein the at least one variation comprises T67C, T124A or 187INS:GGC, or the combination thereof. The transformed or transfected unicellular host is then cultured under conditions that provide for expression of the variant allele of the human mu opioid receptor gene. The variant human opioid receptor produced from such induced expression is then recovered from the unicellular host.

The invention further extends to altered expression of the mu opioid gene product, and means for detecting the altered expression, as a consequence of the presence of the silent mutations C153T or G174A, or the combination of either or both of the foregoing with any of the other polymorphisms hereindescribed.

Furthermore, the present invention extends to an isolated variant allele of a human mu opioid receptor gene, wherein the predominant or "most common" allele of the human mu opioid receptor gene comprises a DNA sequence of SEQ ID NO:1, and a variant allele of the present invention comprises a DNA sequence having at least two variations in SEQ ID NO:1, wherein at least one of the variations is T67C, T124A, C153T, G174A, or 187INS:GGC. The other variation may be any at least one of those described herein or at least one known in the art, such as but not limited to A118G, C17T, G24A, G779A, or G942A.

The present invention further extends to an isolated variant allele of a human mu opioid receptor gone comprising a DNA sequence having at least two variations in SEQ ID NO:1, as stated above, which is detectably labeled. Examples of detectable labels having applications in this embodiment include, but are not limited to, a radioactive element, a chemical which fluoresces, or an enzyme.

The present invention further extends to an isolated nucleic acid molecule selectively hybridizable to an isolated variant allele of a human mu opioid receptor gene, wherein the predominant or "most common" allele of the human mu opioid receptor gene comprises a DNA sequence of SEQ ID NO:1, and a variant allele of the present invention comprises a DNA sequence having at least two variations in SEQ ID NO:1, wherein at least one of the variations is T67C, T124A, C153T, G174A, or 187INS:GGC, and the other variation may be any at least one of those described herein or at least one known in the art, such as but not limited to A118G, C17T, G24A, G779A, or G942A.

Naturally, the present invention extends to a detectably labeled isolated nucleic acid molecule selectively hybridizable to an isolated variant allele of a human mu opioid receptor comprising a DNA sequence having at least two variations in SEQ ID NO:1, wherein at least one of the variations is T67C, T124A, C153T, G174A, or 187INS:GGC, and the other variation may be at least one of those described herein or at least one known in the art, such as but not limited to A118G, C17T, G24A, G779A, or G942A.

Examples of detectable labels having applications in this embodiment of the invention include, but are not limited to, a radioactive element, a chemical which fluoresces, or an enzyme.

Furthermore, the present invention extends to an isolated variant allele of a human mu opioid receptor gene comprising a DNA sequence having at least two variations in SEQ ID NO:1, as set forth above, wherein the predominant or "most common" allele of a human mu opioid receptor gene encodes a human mu opioid receptor comprising an amino acid sequence of SEQ ID NO:2, and a variant allele of the present invention encodes a human mu opioid receptor comprising an amino acid having at least two variations in SEQ ID NO:2, wherein the variations comprise Ser23Pro, Ser42Thr or the addition of a Gly residue following Gly63, or both, or at least one of the foregoing or at least one known in the art, such as but not limited to Asn40Asp, Ala6Val, or Arg260His.

The present invention further extends to an isolated nucleic acid molecule selectively hybridizable to an isolated variant allele of a human mu opioid receptor gene comprising a DNA sequence having at least two variations in SEQ ID NO:1, wherein the variations comprise T67C, T124A, C153T, G174A, or 187INS:GGC, wherein at least one of the variations is T67C, T124A, C153T, G174A, or 187INS:GGC, and the other variation may be any at least one of those described herein or at least one known in the art, such as but not limited to A118G, C17T, G24A, G779A, or G942A, such that the isolated nucleic acid molecule encodes a variant human mu opioid receptor comprising an amino acid sequence having at least two variations in SEQ ID NO:2, wherein the variations comprise at least one of Ser23Pro or conserved variants thereof, Ser42Thr or conserved variants thereof or the addition of a Gly residue following Gly63 or conserved variants thereof, and the other being at least the other of the foregoing or at least one variant known in the art, such as but not limited to Asn40Asp, Ala6Val, or Arg260His.

Naturally, the present invention extends to a variant human mu opioid receptor comprising an amino acid sequence having at least one variation in SEQ ID NO:2, wherein the variations comprise:
  Ser23Pro or conserved variants thereof;
  Ser42Thr or conserved variants thereof;
  or the addition of a Gly residue following Gly63 or conserved variants thereof.

Moreover, the present invention extends to an antibody having as an immunogen a human mu opioid receptor comprising an amino acid sequence having at least two variations in SEQ ID NO:2, wherein the variations comprise at least one of Ser23Pro or conserved variants thereof, Ser42Thr or conserved variants thereof or the addition of a Gly residue following Gly63 or conserved variants thereof, and the at least one other being at least one of the other of the foregoing or at least one variant known in the art, such as but not limited to Asn40Asp, Ala6Val, or Arg260His.

An antibody of the present invention can be a polyclonal antibody, a monoclonal antibody, or a chimeric antibody. Moreover, an antibody of the present invention can be detectably labeled. Examples of detectable labels having applications in an antibody of the present invention include, but are not limited to, a radioactive element, a chemical which fluoresces, or an enzyme.

Furthermore, the present invention extends to a cloning vector comprising an isolated variant allele of a human mu opioid receptor gene and an origin of replication, wherein the predominant or "most common" allele of the human mu opioid receptor gene present in the population comprises a DNA sequence of SEQ ID NO:1, and a variant allele of the present invention comprises a DNA sequence having at least two variations in SEQ ID NO:1, wherein at least one the variations is T67C, T124A; C153T; G174A or 187INS: GGC, and the at least one other being one other of the foregoing or at least one known in the art, such as but not limited to A118G, C17T, G24A, G779A, or G942A.

In addition, the present invention extends to a cloning vector comprising an isolated nucleic acid molecule selectively hybridizable to a variant allele of a human mu opioid receptor and an origin of replication, wherein the variant allele comprises a DNA sequence having at least two variations in SEQ ID NO:1, wherein at least one the variations is T67C, T124A; C153T; G174A or 187INS:GGC, and the at least one other being one other of the foregoing or at least one known in the art, such as but not limited to A118G, C17T, G24A, G779A, or G942A; and an origin of replication.

Numerous cloning vectors have applications in this embodiment of the present invention. Examples of such vectors include, but are not limited to, E. coli, bacteriophages, such as lambda derivatives, plasmids such as pBR322 derivatives, and pUC plasmid derivatives such as pGEX vectors or pmal-c or pFLAG, to name only a few.

Naturally, the present invention extends to an expression vector comprising an isolated variant allele of a human mu opioid receptor gene operatively associated with a promoter, wherein such an isolated variant allele comprises a DNA sequence having at least two variations in SEQ ID NO:1, wherein at least one the variations is T67C; T124A; C153T; G174A or 187INS:GGC, and the at least one other being one other of the foregoing or at least one variant known in the art, such as but not limited to A118G, C17T, G24A, G779A, or G942A.

In addition, the present invention extends to an expression vector comprising an isolated nucleic acid molecule operatively associated with a promoter, wherein the isolated nucleic acid molecule is selectively hybridizable to an isolated variant allele of a human mu opioid receptor gene comprising a DNA sequence having at least two variations in SEQ ID NO:1, wherein at least one the variations is T67C; T124A; C153T; G174A or 187INS:GGC, and the at least one other variation being one other of the foregoing or at least one variant known in the art, such as but not limited to A118G, C17T, G24A, G779A, or G942A.

Numerous promoters are available and have applications in an expression vector of the present invention. Examples of promoters having applications include, but are not limited to immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac the tip system, the TAC system, the TRC system, the major operator and promoter regions of phage lambda, control regions of fd coat protein, 3-phosphoglycerate kinase promoter, acid phosphatase promoter, or promoters of yeast a mating factor, to name only a few.

Naturally, the present invention extends to a unicellular host transformed or transfected with an expression vector of the present invention. Examples of unicellular hosts having applications in an embodiment of the present invention include, but are not limited to, E. coli, Pseudonomas, Bacillus, Streptomyces, yeast, WHO, R1.1, B-W, L-M, COS1, COS7, BSC1, BSC40, BMT10 or Sf9 cells.

In another embodiment, the present invention extends to a method for producing a human mu opioid receptor comprising an amino acid sequence having at least two variations in SEQ ID NO:2, wherein the variations comprise at least one of Ser23Pro or conserved variants thereof, Ser42Thr or conserved variants thereof or the addition of a Gly residue following Gly63, or conserved variants thereof; and the at least one other being the other of the foregoing or at least one variant known in the art, such as but not limited to Asn40Asp, Ala6Val, or Arg260His.

More specifically, an example of a method for producing such a human mu opioid receptor comprises the steps of culturing a unicellular host transformed or transfected with an expression vector comprising an isolated variant allele of a human mu opioid receptor gene operatively associated with a promoter, wherein the variant allele comprises a DNA sequence having at least two variations in SEQ ID NO:1, wherein at least one the variations is T67C; T124A; C153T; G174A or 187INS:GGC, and the at least one other variation being one other of the foregoing or at least one variant known in the art, such as but not limited to A118G, C17T, G24A, G779A, or G942A; under conditions that provide for expression of the isolated variant allele of a human mu opioid receptor gene. After expression, a variant human mu opioid receptor is recovered from the unicellular host.

In another example, a method for producing a human mu opioid receptor of the present invention comprises the steps of culturing a unicellular host transformed or transfected with an expression vector comprising an isolated nucleic acid molecule operatively associated with a promoter, wherein the isolated nucleic acid molecule is selectively hybridizable to an isolated variant allele of a human mu opioid receptor gene comprising a DNA sequence having at least two variations in SEQ ID NO:1, wherein at least one the variations is T67C; T124A; C153T; G174A or 187INS: GGC, and the at least one other variation being one other of the foregoing or at least one variant known in the art, such as but not limited to A118G, C17T, G24A, G779A, or G942A, under conditions that provide for expression of the isolated nucleic acid molecule. The variant human mu opioid receptor produced from the expression is then recovered from the unicellular host.

The present invention also embraces functional variants of the mu opioid receptor as a consequence of the presence of at least one of the polymorphisms described herein, either as the only polymorphism as compared to the wild-type gene or in combination with any number of other polymorphisms, including the others described herein or those known in the art. The invention is further directed to methods for detecting altered gene product structure, activity or function, said altered structure, activity or function resulting from the presence of at least one of the polymorphisms described herein.

Accordingly, the present invention extends to a method for determining a susceptibility in a subject to at least one addictive disease, comprising the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises: T67C; T124A; or 187INS:GGC.

The present of at least one of these variations in the human mu opioid receptor gene of the first allele is expected to be indicative of the subject's susceptibility to at least one addictive disease relative to the susceptibility of a standard to at least one addictive disease, wherein the standard comprises a first allele comprising a human mu opioid receptor gene having a DNA sequence of SEQ ID NO:1.

Another embodiment of the method for determining a susceptibility in the subject to at least one addictive disease, as described above, comprises the further step of determining whether the second allele of the bodily sample of the subject comprises a human mu opioid receptor gene comprising a DNA sequence having at least one variation in SEQ ID NO:1, wherein the variations comprise T67C, T124A or 187INS:GGC.

The presence of at least one variation the second allele of the bodily sample is expected to be indicative of the subject's susceptibility to at least one addictive disease relative to a standard in which both alleles of a human mu opioid receptor gene comprise a DNA sequence of SEQ ID NO:1.

In another embodiment, the present invention extends to a method for determining a susceptibility to at least one addictive disease in a subject relative to susceptibility to at least one addictive disease in a standard, involving the detection of variations in the human mu opioid receptor itself, and particularly, determining whether a variant human mu opioid receptor is present in a bodily sample from a subject. Such a method comprises the steps of removing a bodily sample comprising a human mu opioid receptor from the subject, and determining whether the human mu opioid receptor present in the sample is a variant human mu opioid receptor of the invention, wherein the variant human mu opioid receptor comprises an amino acid sequence having at least one variation in SEQ ID NO:2, wherein the at least one variation comprises: Ser23Pro, Ser42Thr or conserved variants thereof; or the addition of a Gly residue following Gly63 or conserved variants thereof, the presence of at least one variation is expected to be indicative of the subject's susceptibility to at least one addictive disease relative to susceptibility to at least one addictive disease in a standard, wherein the human mu opioid receptor of the standard comprises an amino acid sequence of SEQ ID NO:2.

As explained above, at least one addictive disease includes, but is not limited to, opioid addiction, cocaine addiction or addiction to other psychostimulants, nicotine addiction, barbiturate or sedative hypnotic addiction, anxiolytic addiction, or alcohol addiction.

Furthermore, the present invention extends to a method for determining a susceptibility to pain in a subject relative to susceptibility to pain in a standard, comprising the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises: T67C, T124A or 187INS:GGC. The presence of at least one variation in the human mu opioid receptor gene of the first allele is expected to be indicative of a decreased or increased susceptibility to pain in the subject relative to susceptibility to pain in the standard, wherein the first allele of the standard comprises a human mu opioid receptor gene comprising a DNA sequence of SEQ ID NO:1.

Moreover, a method for determining a susceptibility to pain in a subject may further comprise the step of determining whether the second allele comprises a human mu opioid receptor gene comprising a DNA sequence having at least one variation in SEQ ID NO:1, wherein the variation comprises: T67C, T124A or 187INS:GGC. The presence of the at least one variation in the human mu opioid receptor gene of the second allele of the bodily sample from the subject is expected to be indicative of an increased or decreased susceptibility to pain in the subject relative to the susceptibility to pain in the standard, wherein the second allele in the standard comprises a human mu opioid receptor gene comprising a DNA sequence of SEQ ID NO:1.

In another embodiment, the present invention extends to a method for determining a susceptibility to pain in a subject relative to susceptibility to pain in a standard by examining a bodily sample taken from the subject for the presence of a variant human mu opioid receptor. Such a method comprises the steps of removing a bodily sample comprising a human mu opioid receptor from the subject, and determining whether the human mu opioid receptor present in the sample is a variant human mu opioid receptor of the invention, i.e., comprises an amino acid sequence having at least one variation in SEQ ID NO:2, wherein the variation comprises:

Ser23Pro or conserved variants thereof;

Ser42Thr or conserved variants thereof; or addition of a Gly residue following Gly63 or conserved variants thereof, such that the presence of at least one variation is expected to be indicative of the subject's susceptibility to pain relative to susceptibility to pain in the standard, wherein the human mu opioid receptor of the standard comprises an amino acid sequence of SEQ ID NO:2.

Once a susceptibility to pain in the subject has been determined, it is possible for attending medical professionals treating the subject to administer to an appropriate, or therapeutically effective amount of pain reliever in order to induce analgesia in the subject. Administration of such an amount is important to the subject because, should an inappropriate amount of pain reliever be administered, the subject may not experience analgesia, and may be exposed to potentially deleterious side effects of the pain reliever, such as induction of addiction to the pain reliever, brain damage, or death.

Consequently, the present invention extends to a method for determining a therapeutically effective amount of pain reliever to administer to a subject in order to induce analgesia in the subject relative to a therapeutically effective amount of the pain reliever to administer to a standard in order to induce analgesia in the standard, wherein the method comprises determining a susceptibility to pain in the subject relative to susceptibility to pain in the standard. The susceptibility of pain in the subject is expected to be indicative of the therapeutically effective amount of the pain reliever to administer to the subject to induce analgesia in the subject relative to the amount of the pain reliever to administer to the standard to induce analgesia in the standard.

Hence, the present invention extends to a method for determining a therapeutically effective amount of pain reliever to administer to a subject in order to induce analgesia in the subject relative to a therapeutically effective amount of the pain reliever to administer to a standard in order to induce analgesia in the standard wherein the method comprises the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the at least one variation comprises: T67C, T124A or 187INS:GGC. The presence of at least one variation in the human mu opioid receptor gene of the first allele from the bodily sample is expected to be indicative of the therapeutically effective amount of pain reliever to administer to the subject to induce analgesia in the subject relative to the therapeutically effective amount of pain reliever to administer to the standard to induce analgesia in the standard, wherein the standard comprises a first allele comprising a human mu opioid receptor gene comprising a DNA sequence of SEQ ID NO:1.

Moreover, the present invention further extends to a method for determining a therapeutically effective amount of pain reliever to administer to a subject in order to induce analgesia in the subject relative to a therapeutically effective amount of pain reliever to administer to a standard to induce analgesia therein, further comprising the steps of removing a bodily sample comprising a first and second allele comprising a human mu opioid receptor gene from the subject, and determining whether the second allele of the bodily sample comprises a human mu opioid receptor gene comprising a DNA sequence comprising at least one variation in SEQ ID NO:1, wherein the at least one variation comprises: T67C, T124A or 187INS:GGC. The presence of at least one variation in the human mu opioid receptor gene of the first and/or second allele of the bodily sample is expected to be indicative of the therapeutically effective amount of pain reliever to administer to the subject to induce analgesia therein relative to the amount of pain reliever to administer to a standard to induce analgesia therein, wherein the first and second alleles of the standard comprise a human mu opioid receptor gene comprising a DNA sequence of SEQ ID NO:1.

In another embodiment, the present invention extends to determining a therapeutically effective amount of pain reliever to administer to a subject in order to induce analgesia in the subject, by examining a bodily sample from a subject for the presence of a variant human mu opioid receptor comprising an amino acid sequence having a variation in SEQ ID NO:2. More specifically, the present invention extends to a method for determining a therapeutically effective amount of pain reliever to administer to a subject in order to induce analgesia in the subject, relative to a therapeutically effective amount of pain reliever to administer to a standard in order to induce analgesia in the standard, comprising the steps of removing a bodily sample comprising a human mu opioid receptor from the subject, and determining whether the human mu opioid receptor present in the sample comprises an amino acid sequence having at least one variation in SEQ ID NO:2, wherein the variation comprises:

Ser23Pro or conserved variants thereof;

Ser42Thr or conserved variants thereof; or addition of a Gly residue following Gly63 or conserved variants thereof, such that the presence of at least one variation is expected to be indicative of the therapeutically effective amount of pain reliever to administer to the subject to induce analgesia therein relative to the therapeutically effective amount of pain reliever to administer to induce analgesia in the standard, wherein the human mu opioid receptor of the standard comprises an amino acid sequence of SEQ ID NO:2.

Examples of pain relievers having applications in this embodiment of the present invention include, but are not limited to, morphine, codeine, dihydromorphin, meperidine, methadone, fentanyl and its congeners, butorphenol, nalbuphine, LAAM, or propoxyphine, to name only a few.

Furthermore, the present invention extends to a method for determining a therapeutically effective amount of a therapeutic agent for treating at least one addictive disease to administer to a subject suffering from at least one addictive disease, relative to a therapeutically effective amount of the therapeutic agent to administer to a standard suffering from the at least one addictive disease. As a result, the dosage of therapeutic agent administered to an addict can be "tailored" to the addict's needs based upon the addict's genotype. An example of such a method comprises the steps of removing a bodily sample from the subject, wherein the bodily sample comprises a first and second allele of the human mu opioid receptor gene, and determining whether the first allele comprises a DNA sequence having at least one variation in SEQ ID NO:1, wherein the variation comprises: T67C, T124A or 187INS:GGC. The presence of the at least one variation in the human mu opioid receptor gene of the first allele in the bodily sample from the subject is related to the therapeutically effective amount of therapeutic agent to administer to the subject to treat the subject's at least one addictive disease, relative to the therapeutically effective amount of the therapeutic agent to administer to the standard suffering from the at least one addictive disease, wherein the first and second allele of the standard comprise a human mu opioid receptor gene comprising a DNA sequence of SEQ ID NO:1.

Furthermore, a method for determining a therapeutically effective amount of therapeutic agent to administer to a subject suffering from at least one addictive disease may further comprise an additional step of determining whether the second allele of the bodily sample taken from the subject comprises a human mu opioid receptor gene comprises a DNA sequence having at least one variation in SEQ ID NO:1, wherein the at least one variation comprises: T67C, T124A or 187INS:GGC. Such a variation in the first and/or second allele of the bodily sample is expected to be indicative of the therapeutically effective amount of the therapeutic agent to administer to the subject to treat the at least one addictive disease of the subject relative to the therapeutically effective amount of the therapeutic agent to administer to the standard suffering from the at least one addictive disease.

In another embodiment, the present invention extends to determining a therapeutically effective amount of a therapeutic agent for treating at least one addictive disease to administer to a subject suffering from at least one addictive disease by examining a bodily sample from a subject for the presence of a variant human mu opioid receptor comprising an amino acid sequence having at least one variation in SEQ ID NO:2. More specifically, the present invention extends to a method for determining a therapeutically effective amount of therapeutic agent for treating at least one addictive disease to administer to a subject suffering from the at least one addictive disease, relative to a therapeutically effective amount of the therapeutic agent to administer to a standard suffering from the at least one addictive disease, wherein the method comprises the steps of removing a bodily sample comprising a human mu opioid receptor from the subject, and determining whether the human mu opioid receptor present in the sample comprises an amino acid sequence having at least one variation in SEQ ID NO:2, wherein the variation comprises:

Ser23Pro or conserved variants thereof;
Ser42Thr or conserved variants thereof; or
addition of a Gly residue following Gly63 or conserved variants thereof.

The presence of at least one variation in the human mu opioid receptor of the bodily sample is expected to be indicative of therapeutically effective amount of the therapeutic agent to administer to the subject to treat the at least one addictive disease of the subject relative to the therapeutically effective amount of the therapeutic agent to administer to the standard suffering from the at least one addictive disease, wherein the human mu opioid receptor of the standard comprises an amino acid sequence of SEQ ID NO:2.

Examples of at least one addictive disease includes, but is not limited to opioid addiction, cocaine addiction or addiction to other psychostimulants, nicotine addiction, barbiturate or sedative hypnotic addiction, anxiolytic addiction, or alcohol addiction. Furthermore, examples of therapeutic agents having applications of the present invention include methadone, LAAM, maltrexone, or buprinorphine, to name only a few.

Furthermore, the present invention extends to a method for diagnosing a disease or disorder related to a physiological function regulated by the HPA or HPG axes of the neuroendocrine system. The HPA and HPG axes play an important role in regulation of numerous physiological activities such as reproductive and sexual function, gastrointestinal motility, immune response to an antigen, or an ability to withstand stress. Furthermore, the HPA and HPG axes exert such regulatory control via the production of endogenous opioids that interact with opioid in many locations of the body. In particular, in the HPG axis, the mu opioid receptor is centrally involved in tonic regulation of the luteinizing hormone, particularly in its pulsatile release. Furthermore, in the HPA axis, the mu opioid receptor modulates corticotropin releasing factor/hormone (CRF or CRH) in the hypothalamus which in turn modulates production of pro-opiomelanocortin (POMC) in the pituitary which is processed into several active peptides such as ACTH, which stimulates the adrenal cortex to release the stress hormone cortisol in humans, which in turn provides the stress response to environmental stimuli. Furthermore, modulated mu opioid receptor activity can lead to modulation of most cellular and humoral immunity including that mediate through T cells, B cells, cytokines, and chemokines. The pathophysiology of immune disorders may therefore be influenced by pharmacotherapies that modulate the activity of the mu opioid receptor. Moreover, gastrointestinal motility is modulated by modulation of opioid receptor treatment, and diagnosis of a disease or disorder related to gastrointestinal motility (e.g. constipation) may be facilitated by knowledge of intrinsic mu opioid receptor motility.

Applicants have discovered that the binding affinity of an opioid receptor, such as a mu opioid receptor with an endogenous opioid ligand, such as β-endorphin, is expected to modulate such physiological activities. Hence, the binding affinity of variant mu opioid receptors for endogenous opioid ligands such as β-endorphin, is expected to modulate those physiological activities regulated by the HPA and HPG axes relative to those physiological activities in a standard having mu opioid receptors produced from the predominant or "most common" allele of the mu opioid receptor gene comprising a DNA sequence of SEQ ID NO:1. As the result, the present invention extends to a method of diagnosing a disease or disorder related to a physiological function regulated by the HPA or HPG axes. Examples of physiological functions regulated by the HPA and the HPG include, but are not limited to sexual or reproductive functions, gastrointestinal motility, immune response, or ability to withstand stress. Such a method comprises the steps of removing a bodily sample comprising a first and second allele of a human mu opioid receptor gene from the subject, and determining whether the first allele comprises a human mu opioid receptor gene comprising a DNA sequence having at least one variation in SEQ ID NO:1, wherein the variation comprises: T67C, T124A or 187INS:GGC.

The presence of at least one variation in the human mu opioid receptor gene of the first allele is expected to be indicative of a disorder related to a physiological function regulated by the HPA or GPA, such as sexual or reproductive functions, gastrointestinal motility, immune response, and the ability to withstand stress, wherein the first allele of the standard comprises a human mu opioid receptor gene comprising a DNA sequence of SEQ ID NO:1.

Moreover, a method for diagnosing a disease or disorder related to a physiological function regulated by the HPA or GPA, as described above may further comprise the step of determining whether the second allele of the bodily sample comprises a human mu opioid receptor gene comprising a DNA sequence having at least one variation in SEQ ID NO:1, wherein the variation comprises: T67C, T124A or 187INS:GGC. The presence of the at least one variation in the human mu opioid receptor gene of the second allele of the bodily sample from the subject may be expected to be indicative of a disease or disorder related to sexual and reproductive functions, gastrointestinal motility, immune response, or the ability of the subject to withstand stress.

In another embodiment, the present invention extends to a method for diagnosing a disease or disorder related to a physiological function regulated by the HPA or GPA by examining a bodily sample taken from the subject for the presence of a variant human mu opioid receptor. Such a method comprises the steps of removing a bodily sample comprising a human mu opioid receptor from the subject, and determining whether the human mu opioid receptor present in the sample is a variant human mu opioid receptor of the invention, i.e., comprises an amino acid sequence having at least one variation in SEQ ID NO:2, wherein the variation comprises:

Ser23Pro or conserved variants thereof;
Ser42Thr or conserved variants thereof; or
addition of a Gly residue following Gly63 or conserved variants thereof, such that the presence of at least one variation is expected to be indicative of a disease or disorder related to a physiological activity regulated by the HPA or HPG axes, such as sexual function or development, gastric motility, immune response, or the ability of the subject to withstand stress, relative to regulation of such activities in a standard comprising a human mu opioid receptor having an amino acid sequence of SEQ ID NO:2.

Once a disease or disorder related to a physiological function regulated by the HPA or HPG axes has been diagnosed, it is possible for attending medical professionals treating the subject to select and administer an appropriate therapeutic agent and a therapeutically effective amount of the agent to administer to the subject to treat such a disease or disorder. Consequently, the present invention extends to a method for determining an appropriate therapeutic agent to administer to a subject suffering from a disease or disorder related to a physiological function regulated by the HPA or HPG axes, comprising removing a bodily sample from the subject, and determining the presence of at least one variant allele of a mu opioid receptor gene in the bodily sample, wherein the variant allele comprises a human mu opioid receptor gene comprising a DNA sequence having at least one variation in SEQ ID NO:1, wherein the variation comprises: T67C, T124A or 187INS:GGC.

The present invention further extends to a method for selecting an appropriate therapeutic agent to administer to a subject suffering from a disease or disorder related to a physiological function regulated by the HPA or HPG axes as set forth above, further comprising determining whether the bodily sample comprises a second variant allele of the mu opioid receptor gene comprising a DNA sequence having a variation in SEQ ID NO:1, wherein the variation comprises: T67C, T124A or 187INS:GGC.

The present invention further extends to commercial test kits suitable for use by a medical professional to determine whether either or both alleles of a bodily sample taken from a subject comprise a DNA sequence having at least one variation in SEQ ID NO:1, wherein the variation comprises: T67C, T124A or 187INS:GGC.

Commercial test kits of the present invention have applications in determining susceptibility of pain in the subject relative to a standard. Such kits can also be used to determine a subject's increased or decreased susceptibility to at least one addictive disease relative to susceptibility to at least one addictive disease in a standard. Also a therapeutically effective amount of pain reliever to administer to the subject in order to induce analgesia in the subject relative to a therapeutically effective amount of pain reliever to administer to a standard to induce analgesia in the standard can be determined. Moreover, a test kit of the present invention has applications in determining a therapeutically effective amount of therapeutic agent for treating at least one addictive disease to administer to a subject suffering from the at least one addictive disease, relative to a therapeutically effective amount of therapeutic agent to administer to a standard suffering from at least one addictive disease. Furthermore, test kits of the invention have applications in diagnosing a disease or disorder related to a physiological condition regulated by the HPA or HPG axes of the neuroendocrine system, and in selecting an appropriate therapeutic agent for treating such a disease or disorder, along with a therapeutically effective amount of agent to administer to the subject. A standard as used herein comprises two alleles of a human mu opioid receptor gene comprising a DNA sequence of SEQ ID NO:1.

Furthermore, a commercial test kit of the present invention can also be used to determine the presence of an isolated variant allele of a human mu opioid receptor gene of the present invention in a bodily sample removed from a subject, which can serve as a genetic marker. As explained above, the predominant or "most common" allele of a human mu opioid receptor gene found in the population comprises a DNA sequence of SEQ ID NO:1. Hence a variant allele comprising a DNA sequence having a variation in SEQ ID NO:1, wherein the variation comprises:

T67C; T124A; C153T; G174A or 187INSGGC, or combinations thereof, can be detected in the bodily sample with a commercial kit of the invention.

Other variant alleles of the human mu opioid receptor gene of the present invention can be detected with a commercial test kit of the present invention. For example, an isolated variant allele of a human mu opioid receptor gene detectable with a commercial kit of the present invention, comprises a DNA sequence having at least two variations in SEQ ID NO:1, wherein the variations comprise:

T67C; T124A; C153T; G174A or 187INS:GGC.

Accordingly, a commercial test kit may be prepared for determining the presence of at least one variation in a human mu opioid receptor gene of either or both alleles in a bodily sample taken from a subject, wherein the commercial test kit comprises:

a) PCR oligonucleotide primers suitable for detection of an allele comprising a human mu opioid receptor gene having a DNA sequence with a variation in SEQ ID NO:1;

b) other reagents; and c) directions for use of the kit.

The present invention further extends to commercial test kits capable of detecting a variant human mu opioid receptor in a bodily sample taken from a subject. Examples of variant human mu opioid receptors that can be detected with a kit of the present invention comprise a variant human mu opioid receptor comprising an amino acid sequence having a variation in SEQ ID NO:2, wherein the variation comprises Ser23Pro or conserved variants thereof; Ser42Thr or conserved variants thereof; or a variant human mu opioid receptor comprising an amino acid sequence having at least two variations in SEQ ID NO:2, wherein the variations comprise at least one of:

Ser23Pro or conserved variants thereof;

Ser42Thr or conserved variants thereof; or addition of a Gly residue or conserved variants thereof.

Moreover, a commercial test kit of the present invention can be used to determine: susceptibility to pain in the subject relative to susceptibility to pain in a standard; a therapeutically effective amount of pain reliever to administer to a subject to induce analgesia in the subject relative to a therapeutically effective amount of pain reliever to administer to a standard to induce analgesia in the standard; a therapeutically effective amount of therapeutic agent for treating at least one addictive disease to administer to a subject suffering from at least one addictive disease, relative to a therapeutically effective amount of therapeutic agent to administer to a standard suffering from the at least one addictive disease; diagnosing a disease or disorder related to a physiological condition regulated by the HPA or HPG axes of the neuroendocrine system, or selecting an appropriate therapeutic agent for treating such a disease or disorder, along with a therapeutically effective amount of such agent to administer to the subject.

Accordingly, the present invention extends to a commercial test kit having applications set forth above, comprising a predetermined amount of at least one detectably labeled immunochemically reactive component having affinity for a variant human mu opioid receptor;

(b) other reagents; and (c) directions for use of the kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the human mu opioid receptor of a bodily sample to a detectable label;
(b) one or more additional immunochemical reagents of which at least one reagent is a ligand or an immobilized ligand, which ligand comprises:
   (i) a ligand capable of binding with the labeled component (a);
   (ii) a ligand capable of binding with a binding partner of the labeled component (a);
   (iii) a ligand capable of binding with at least one of the component(s) to be determined; or
   (iv) a ligand capable of binding with at least one of the binding partners of at least one of the component(s) to be determined; or
(c) directions for the performance of a protocol for the detection and/or determination of one or more components of an immunochemical reaction between the human mu opioid receptor gene of the present invention and a specific binding partner thereto.

Accordingly, it is an object of the present invention to provide heretofore unknown variations the DNA sequence of the human mu opioid receptor gene wherein the variations can be used to map the locus of the human mu opioid receptor gene.

It is yet another object of the present invention to use heretofore unknown polymorphisms of an allele of the human mu opioid receptor gene as markers for any kind of disorder related to the human mu opioid receptor, such as an addictive disease, pain, or markers for genes.

It is another object of the present invention to provide nucleotides, optionally detectably labeled, selectively hybridizable to variant alleles of the human mu opioid receptor gene disclosed herein, as well as polypeptides produced from the expression of the variant alleles and nucleotides selectively hybridizable thereto under selective hybridization conditions.

It is yet another object of the present invention to provide antibodies, optionally detectably labeled, having immunogens comprising polypeptides produced from the expression of variant alleles of human mu opioid receptor gene, or expression of isolated nucleic acid molecules selectively hybridizable to variant alleles disclosed herein.

It is another object of the present invention to gain insight into a subject's susceptibility to pain. This insight can be used to determine a therapeutically effective dose of pain reliever to administer to the subject to induce analgesia therein relative to the therapeutically effective amount of pain reliever administered to a standard to induce analgesia therein, wherein the standard comprises two alleles of the human mu opioid receptor gene comprising a DNA sequence of SEQ ID NO:1, or a variant human mu opioid receptor comprising an amino acid sequence of SEQ ID NO:2.

Such information can be used to tailor a regimen for treating a subject suffering from at least one addictive disease, relative to the therapeutically effective amount of therapeutic agent administered to a standard suffering from at least one addictive disease.

It is yet another object of the present invention to provide commercial test kits for attending medical professionals to determine the presence of variant alleles of a human mu opioid receptor gene in a bodily sample taken from a subject. The results of such testing can then be used to determine the subject's susceptibility to pain, susceptibility to at least one addictive disease, determining a therapeutically effective amount of pain reliever to administer to the subject in order to induce analgesia, or determining a therapeutically effective amount of therapeutic agent for treating at least one addictive disease to administer to the subject.

It is an object of the present invention to determine the activity of a mu opioid receptor in a subject, and use such information to diagnose a disease or disorder related to sexual or reproductive function, gastrointestinal motility, immune response, or ability to withstand stress, wherein variant alleles of the mu opioid receptor gene when expressed produce variant mu opioid receptors having activity different from a mu opioid receptor produced from the predominant or "most common" allele of the mu opioid receptor comprising a DNA sequence of SEQ ID NO:1.

It is another object of the present invention to employ Applicants' discovery of a correlation between the activity of a mu opioid and its impact the neuroendocrine system, and particularly on levels of hormones within the body. As a result, the level of activity of the mu opioid receptor effects sexual or reproductive function, gastrointestinal motility, immune response, or ability to withstand stress. Such information can further be used select appropriate therapeutic agents to treat diseases such as infertility, constipation, or diarrhea. Further, such information can be used to select appropriate therapeutic agents to increase immune response against an antigen such as a bacterium, a virus or a tumor cell in the subject, and to treat psychiatric diseases or disorders such as obsessive compulsive disorder, schizophrenia, or depression.

It is yet another object of the present invention to provide commercial detecting variant alleles of the human mu opioid receptor gene or the presence of a variant human mu opioid receptor in a bodily sample taken from a subject. The results of such tests can then be used to gain incite into a subject's ability to withstand pain, susceptibility to addiction, to diagnose a disease or disorder related to a physiological function regulated by the HPA or HPG axes such as sexual and reproductive functions, gastrointestinal motility, immune response, and the ability of the subject to withstand stress.

These and other aspects of the present invention will be better appreciated by reference to the following drawings and Detailed Description.

BRIEF DESCRIPTION OF THE DRAWINGS

FIGS. 1A–1B: The nucleic acid (1A) and protein sequence (1B) of the most common allele of the mu opioid receptor (SEQ ID NO:1 and SEQ ID NO:2, respectively) (GENBANK accession number L25119).

FIGS. 2A–2B: DNA (2A, SEQ ID NO:3) and protein (2B, SEQ ID NO:4) sequence of the most common allele of the mu opioid receptor with the T67C (Ser23Pro) polymorphism.

FIGS. 3A–3B: DNA (3A, SEQ ID NO:5) and protein (3B, SEQ ID NO:6) sequence of the most common allele of the mu opioid receptor with the T124A (Ser42Thr) polymorphism.

FIG. 4: DNA sequence (SEQ ID NO:7) of the most common allele of the mu opioid receptor with the C153T polymorphism.

FIG. 5: DNA sequence (SEQ ID NO:8) of the most common allele of the mu opioid receptor with the G174A polymorphism.

FIGS. 6A–6B: DNA (6A, SEQ ID NO:9) and protein (6B, SEQ ID NO:10) sequence of the most common allele of the mu opioid receptor with the 187INS:GGC polymorphism.

FIG. 6A is the sequence of the (+) strand; FIG. 7B the (−) strand.

FIG. 7A is the sequence of the (+) strand; FIG. 8B the (−) strand.

FIG. 8A is the sequence of the (+) strand; FIG. 9B the (−) strand.

FIG. 10A is the sequence of the (+) strand; FIG. 10B the (−) strand.

FIG. 11A is the sequence of the (+) strand; FIG. 11B the (−) strand.

DETAILED DESCRIPTION OF THE INVENTION

Figure 7A:
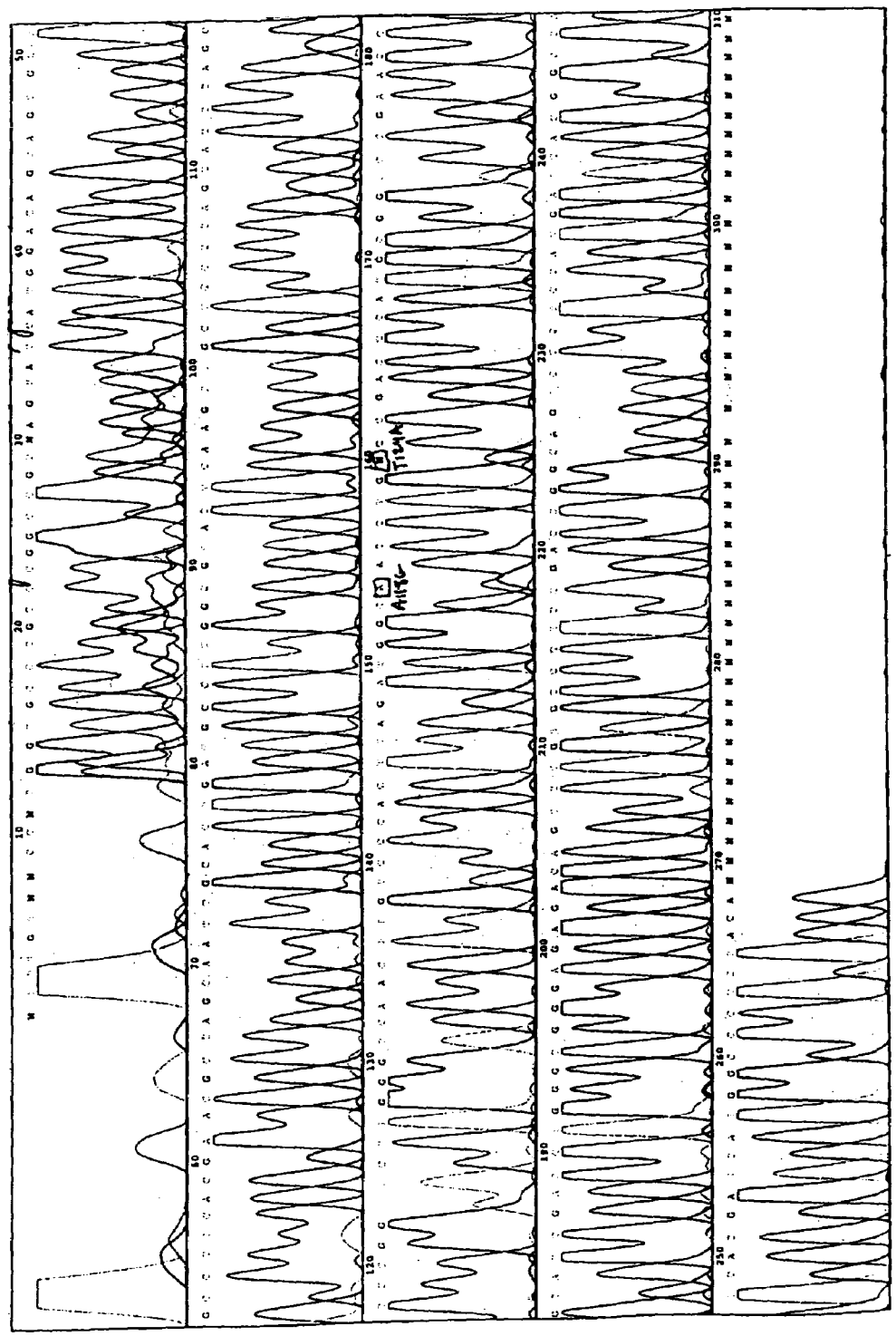
FIGS. 7A–7B: Electropherogram of the mu opioid receptor DNA from an individual heterozygous for both the A118G and the T124A single-nucleotide polymorphisms.

As explained above, the present invention is based upon Applicants' surprising and unexpected discovery of heretofore unknown polymorphisms, including a trinucleotide insertion and single-nucleotide polymorphisms (SNPs), in the human mu opioid receptor, along with combinations thereof. Furthermore, Applicants have discovered that more than one polymorphism can be present in either or both alleles of the human mu opioid receptor gene in a subject.

In addition, the present invention is based upon Applicants' surprising discovery of molecules of heretofore unknown isolated nucleic acid molecules which encode human mu opioid receptors, wherein the DNA sequences include a combination of presently known polymorphisms and subsequently of the human mu opioid receptor polymorphisms discovered by Applicants and set forth herein.

Furthermore, the present invention is based upon Applicants' surprising and unexpected discovery that the expression of variant alleles of the human mu opioid gene comprising a DNA sequence having a variation in SEQ ID NO:1, wherein the variations comprise T67C, T124A or 187INS:GGC, produce a variant mu opioid receptor comprising an amino acid sequence having a variation in SEQ ID NO:2, wherein the variations comprise Ser23Pro, Ser42Thr or the addition of a Gly residue following Gly63, and that these variant receptors exhibit a binding affinity for β-endorphin that is different from the binding affinity of a mu opioid receptor comprising an amino acid sequence of SEQ ID NO:2, and is encoded by the predominant or "most common" allele of the mu opioid receptor gene comprising a DNA sequence of SEQ ID NO:1.

Furthermore, the present invention is based upon Applicants' prediction that variant alleles of the mu opioid receptor gene, which comprise a DNA sequence having a variation in SEQ ID NO:1, wherein the variation comprises T67C, T124A or 187INS:GGC encode variant mu opioid receptors comprising amino acid sequence having a variation in SEQ ID NO:2 wherein the variation comprises Ser23Pro, Ser42Thr or the addition of a Gly residue following Gly63, the presence of such variant alleles in a bodily sample from a subject is expected to be indicative of the activity of the mu opioid receptors in the subject.

The present invention further extends to heretofore unknown polymorphisms of the human mu opioid receptor gene that can serve as genetic markers to map the locus of the human mu opioid receptor gene.

The present invention extends to diagnostic methods to determine a subject's increased or decreased susceptibility to at least one addictive disease. With the results of such methods, targeted prevention methods, early therapeutic intervention, and improved chronic treatment to opioid addiction are set forth herein and encompassed by the present invention. In addition, attending medical professionals of subjects armed with the results of such diagnostic methods can determine whether administration of opioid analgesics is appropriate or whether non-opioid derived analgesics should be administered to the subject. Also, appropriate choice and type of analgesic can be made in treating a subject's pain.

Methods for determining the presence of the one or more polymorphisms may be made using any of a large variety of methods for identifying altered nucleotides present in a nucleic acid sequence, by way of non-limiting examples as conventional DNA sequencing, differential hybridization to biological chip arrays such as an oligonucleotide gelpad microchip, or single nucleotide extension (SNE) on chip arrays such as on oligonucleotide gelpad microchips.

These methods are known to one of skill in the art, and are merely exemplified by the following citations: Khrapko K R, Lysov Y P, Khorlin A, Shick V V, Florentiev V L, Mirzabekov A D. 1989. An oligonucleotide hybridization approach to DNA sequencing. FEBS Lett 256:118–122; Khrapko K R, Lysov Y P, Khorlin A A, Ivanov I B, Yershov G M, Vasilenko S L, Florentiev V, Mirzabekov A D, 1991, A method for DNA sequencing by hybridization with oligonucleotide matrix. J DNA sequencing 1: 375–388; Fodor S P A, Read J L, Pirrung M C, Stryer L, Lu A T, Solas, D, 1991, Light directed, spatially addressable parallel chemical synthesis. Science 251:776–773; Southern E M, Maskos U, Elder J K, 1992, Analyzing and comparing nucleic acid sequences by hybridization to arrays of oligonucleotides: evaluation using experimental models, Genomics 13:1008–1017; Chee M, Yang R, Hubbell E, Berno A, Huang X C, Stern D, Winkler J, Lockhart D J, Morris M S, Fodor S P A. 1996. Accessing genetic information with high-density DNA arrays. Science 274:610–614; Hacia J G, Brody L C, Chee M S, Fodor S P A, Collins F. 1996. Detection of heterozygous mutations in BCRA1 using high density oligonucleotide arrays and two colour florescence analysis. Nature Genet 14:44–447; Yershov G, Barsky V, Belgovskiy A, Kirillov E, Kreindlin E, Ivanov I, Parinov S, Guschin D, Drobishev A, Dubiley S, Mirzabekov A. 1996. DNA Analysis and diagnostics on oligonucleotide microchips. Proc Natl Acad Sci USA 93:4913–4918; Shick V V Lebed Y B, Kryukov G V. 1998. Identification of HLA DQA1 alleles by the oligonucleotide microchip method. Mol Biol 32:697–688. Translated from Molekulyarna Biologiya 32:813–822; Wang D G, Fan J-B, Siao C-J, Berno A, Young P, Sapolsky R, Ghandour G, Perkins N, Winchester E, Spencer J, Kruglyak L, Stein L, Hsie L, Topaloglou T, Hubbell E, Robinson E, Mittmann M, Morris M S, Shen N, Kilburn D, Rioux J, Nusbaum C, Rozen S, Hudson T J, Lipschutz R, Chee M, Lander E S. 1998 Large scale identification, mapping and genotyping of single-nucleotide polymorphisms in the human genome. Science 280:1077–1082; Halushka M K, Fan J-B, Bentley K, Hsie L, Shen N, Weder A, Cooper R, Lipshutz R, Chakravarti A. 1999. Patterns of single-nucleotide polymorphisms in candidate genes for blood pressure homeostasis. Nature Genet 22:239–247; Cargill M, Altschuler D, Ireland J, Sklar P, Ardlie K, Patil N, Lane C R, Lim E P, Kalyanaraman N, Nemesh J, Ziaugra L, Friedland L, Rolfe A, Warrington J, Lipshutz R, Daley G Q, Lander E S. 1999. Characterization of single nucleotide polymorphisms in coding regions of human genes. Nature genet 22;231–238; Parinov S, Barsky V, Yershov G, Kirillov E, Timofeev E, Belgovskiy A, Mirzabekov A. 1996. DNA sequencing by hybridization to microchip octa- and decanucleotides extended by stacked pentanucleotides. Nucleic Acids Res 24:2998–3004; Guschin D, Yershof G, Zaslavsky A, Gemmell A, Shick V, Proudnikov V, Arenkov P, Mirzabekov A. 1997. Manual manufacturing of oligonucleotide, DNA and protein microchips. Anal Biochem 250:203–211; Drobyshev A, Mologina M. Shik V, Pobedimskaya D, Yershov G, Mirzabekov A. 1997. Sequence analysis by hybridization with oligonucleotide microchip: Identification of b-thalassemia mutations. Gene 188:45–52; Syvänen A-C, Aalto-Setälä K, Harju L, Kontula K, SØderlund H. 1990. A primer-guided nucleotide incorporation assay in the genotyping of apolipoprotein E. Genomics 8:684–692; Pastinen T, Kurg A, Metspalu A, Peltonen L, Syvanen A-C. 1997. Minisequencing: A specific tool for DNA analysis and diagnostics on oligonucleotide arrays. Genome res 7:606–614; Pastinen T, Perola M, Niini P, Terwilliger J, Salomaa V, Vartiainen E, Peltonen L, Syvänen A-C. 1998. Array-based multiplex analysis of candidate gene reveals two independent and additive genetic risk factors for myocardial infarction in the Finnish population. Hum Mol Genet 7:1453–1462; Dubiley S, Kirillov E, Mirzabekov A. 1999. Polymorphism analysis and gene detection by minisequencing on an array of gel-immobilized primers. Nucleic Acids Res 27:e19; and Syvänen A-C. 1999. From gels to chips: "Minisequencing" primer extension analysis of point mutations and single nucleotide polymorphisms. Hum Mutat 13:1–10. Such citations are not intended to be limiting but merely exemplary of the various methods available for detecting one or more of the polymorphisms described herein.

Also, the present invention extends to methods of determining a subject's increased or decreased susceptibility to pain and response to analgesics, and using that information when prescribing analgesics to the subject.

Furthermore, the present invention extends to diagnosing a disease or disorder related to a physiological function regulated by the HPA and HPG axes, such as sexual and reproductive functions, gastrointestinal motility, immune response, and the ability to withstand stress.

The present invention further extends to variant alleles of the human mu opioid receptor gene comprising a DNA sequence comprising a heretofore unknown polymorphism, such as:

T67C; T124A; C153T; G174A or 187INS:GGC, or combinations thereof.

Furthermore, Applicants' invention extends to variant alleles of the human mu opioid receptor gene comprising a DNA sequence having at least two variations in the predominant or "most common" allele comprising a human mu opioid receptor gene comprising a DNA sequence of SEQ ID NO:1, wherein at least one variation comprises T67C; T124A; C153T; G174A or 187INS:GGC, the at least one other being any other of the foregoing or at least one known in the art, such as but not limited to A118G, C17T, G24A, G779A, or G942A.

Furthermore, one aspect of the invention is based upon Applicants' finding that the C187INS:GGC polymorphism has been found only in persons with long-term polydrug abuse and dependency problems.

Consequently, an initial aspect of the present invention involves isolation of heretofore unknown variant alleles of the human mu opioid receptor gene. As used herein, the term "gene" refers to an assembly of nucleotides that encode a polypeptide, and includes cDNA and genomic DNA nucleic acids.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below. A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. Polynucleotides capable of discriminating between the wild-type and polymorphic alleles of the invention ("selectively hybridizable") may be prepared, and the conditions under which such polynucleotides selectively hybridize with the polymorphisms of the invention, may be achieved following guidance provided in the art, such as described by Conner et al., 1983, *Proc. Nat. Acad. Sci. U.S.A.* 80:278–82; Yershov et al., 1996, *Proc. Nat. Acad. Sci. U.S.A.* 93:4913–18; Drobyshev et al., 1997, *Gene* 188: 45–52; and Chee et al., 1996, *Science* 274:610–614. Selectively hybridizable reporting polynucleotides such as molecular beacons are also well known in the art.

For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for selectively hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a selectively hybridizable nucleic acid is at least about 10 nucleotides; preferably at least about 20 nucleotides; and more preferably the length is at least about 30 nucleotides; and most preferably 40 nucleotides. As noted above, the skilled artisan will be guided by the teachings in the art on selecting the length of a polynucleotide or nucleic acid sequence, the position(s) of the variant nucleotide(s), and the conditions and instrumentation to selectively identify nucleic acid sequences comprising one or more of the polymorphisms as described herein.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" or "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A coding sequence is "operatively associated with" a transcriptional and translational control sequences, such as a promoter for example, when RNA polymerase transcribes the coding sequence into mRNA, which in turn is translated into a protein encoding by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to selectively hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to selectively hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

The phrase "expected to be indicative" is used herein to refer to the correlation between the identity of the allelic variation(s) in an individual and the susceptibility of an individual to addictive disease, sensitivity to pain and analgesics, therapeutic effectiveness of analgesics, and other physiological manifestations described herein related to the function of the mu opioid receptor, such as but not limited to the responsiveness to stress, peripheral gastrointestinal function, immune function, and reproductive biology. The correlations are based on the findings in the present invention of the relationship between the biochemistry and cellular function of the variants of the mu opioid receptor and clinical observations, analyzed statistically, on history of drug dependence, reproductive function, gastrointestinal function, response to stress, and other previous or current conditions. Expected correlations of mu opioid receptor alleles and susceptibility to various conditions may be increased susceptibility or decreased susceptibility.

As explained above, within the scope of the present invention are DNA sequences encoding variant alleles of a human mu opioid receptor gene of the present invention, which comprise at least one variation in the predominant or "most common" allele of the human mu opioid receptor gene. The most common allele comprises a DNA sequence of SEQ ID NO:1, and variations in the most common allele comprise:

T67C; T124A; C153T; G174A or 187INS:GGC, or combinations thereof.

In another embodiment, the present invention comprises DNA sequences encoding variant alleles of a human mu opioid receptor gene, comprising at least two variations in the predominant or "most common" allele of the human mu opioid receptor gene, wherein the most common human mu opioid receptor gene comprises a DNA sequence of SEQ ID NO:1. Variant alleles of the human mu opioid receptor gene encompassed by the present invention comprise a DNA sequence comprising at least two variations of SEQ ID NO:1, wherein one of the variation is T67C; T124; C153T; G174A or 187INS:GGC; and the at least one other is another of the foregoing polymorphisms or one known in the art, such as but not limited to A118G, C17T, G24A, G779A, or G942A.

Moreover, due to degenerate nature of codons in the genetic code, variant human mu opioid receptor proteins encoded by variant alleles of the present invention, wherein the variant human mu opioid receptors comprise an amino acid sequence having at least one variation in SEQ ID NO:2, wherein the variations comprise Ser42Thr or conserved variants thereof; or the addition of a Gly residue following Gly63 or conserved variants thereof, or combinations thereof, or either of the foregoing polymorphisms in combination with the other and/or any known in the art, can be encoded by nucleic acid molecules other than those set forth above. "Degenerate nature" refers to the use of different three-letter codons to specify a particular amino acid pursuant to the genetic code. It is well known in the art that the following codons can be used interchangeably to code for each specific amino acid:

```
Phenylalanine (Phe   UUU or UUC
or F)

Leucine (Leu or L)   UUA or UUG or CUU or CUC or CUA
                     or CUG Isoleucine (Ile or   AUU or AUC or AUA
I)

Methionine (Met or   AUG
M)

Valine (Val or V)    GUU or GUG of GUA or GUG

Serine (Ser or S)    UCU or UCC or UCA or UCG or AGU
                     or AGC Proline (Pro or P)   CCU or CCC or CCA or CCG Threonine (Thr or T)ACU or ACC or ACA or ACG Alanine (Ala or A)   GCU or GCG or GCA or GCG Tyrosine (Tyr or Y)  UAU or UCG Histidine (His or H)CAU or CAC Glutamine (Gln or Q)CAA or CAG Asparagine (Asn or   AAU or AAC
N)
```

| | -continued |
|---|---|
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, *Cell* 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A variant allele of the human mu opioid receptor gene of the present invention, whether genomic DNA or cDNA, can be isolated from any source, particularly from a human cDNA or genomic library. Methods for obtaining an allele of a human mu opioid receptor gene, variants thereof, or the most common, are well known in the art, as described above (see, e.g., Sambrook et al., 1989, supra).

Accordingly, any human cell potentially can serve as the nucleic acid source for the molecular cloning of a variant allele of the human mu opioid receptor gene of the present invention, or a nucleic acid molecule selectively hybridizable to a variant allele of a human mu opioid receptor gene of the present invention. The DNA may be obtained by standard procedures known in the art from cloned DNA (e.g., a DNA "library"), and preferably is obtained from a cDNA library prepared from tissues with high level expression of a human mu opioid receptor protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, an allele of a human mu opioid receptor gene of the present invention should be molecularly cloned into a suitable vector for propagation.

In the molecular cloning of a human mu opioid receptor gene of the present invention, DNA fragments are generated, some of which will encode an allele. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing an allele of a human mu opioid receptor of the present invention may be accomplished in a number of ways. For example, if an amount of a portion of an allele of a human mu opioid receptor gene, or its specific RNA, or a fragment thereof, is available and can be purified and labeled, the generated DNA fragments may be screened by nucleic acid hybridization to the labeled probe (Benton and Davis, 1977, *Science* 196:180; Grunstein and Hogness, 1975, *Proc. Natl. Acad. Sci. U.S.A.* 72:3961). For example, a set of oligonucleotides corresponding to the partial amino acid sequence information obtained for a human mu opioid receptor protein can be prepared and used as probes for DNA encoding a variant allele of a human mu opioid receptor gene of the present invention, as was done in a specific example, infra, or as primers for cDNA or mRNA (e.g., in combination with a poly-T primer for RT-PCR). Preferably, a fragment is selected that is highly unique to a variant allele of the human mu opioid receptor gene of the invention. Those DNA fragments with substantial homology to the probe will selectively hybridize. As noted above, the greater the degree of homology, the more stringent hybridization conditions can be used.

Further selection can be carried out on the basis of the properties of an allele of a human mu opioid receptor gene of the present invention e.g., if the allele encodes a variant human mu opioid receptor protein having an isoelectric, electrophoretic, amino acid composition, or partial amino acid sequence different from that produced from the expression of the most common allele of a human mu opioid receptor gene (SEQ ID NO:1) herein. Thus, the presence of an allele of a human mu opioid receptor gene of the present invention may be detected by assays based on the physical, chemical, or immunological properties of its expressed product. For example, cDNA clones, or DNA clones which hybrid-select the proper mRNAs, can be selected which produce a protein that, e.g., has different electrophoretic migration, isoelectric focusing or non-equilibrium pH gel electrophoresis behavior, proteolytic digestion maps, or antigenic properties as known for a human mu opioid receptor produced from expression of a most common allele of the human mu opioid receptor gene (SEQ ID NO:1).

An allele of a human mu opioid receptor gene of the present invention can also be identified by mRNA selection, i.e., by nucleic acid hybridization followed by in vitro translation. In this procedure, nucleotide fragments are used to isolate complementary mRNAs by hybridization. Such DNA fragments may represent available, purified DNA of an allele of a human mu opioid receptor gene of the present invention, or may be synthetic oligonucleotides designed from the partial amino acid sequence information. Immunoprecipitation analysis or functional assays of the in vitro translation products of the products of the isolated mRNAs identifies the mRNA and, therefore, the complementary DNA fragments, that contain the desired sequences.

A labeled cDNA of an allele of a human mu opioid receptor gene of the present invention, or fragments thereof, or a nucleic acid selectively hybridizable to an allele of a human mu opioid receptor gene of the present invention, can be synthesized using sequences set forth herein. The radiolabeled mRNA or cDNA may then be used as a probe to identify homologous DNA fragments from among other genomic DNA fragments. Suitable labels include enzymes, radioactive isotopes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-a 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70. 419–439, 1980 and in U.S. Pat. No. 4,857,453.

Other labels for use in the invention include magnetic beads or magnetic resonance imaging labels.

Cloning Vectors

The present invention also relates to cloning vectors comprising variant alleles of a human mu opioid receptor gene of the present invention, and an origin of replication. For purposes of this Application, an "origin of replication" refers to those DNA sequences that participate in DNA synthesis.

As explained above, in an embodiment of the present invention, variant alleles of a human mu opioid receptor gene of the present invention comprise a DNA sequence having at least one variation in the most common allele of a human mu opioid receptor gene comprising a DNA sequence of SEQ ID NO:1, wherein the variation comprises T67C; T124A; C153T; G174A or 187INS:GGC, or combinations thereof.

In another embodiment, the present invention extends to variant alleles of a human mu opioid receptor gene, comprising a DNA sequence having at least two variations in the DNA sequence of SEQ ID NO:1, wherein one of the variations comprises T67C; T124A; C153T; G174A or 187INS:GGC, the at least one other being another of the foregoing or one known in the art, such as but not limited to A118G, C17T, G24A, G779A, or G942A.

Furthermore, an isolated variant allele of a human mu opioid receptor gene of the present invention, or isolated nucleic acid molecules selectively hybridizable to an isolated variant allele of a human mu opioid receptor gene of the present invention, can be inserted into an appropriate cloning vector in order to produce multiple copies of the variant allele or isolated nucleic acid molecule. A large number of vector-host systems known in the art may be used. Possible vectors include, but are not limited to, plasmids or modified viruses. The vector system used however must be compatible with the host cell used. Examples of vectors include having applications herein, but are not limited to *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating a variant allele of the human mu opioid receptor gene of the present invention, or an isolated nucleic acid selectively hybridizable thereto, into a cloning vector which has complementary cohesive termini. However, if the complementary restriction sites used to fragment the variant allele or isolated nucleic acid selectively hybridizable thereto are not present in the cloning vector, the ends of the variant allele or the isolated nucleic acid molecule selectively hybridizable thereto may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Such recombinant molecules can then be introduced into host cells via transformation, transfection, infection, electroporation, etc., so that many copies of a variant allele of a human mu opioid receptor gene of the present invention, or an isolated nucleic acid molecule selectively hybridizable thereto, can be generated. Preferably, the cloned isolated variant is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences from the yeast 2µ plasmid.

In an alternative method an isolated variant allele of a human mu opioid receptor gene of the present invention or an isolated nucleic acid molecule selectively hybridizable thereto may be identified and isolated after insertion into a suitable cloning vector in a "shot gun" approach. Enrichment for a variant allele, for example, by size fractionation, can be done before insertion into the cloning vector.

Expression Vectors

As stated above, the present invention extends to an isolated variant allele of a human mu opioid receptor gene, comprising a DNA sequence having at least one variation in the DNA sequence of the predominant or "most common" allele of the human mu opioid receptor gene comprising a DNA sequence of SEQ ID NO:1 wherein the variations comprise T67C; T124A; C153T; G174A or 187INSGGC, or combinations thereof.

In another embodiment, the present invention extends to an isolated variant allele of a human mu opioid receptor gene, a DNA sequence having at least two variations in the predominant or "most common" allele of the human mu opioid receptor gene comprising a DNA sequence of SEQ ID NO:1 wherein the at least one variation is T67C; T124A; C153T; G174A or 187INSGGC, the at least one other being another of the foregoing or a variant known in the art, such as but not limited to A118G, C17T, G24A, G779A, or G942A.

Variant alleles of the present invention, along with isolated nucleic acid molecules selectively hybridizable to such variant alleles, can be inserted into an appropriate expression vector, i.e., a vector which contains the necessary elements for the transcription and translation of the inserted protein-coding sequence. Thus, a variant allele of the present invention, or an isolated nucleic acid molecule selectively hybridizable to a variant allele of the present invention, is operatively associated with a promoter in an expression vector of the invention. A DNA sequence is "operatively associated" to an expression control sequence, such as a promoter, when the expression control sequence controls and regulates the transcription and translation of that DNA sequence. The term "operatively associated" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a variant allele of the present invention, or an isolated nucleic acid selectively hybridizable thereto does not contain an appropriate start signal, such a start signal can be inserted into the expression vector in front of (5' of) the molecule.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by an allele comprising a human mu opioid receptor gene.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. A variant allele of a human mu opioid receptor gene of the present invention or an isolated nucleic acid molecule selectively hybridizable thereto may be expressed chromosomally, after integration of the coding sequence by recombination. In this regard, any of a number of amplification systems may be used to achieve high levels of stable gene expression (See Sambrook et al., 1989, supra).

A unicellular host transformed or transfected with an expression vector of the present invention is cultured in an appropriate cell culture medium that provides for expression by the unicellular host of the variant allele, or isolated nucleic acid selectively hybridizable thereto.

Any of the methods previously described for the insertion of DNA fragments into a cloning vector may be used to construct expression vectors of the present invention. These methods may include in vitro recombinant DNA and synthetic techniques and in vivo recombination (genetic recombination).

Expression of a variant allele of a human mu opioid receptor gene of the present invention or an isolated nucleic acid molecule selectively hybridizable to a variant allele of a human mu opioid receptor gene, may be controlled by any promoter/enhancer element known in the art, but these regulatory elements must be functional in the host selected for expression. Promoters which may be used to control expression include, but are not limited to, the SV40 early promoter region (Benoist and Chambon, 1981, Nature 290: 304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318: 533–538; Alexander et al., 1987, Mol. Cell. Biol. 7:1436–1444), mouse mammary tumor virus control region which is active in testicular, breast, lymphoid and mast cells (Leder et al., 1986, Cell 45:485495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639-1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadal releasing hormone gene control region which is active in the hypothalamus (Mason et al., 1986, Science 234:1372–1378).

Moreover, expression vectors comprising a variant allele of a human mu opioid receptor gene of the present invention, or an isolated nucleic acid molecule selectively hybridizable thereto, can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the variant allele or isolated nucleic acid molecule selectively hybridizable thereto can be amplified by PCR to provide for detection of the amplified product. In the second approach, the presence of a foreign gene inserted into an expression vector of the present invention can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In yet another example, if an isolated variant allele of a human mu opioid receptor gene of the present invention, or an isolated nucleic acid molecule selectively hybridizable thereto, is inserted within the "selection marker" gene sequence of the vector, recombinants containing the insert can be identified by the absence of the inserted gene function. In the fourth approach, recombinant expression vectors can be identified by assaying for the activity, biochemical, or immunological characteristics of the gene product expressed by the recombinant, provided that the expressed protein assumes a functionally active conformation.

Naturally, the present invention extends to a method of producing a variant human mu opioid receptor comprising an amino acid sequence having at least one variation in the amino acid sequence of SEQ ID NO:2, wherein the variation comprises Ser23Pro or conserved variants thereof. An example of such a method comprises the steps of culturing a unicellular host transformed or transfected with an expression vector comprising a variant allele of a human mu opioid receptor gene comprising a DNA sequence having a variation in SEQ ID NO:1, wherein the variation comprises T67C, wherein the variant allele which is operatively associated with a promoter. The transformed or transfected unicellular host is then cultured under conditions that provide for expression of the variant allele of the human mu opioid receptor gene, and the expression product is recovered from the unicellular host.

Another example involves culturing a unicellular host transformed or transfected with an isolated nucleic acid molecule selectively hybridizable to a variant allele of a human mu opioid receptor gene comprising a DNA sequence having at least one variation in SEQ ID NO:1, wherein the variation comprises T67C, wherein the isolated nucleic acid molecule is operatively associated with a promoter. The variant human mu opioid receptor is then recovered from the host.

Furthermore, the present invention extends to a method of producing a variant human mu opioid receptor comprising an amino acid sequence having at least one variation in the amino acid sequence of SEQ ID NO:2, wherein the variation comprises Ser42Thr or conserved variants thereof. An example of such a method comprises the steps of culturing a unicellular host transformed or transfected with an expression vector comprising a variant allele of a human mu opioid receptor gene comprising a DNA sequence having a variation in SEQ ID NO:1, wherein the variation comprises T124A, wherein the variant allele which is operatively associated with a promoter. The transformed or transfected unicellular host is then cultured under conditions that provide for expression of the variant allele of the human mu opioid receptor gene, and the expression product is recovered from the unicellular host.

Another example involves culturing a unicellular host transformed or transfected with an isolated nucleic acid molecule selectively hybridizable to a variant allele of a human mu opioid receptor gene comprising a DNA sequence having at least one variation in SEQ ID NO:1, wherein the variation comprises T124A, wherein the isolated nucleic acid molecule is operatively associated with a promoter. The variant human mu opioid receptor is then recovered from the host.

And further, the present invention extends to a method of producing a variant human mu opioid receptor comprising an amino acid sequence having at least one variation in the amino acid sequence of SEQ ID NO:2, wherein the variation comprises 187INS:GGC or conserved variants thereof. An example of such a method comprises the steps of culturing a unicellular host transformed or transfected with an expression vector comprising a variant allele of a human mu opioid receptor gene comprising a DNA sequence having a variation in SEQ ID NO:1, wherein the variation comprises the addition of a glycine residue following Gly63, wherein the variant allele which is operatively associated with a promoter. The transformed or transfected unicellular host is then cultured under conditions that provide for expression of the variant allele of the human mu opioid receptor gene, and the expression product is recovered from the unicellular host.

Another example involves culturing a unicellular host transformed or transfected with an isolated nucleic acid molecule selectively hybridizable to a variant allele of a human mu opioid receptor gene comprising a DNA sequence having at least one variation in SEQ ID NO:1, wherein the variation comprises 187INS:GGC, wherein the isolated nucleic acid molecule is operatively associated with a promoter. The variant human mu opioid receptor is then recovered from the host.

In another embodiment, the present invention extends to a method for producing a variant human mu opioid receptor comprising an amino acid sequence having at least two variations in SEQ ID NO:2, wherein the variations comprise
Ser23Pro or conserved variants thereof;
Ser42Thr or conserved variants thereof;
addition of a Gly residue following Gly63 or conserved variants thereof;

Such a method comprises the steps of culturing a unicellular host transformed or transfected with an expression vector comprising a variant allele of a human mu opioid receptor gene of the present invention or an isolated nucleic acid molecule selectively hybridizable thereto, and operatively associated with a promoter, that provides for expression of the variant allele or the isolated nucleic acid molecule selectively hybridizable thereto. After expression, a variant human mu opioid receptor of the present invention is recovered from the unicellular host.

A wide variety of unicellular host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., 1988, Gene 67:31–40), pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED PstI, SalI, SbaI, SmaI, and EcoRI cloning site, with the vector expressing both the cloned gene and DHFR; see Kaufman, *Current Protocols in Molecular Biology*, 16.12 (1991).

Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible metallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to produce a variant human mu opioid receptor or the present invention. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Examples of unicellular hosts contemplated by the present invention include, but are not limited to *E. coli Pseudonomas, Bacillus, Streptomyces*, yeast, CHO, R1.1, B-W, L-M, COS1, COS7, BSC1, BSC40, BMT10 and Sf9 cells. In addition, a host cell strain may be chosen which modulates the expression of a variant allele comprising a human mu opioid receptor gene, or an isolated nucleic acid selectively hybridizable thereto, such that the gene product is modified and processed in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, a translocation signal sequence of an isolated variant allele of a human mu opioid receptor gene of the present invention, or an isolated nucleic acid selectively hybridizable thereto, expressed in bacteria may not be properly spliced. Expression in yeast can produce a glycosylated product. Expression in eukaryotic cells can increase the likelihood of "native" glycosylation and folding. Moreover, expression in mammalian cells can provide a tool for reconstituting, or constituting activity of the variant human mu opioid receptor gene. Furthermore, different vector/host expression systems may affect processing reactions, such as proteolytic cleavages, to a different extent.

Vectors are introduced into the desired unicellular hosts by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

An isolated variant human mu opioid receptor of the present invention produced as an integral membrane protein can be isolated and purified by standard methods. Generally, the variant human mu opioid receptor can be obtained by lysing the membrane with detergents, such as but not limited to, sodium dodecyl sulfate (SDS), Triton X-100, Nonidet P-40 (NP-40), digoxin, sodium deoxycholate, and the like, including mixtures thereof. Solubilization can be enhanced by sonication of the suspension. Soluble forms of an isolated variant of a human mu opioid receptor can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Due to the degeneracy of nucleotide coding sequences, other DNA sequences which encode the variant human mu opioid receptors of the present invention may be used in the practice of the present invention. These include but are not limited to allelic genes, homologous genes from other species, and nucleotide sequences comprising all or portions of genes which are altered by the substitution of different codons that encode the same amino acid residue within the sequence, thus producing a silent change. Likewise, the conserved variants of human mu opioid receptors of the present invention include, but are not limited to, those containing, as a primary amino acid sequence, substitutions of amino acids in a variant human mu opioid receptor as set forth above, which are functionally equivalent to amino acids of the variations set forth above, resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Antibodies to Variant Human Mu Opioid Receptors of the Present Invention

According to the invention, variant human mu opioid receptors disclosed herein may be used as an immunogen to generate antibodies that recognize the claimed variant mu opioid receptors. Such antibodies include but are not limited to polyclonal, monoclonal, chimeric, single chain, Fab fragments, and an Fab expression library. Furthermore, antibodies of the invention may be cross reactive, e.g., they may recognize human mu opioid receptors comprising an amino acid sequence of SEQ ID NO:1, as well as mu opioid receptors from different species. Polyclonal antibodies have greater likelihood of cross reactivity. Alternatively, an antibody of the invention may be specific for a specific variant allele of a mu opioid receptor.

Various procedures known in the art may be used for the production of polyclonal antibodies to variant opioid receptors disclosed herein. For the production of an antibody, various host animals can be immunized by injection with a variant human mu opioid receptor of the invention, including but not limited to rabbits, mice, rats, sheep, goats, etc. In one embodiment, the variant human mu opioid receptor can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a particular human mu opioid receptor of the present invention, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad.*

Sci. U.S.A. 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314: 452–454 (1985)] by splicing the genes from a mouse antibody molecule specific for a variant human mu opioid receptor of the present invention together with genes from a human antibody molecule of appropriate biological activity can be used; such antibodies are within the scope of this invention. Such human or humanized chimeric antibodies are preferred for use in determining the presence of a particular human mu opioid receptor in a sample taken from a subject.

According to the invention, techniques described for the production of single chain antibodies [U.S. Pat. Nos. 5,476,786 and 5,132,405 to Huston; U.S. Pat. No. 4,946,778] can be adapted to produce particular variant mu opioid receptor-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a variant mu opioid receptor of the present invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a variant human mu opioid receptor of the present invention, one may assay generated hybridomas for a product which binds to a fragment of the variant human mu opioid receptor containing such epitope.

The foregoing antibodies can be used in methods known in the art relating to the localization and activity of a variant human mu opioid receptor, e.g., for Western blotting, imaging a variant human mu opioid receptor in situ, measuring levels thereof in appropriate physiological samples, etc. using any of the detection techniques mentioned above or known in the art.

Consequently, the present invention extends to a method for determining a susceptibility of a subject to one addictive disease comprising removing a bodily sample comprising a first and second allele of a human mu opioid receptor gene from the subject, and determining whether either the first or second alleles, or both alleles comprise a DNA sequence having at least one variation in SEQ ID NO:1, wherein the variation comprises:

T67C, T124A, C153T, G174A, or 187INS:GGC, or any combination thereof.

In this embodiment, the biological sample can be a biological fluid, such as but not limited to, blood, serum, plasma, interstitial fluid, plural effusions, urine, cerebrospinal fluid, and the like. Preferably, variant alleles of a human mu opioid receptor gene, as described above, are detected in serum or urine, which are both readily obtained. Alternatively, variant alleles of a human mu opioid receptor gene indicating increased or decrease susceptibility to addictive diseases in the subject as described above, can be detected from cellular sources, such as, but not limited to, brain tissue biopsies, adipocytes, testes, heart, and the like. For example, cells can be obtained from an individual by biopsy and lysed, e.g., by freeze-thaw cycling, or treatment with a mild cytolytic detergent such as, but not limited to, TRITON X-100®, digitonin, NONIDET P(NP)-40®, saponin, and the like, or combinations thereof (see, e.g., International Patent Publication WO 92/08981, published May 29, 1992). In yet another embodiment, samples containing both cells and body fluids can be used (see ibid.).

Other methods presently understood by a skilled artisan, and encompassed by the present invention, can also be used to detect the presence of either variation in either or both alleles of a human mu opioid receptor gene in a sample, and hence increased or decreased susceptibility to at least one addictive disease of the subject relative to the susceptibility of at least one addictive disease in a standard comprising alleles of the human mu opioid receptor gene comprising a DNA sequence of SEQ ID NO:1.

For example, an optionally detectably labeled isolated nucleic acid molecule selectively hybridizable to an isolated variant allele of a human mu opioid receptor gene comprising a DNA sequence having a variation in SEQ ID NO:1, wherein the variation comprises T124A, can be used in standard Northern hybridization analysis to detect the presence, and in some instances quantitate the level of transcription of such a variant allele of the present invention.

Alternatively, oligonucleotides of the invention can be used as PCR primers to amplify an allele of a human mu opioid receptor gene of the biological sample e.g., by reverse transcriptase-PCR, or amplification of the allele itself. The amplified mRNA or DNA can then be quantified or sequenced in order to determine the presence of a variant allele, and the susceptibility of the subject to addictive diseases. Furthermore, variations in SEQ ID NO:1, as described above, can be found by creation or deletion of restriction fragment length polymorphisms (RFLPs) not found in the predominant or "most common" allele, hybridization with a specific probe engineered to selectively hybridize to variation described, (or lack of hybridization with a probe specific for the predominant or "most common" allele), as well as by other techniques.

Furthermore, biochemical or immunochemical/biochemical (e.g., immunoprecipitation) techniques can be used to detect the presence and or level of expression of a variant allele of a human mu opioid receptor gene comprising a DNA sequence having a variation in SEQ ID NO:1, wherein the variation comprises T67C, T124A or 187INS:GGC.

For example, methods such as radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc using antibodies of the present invention, can be used to determine the presence of a variant in an allele of a human mu opioid receptor gene in a sample taken from the subject, and hence, the subject's susceptibility to addictive diseases relative to the susceptibility of a standard. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Determining Susceptibility to Pain in a Subject

In yet another embodiment, the present invention extends to a method for determining a susceptibility to pain in a subject.

Hence, disclosed herein is a method of determining susceptibility of pain in a subject, comprising the steps of removing a bodily sample comprising a first and second allele of a human mu opioid receptor gene from the subject, and determining whether either the first or second alleles, or both alleles, comprise a DNA sequence having at least one variation in SEQ ID NO:1, wherein the variation comprises T67C, T124A or 187INS:GGC.

The presence of at least one variation in either or both alleles of the human mu opioid receptor gene is expected to be indicative of the subject's increased or decreased susceptibility to pain relative to a person homozygous with respect to the predominant or "most common" allele comprising a human mu opioid receptor gene comprising a DNA sequence of SEQ ID NO:1.

Numerous methods presently available, and understood by the skilled artisan, can be used to "genotype" a subject in regards to the presence of a variant allele of a human mu opioid receptor gene in the genome of the subject. In particular, methods described above to ascertain increased or decreased susceptibility to addictive diseases have relevance in this embodiment of the present invention, and can readily be used herein. For example, Northern blot hybridization an isolated nucleic acid of the present invention selectively hybridizable to an isolated variant allele of a human mu opioid receptor gene comprising a DNA sequence having a variation of SEQ ID NO:1, wherein the variation comprises T67C; T124A; or 187INS:GGC, as a probe, along with RT-PCR, PCR, and numerous immunoassays described above, have applications herein.

Moreover, once susceptibility to pain in a subject has been determined, it is possible for attending medical professionals treating the subject for pain to administer an appropriate amount of pain reliever to the subject in order to induce analgesia. More specifically, an inappropriate amount of pain reliever is administered to a subject when either the subject is not relieved of pain, or the subject is exposed to potential deleterious side effects of the pain reliever, such as induction of addiction to the pain reliever, brain damage, or death.

However, since the amount of pain reliever administered to a subject is presently based principally on weight, information regarding the genotype of the subject with respect to the human mu opioid receptor gene can help increase accuracy in determining a therapeutically effective amount of pain reliever to administer in order to induce analgesia, making the use of pain relievers much safer for the subject.

Similarly, once ascertained, a susceptibility to addiction and response to human mu opioid receptor directed therapeutic agents, appropriate medications and dosages thereof can be determined for treatment of addictive diseases.

Diagnosing and Treating a Disease or Disorder Related to a Physiological Function Regulated by the HPA or HPG Axes In yet another embodiment, the present invention extends to a method for diagnosing a disease or disorder related to a physiological function regulated by the HPA or HPG axes. Examples of such physiological functions include sexual or reproductive functions, gastrointestinal motility, immune response, or ability to withstand stress. Moreover, examples of diseases or disorders which can be diagnosed with the present invention include infertility, constipation, diarrhea, and decreased immune response to name only a few.

Hence, disclosed herein is a method of diagnosing a disease or disorder related to a physiological function regulated by the HPA or HPG axes in a subject, comprising the steps of removing a bodily sample comprising a first and second allele of a human mu opioid receptor gene from the subject, and determining whether either the first or second alleles, or both alleles, comprise a DNA sequence having at least one variation in SEQ ID NO:1, wherein the variation comprises T67C; T124A or 187INS:GGC.

The presence of at least one variation in either or both alleles of the human mu opioid receptor gene is expected to be indicative of a disease or disorder related to a physiological function regulated by the HPA or HPG axes relative to such functions in a person homozygous with respect to the predominant or "most common" allele comprising a human mu opioid receptor gene comprising a DNA sequence of SEQ ID NO:1. Examples of such physiological functions include sexual or reproductive functions, gastrointestinal motility, immune response, or ability to withstand stress. Moreover, examples of diseases or disorders which can be diagnosed with the present invention include infertility, constipation, diarrhea, and decreased immune response to name only a few relative to a person homozygous with respect to the predominant or "most common" allele comprising a human mu opioid receptor gene comprising a DNA sequence of SEQ ID NO:1.

Numerous methods presently available, and understood by the skilled artisan, can be used to "genotype" a subject in regards to the presence of a variant allele of a human mu opioid receptor gene in the genome of the subject. In particular, methods described above to ascertain increased or decreased susceptibility to addictive diseases have relevance in this embodiment of the present invention, and can readily be used herein. For example, Northern blot hybridization an isolated nucleic acid of the present invention selectively hybridizable to an isolated variant allele of a human mu opioid receptor gene comprising a DNA sequence having a variation of SEQ ID NO:1, wherein the variation comprises T67C; T124A; or 187INS:GGC as a probe, along with RT-PCR, PCR, and numerous immunoassays described above, have applications herein.

In an alternative, such a method comprises removing a bodily sample from the subject comprising a mu opioid receptor, and determining whether the receptor comprises an amino acid sequence having a variation in SEQ ID NO:1, wherein the variation comprises: Ser23Pro, Ser42Thr or conserved variants thereof; or addition of a Gly residue following Gly 63 or conserved variants thereof, such that the presence of at least one variation is expected to be indicative of a disease or disorder related to a physiological function regulated by the HPA or HPG axes, such as sexual function or development, gastric motility, immune response, or the ability of the subject to withstand stress, relative to regulation of such activities in a standard comprises a human mu opioid receptor having an amino acid sequence of SEQ ID NO:2.

In particular, the presence of a variant human mu opioid receptor comprising an amino acid sequence having at least one variation in SEQ ID NO:2 wherein the variation comprises Ser23Pro or conserved variants thereof, is expected to be indicative of increased sexual or reproductive functions, increased gastrointestinal motility, increased immune response, or increased ability to withstand stress relative to the levels of such function observed in a standard having a mu opioid receptor comprising an amino acid sequence of SEQ ID NO:2.

Moreover, the presence of a variant human mu opioid receptor comprising an amino acid sequence having at least one variation in SEQ ID NO:2 wherein the variation comprises Ser42Thr or conserved variants thereof, is expected to be indicative of increased sexual or reproductive functions, increased gastrointestinal motility, increased immune response, or increased ability to withstand stress relative to the levels of such function observed in a standard having a mu opioid receptor comprising an amino acid sequence of SEQ ID NO:2.

Furthermore, the presence of a variant human mu opioid receptor comprising an amino acid sequence having a variation in SEQ ID NO:2, wherein the variation comprises the addition of a Gly residue following Gly63 or conserved variants thereof, in a bodily sample taken from a subject is expected to be indicative of decreased sexual or reproductive functions, decreased gastrointestinal motility, decreased immune response, or decreased ability to withstand stress relative to the levels of such function observed in a standard having a mu opioid receptor comprising an amino acid sequence of SEQ ID NO:2. Examples of specific diseases or disorders related to regulation of physiological functions regulated by the HPA or HPG axes include infertility, constipation, diarrhea, decreased immune response to antigens, or a lack of ability to withstand stress.

Numerous methods of detecting a variant mu opioid receptor as described above are presently available to the skilled artisan. For example a receptor in the bodily sample can be digested into fragments with proteases or CNBr. These fragments can then be collected and sequenced using presently known methods. Once the sequence of the receptor has been determined, it is a simple matter of comparing it to the amino acid sequence of the predominant or "most common" receptor having an amino acid sequence of SEQ ID NO:2, to determine whether a variation in the amino acid sequence exists. Other methods involve immune assays described herein using antibodies of the present invention, or a binding assay to determine the binding affinity of the receptor to β-endorphin.

Moreover, once a disease or disorder related to a physiological condition regulated by the HPA or HPG axes has been diagnosed, it is possible for attending medical professionals treating the suspect to select an appropriate therapeutic agent for treating such a disease and disorder, and a therapeutically effective amount of such pain reliever to administer to the subject. Hence naturally, the present invention extends to a method for selecting an appropriate therapeutic agent for treating a disease or disorder related to a physiological function regulated by the HPA and HPG axes, wherein such physiological functions include sexual and reproductive functions, gastrointestinal motility, immune response, and ability to withstand stress. Furthermore, diseases or disorders related to such functions which can be diagnosed with the present invention include, but are not limited to, infertility, constipation, diarrhea, and decreased immune response, to name only a few.

Commercial Kits

Furthermore, as explained above, the present invention extends to commercial kits having applications in screening a bodily sample taken from a subject for the presence of a variant allele comprising a human mu opioid receptor comprising a DNA sequence having a variation in SEQ ID NO:1, wherein the variation comprises T67C, T124A, C153T, G174A or 187INS:GGC, or combinations thereof, as well as with other known polymorphisms.

With information obtained from the use of a test kit of the present invention, an attending health profession can determine whether the subject has an susceptibility to pain relative to a standard, an increased susceptibility to at least one addictive disease relative to the susceptibility of a standard, a therapeutically effective amount of pain reliever to administer to the subject suffering from pain in order to induce analgesia in the subject relative to the therapeutically effective amount of pain reliever to administer to a standard in order to induce analgesia in the standard, or a therapeutically effective amount therapeutic agent to administer to a subject suffering from at least one addictive disease, relative to the therapeutically effective amount of therapeutic agent to administer to standard suffering from at least one addictive disease. Furthermore, such information can also be used to diagnose a disease or disorder related to a physiological function regulated by the HPA or HPG axes, such as sexual or reproductive functions, gastrointestinal motility, immune response, or ability to withstand stress, or selecting an appropriate therapeutic agent and a therapeutically effective amount of such an agent to administer to a subject suffering from a disease or disorder related to a physiological function regulated by the HPA or HPG axes. In each use described above, the standard comprises a first and or second allele of a human mu opioid receptor gene comprising a DNA sequence of SEQ ID NO:1.

Accordingly, a test kit of the present invention for determining whether a subject comprises a variant allele of a human mu opioid receptor gene comprising a DNA sequence having a variation in SEQ ID NO:1, comprises means for detecting the presence of a variation in a first and or second allele comprising a human mu opioid receptor in a biological sample from a subject, and optimally packaged with directions for use of the kit. In one particular aspect, the means for detecting the presence of a variant allele of a human mu opioid receptor gene comprising a DNA sequence having a variation in SEQ ID NO:1, comprises a specific binding partner of a human mu opioid receptor, such as an antibody, and means for detecting the level of binding of the specific binding partner of the antibody to the particular human mu opioid receptor. In another embodiment, a test kit comprises an oligonucleotide probe(s) for binding to a variant allele of a human mu opioid receptor gene comprising a DNA sequence having a variation in SEQ ID NO:1; and means for detecting the level of binding of the probe to the variant allele, wherein detection binding of the probe to the variant allele indicates the presence of a variant comprising a human mu opioid receptor gene comprising a DNA sequence having a variation in SEQ ID NO:1, wherein the variation comprises: T67C, T124A, C153T, G174A or 187INS:GGC, or combinations thereof, as well as in combination with other known polymorphisms.

The sequence of the oligonucleotide probe used in a commercial kit will determine which if any variation is present in an allele comprising a human mu opioid receptor gene. Should no binding be detected, it is probable that no such variation exists in either allele of the subject.

More specifically, a commercial test kit of the present invention comprises:
 a) PCR oligonucleotide primers suitable for detection of a variant allele of a human mu opioid receptor gene comprising a DNA sequence having a variation in SEQ ID NO:1, as set forth above,
 b) other reagents; and
 c) directions for use of the kit.

Examples of PCR oligonucleotide primer suitable for detection of an allele comprising a human mu opioid receptor gene comprising a DNA sequence having a variation in SEQ ID NO:1 can be readily produced by a person of ordinary skill in the art with teaching set forth herein, and variations of SEQ ID NO:1 also set forth herein.

The present invention further extends to commercial test kits capable of detecting a variant human mu opioid receptor in a bodily sample taken from a subject. Examples of variant human mu opioid receptors that can be detected with a kit of the present invention comprise:
 (a) a variant human mu opioid receptor comprising an amino acid sequence having a variation in SEQ ID NO:2, wherein the variation comprises the variation comprises Ser23Pro or conserved variants thereof;
 (b) a variant human mu opioid receptor comprising an amino acid sequence having a variation in SEQ ID NO:2, wherein the variation comprises the variation comprises Ser42Thr or conserved variants thereof; or
 (c) a variant human mu opioid receptor comprising an amino acid sequence having at least two variations in SEQ ID NO:2, wherein the variations comprise the addition of a Gly residue following Gly63 or conserved variants thereof.

Moreover, a commercial test kit of the present invention can be used to determine: a susceptibility to pain in a subject relative to a standard, an increased susceptibility to at least one addictive disease in a subject relative to the susceptibility of a standard, a therapeutically effective amount of pain reliever to administer to the subject suffering from pain in order to induce analgesia in the subject relative to the therapeutically effective amount of pain reliever to administer to a standard in order to induce analgesia in the standard, a therapeutically effective amount of a therapeutic agent to administer to a subject suffering from at least one addictive disease, relative to the therapeutically effective amount of therapeutic agent to administer to standard suffering from at least one addictive disease, a diagnosis of a disease or disorder related to a physiological function regulated by the HPA or HPG axes, such as sexual or reproductive functions, gastrointestinal motility, immune response, or ability to withstand stress, or selecting an appropriate therapeutic agent and a therapeutically effective amount of such an agent to administer to a subject suffering from a disease or disorder related to a physiological function regulated by the HPA or HPG axes. In each use described above, the standard comprises a first and or second allele of a human mu opioid receptor gene comprising a DNA sequence of SEQ ID NO:1.

Accordingly, the present invention extends to a commercial test kit having applications set forth above, comprising a predetermined amount of at least one detectably labeled immunochemically reactive component having affinity for a variant human mu opioid receptor;
 (b) other reagents; and
 (c) directions for use of the kit.

Antibodies of the present invention, and set forth above, have readily applications in a commercial test kit of the present invention.

In a further variation, the test kit may be prepared and used for the purposes stated above, which operates according to a predetermined protocol (e.g. "competitive," "sandwich," "double antibody," etc.), and comprises:
 (a) a labeled component which has been obtained by coupling the human mu opioid receptor of a bodily sample to a detectable label;
 (b) one or more additional immunochemical reagents of which at least one reagent is a ligand or an immobilized ligand, which ligand is selected from the group consisting of:
  (i) a ligand capable of binding with the labeled component (a);
  (ii) a ligand capable of binding with a binding partner of the labeled component (a);
  (iii) ligand capable of binding with at least one of the component(s) to be determined; and
  (iv) ligand capable of binding with at least one of the binding partners of at least one of the component(s) to be determined; and
 (c) directions for the performance of a protocol for the detection and/or determination of one or more components of an immunochemical reaction between the human mu opioid receptor gene of the present invention and a specific binding partner thereto.

The present invention may be better understood by reference to the following non-limiting Example, which is provided as exemplary of the invention. The following Example is presented in order to more fully illustrate the preferred embodiments of the invention. It should in no way be construed, however, as limiting the broad scope of the invention.

EXAMPLE

The mu opioid receptor is the major target for clinically important opioid alkaloids including morphine, methadone, fentanyl, and other opioid drugs (1,3), as well as for endogenous opioid peptides such β-endorphin, Met-enkephalin-Arg-Phe, and the recently identified endomorphins (5). Furthermore, it is the major molecular site of action for heroin (2,6). Rapid activation of the mu opioid receptor, such as occurs in the setting of drug abuse, results in a euphoric effect, thus conferring the reinforcing or rewarding effects of the drug, contributing to the development of addiction. Clinical observations have suggested that individuals have varied sensitivity to opioids, suggesting potential variability in the receptor protein and gene.

Molecular cloning of the mu opioid receptor (7–9) has made it possible to determine potential sequence polymorphism, as shown by a recent study (10). To further identify polymorphisms of the mu opioid receptor, a PCR-based strategy was used to amplify the coding regions of the mu opioid receptor gene, and to determine the DNA sequence of the amplified exons. Using this method DNA samples were sequenced from 450 subjects including both former heroin addicts in methadone maintenance treatment and individuals with no history of opiate or non-opiate drug dependence, as well as individuals with non-opiate drug abuse and dependence.

By sequencing PCR-amplified DNA from the study subjects, it was determined that the previously reported sequence for the human mu opioid receptor (8,9) was the most common allele found in the study population. Five new polymorphisms were also identified: T67C, T124A, C153T, G174A, or 187INS:GGC, of which C153T and G174A are silent, T67C results in Ser23Pro, T124A results in Ser42Thr, and 187INS:GGC results in the insertion of a Gly residue after Gly 63. For the purpose of this study, the term "most common" was used to denote the predominant mu opioid receptor allele and the corresponding receptor that was originally reported by cDNA cloning (8,9), and the term "variant" to denote the allelic genes/receptors containing polymorphic variations.

Figure 7B:
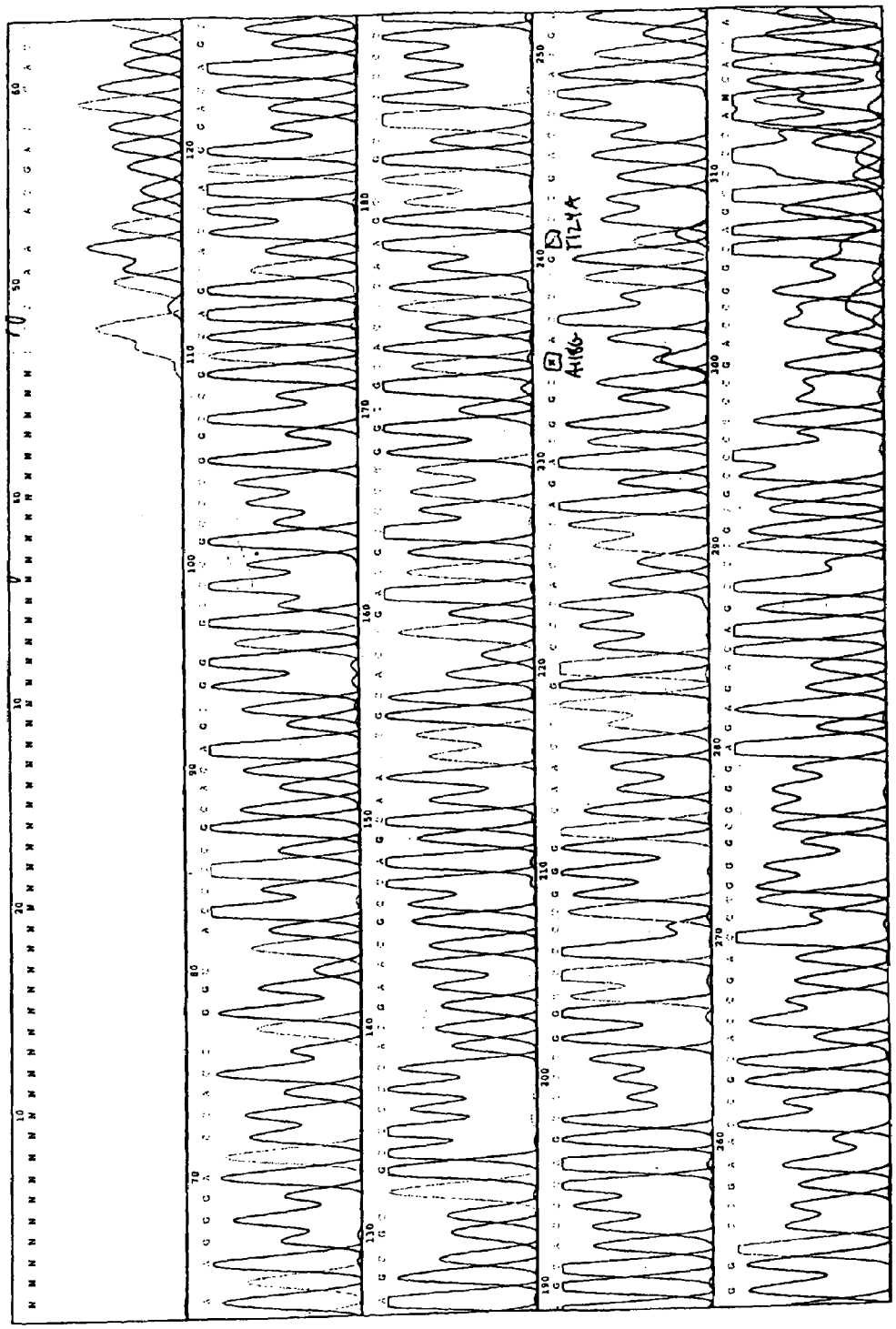

The results of sequencing of the PCR-amplified mu opioid receptor genes are shown in the following electropherograms. FIGS. 7A–7B show an electropherogram of the mu opioid receptor DNA from an individual heterozygous for both the A118G and the T124A single-nucleotide polymorphisms. FIG. 7A is the sequence of the (+) strand; FIG. 7B the (−) strand.

Figure 8A:
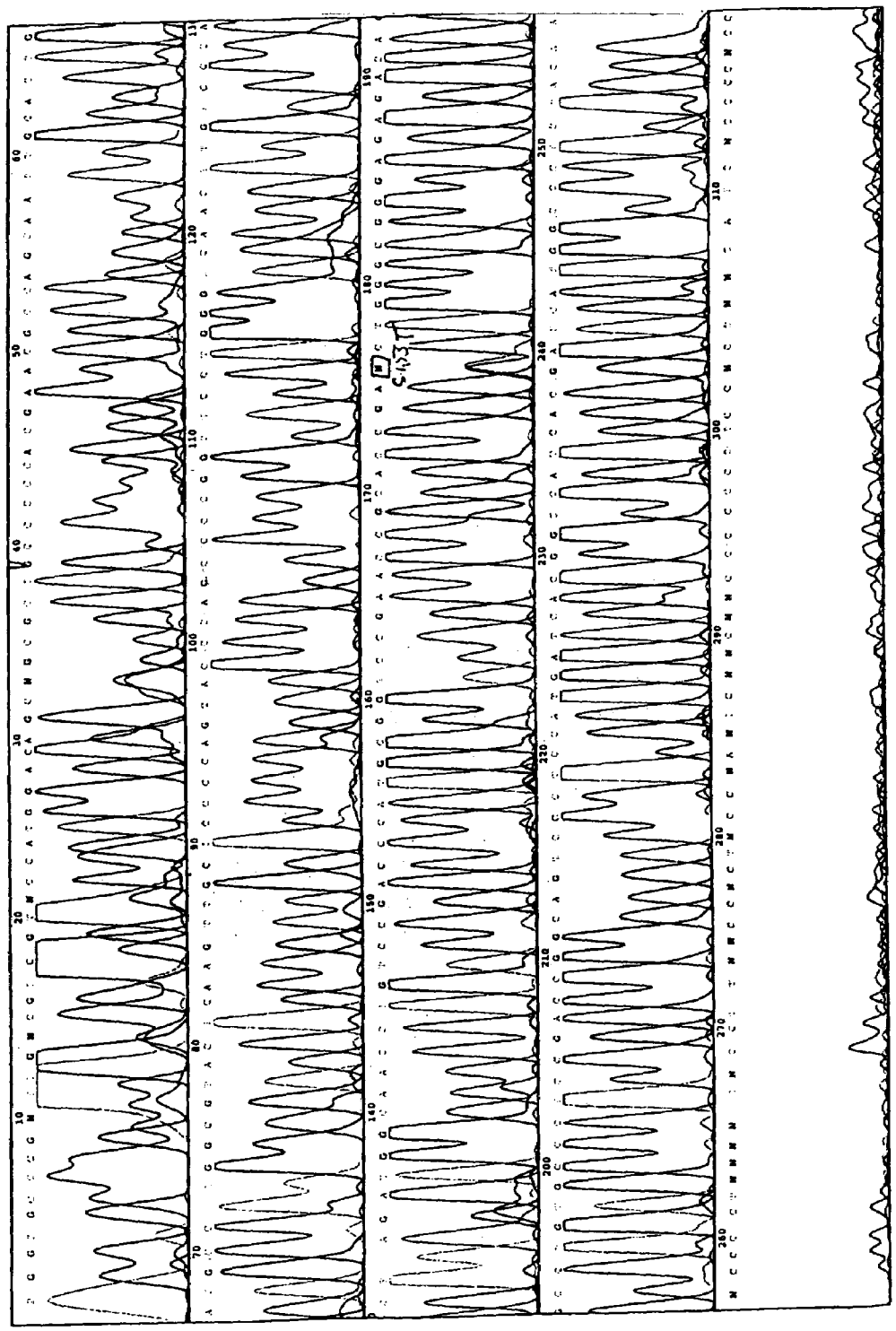
FIGS. 8A–8B: Electropherogram of the mu opioid receptor DNA from an individual heterozygous for the C153T single-nucleotide polymorphism.
Figure 8B:
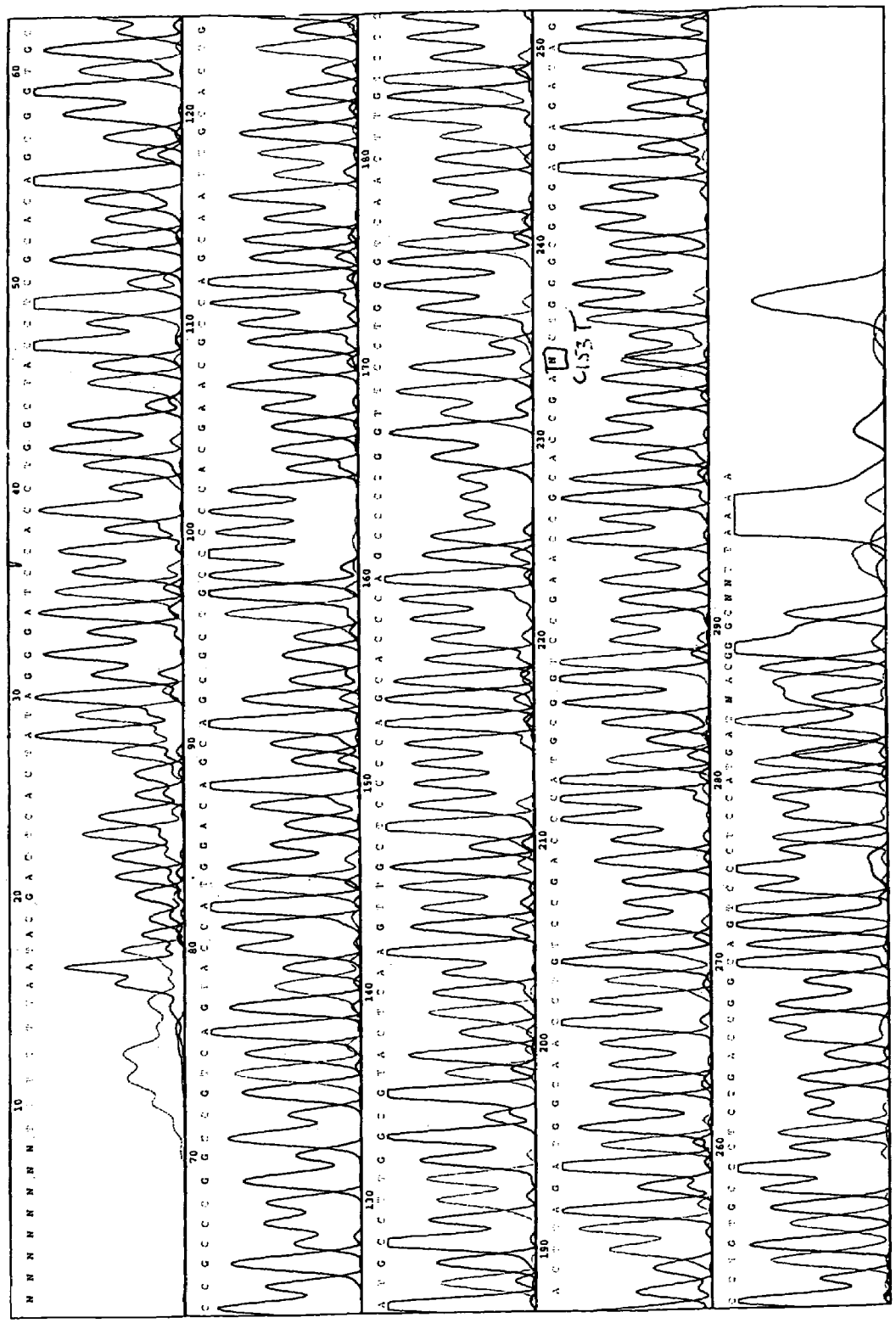
Figure 9A:
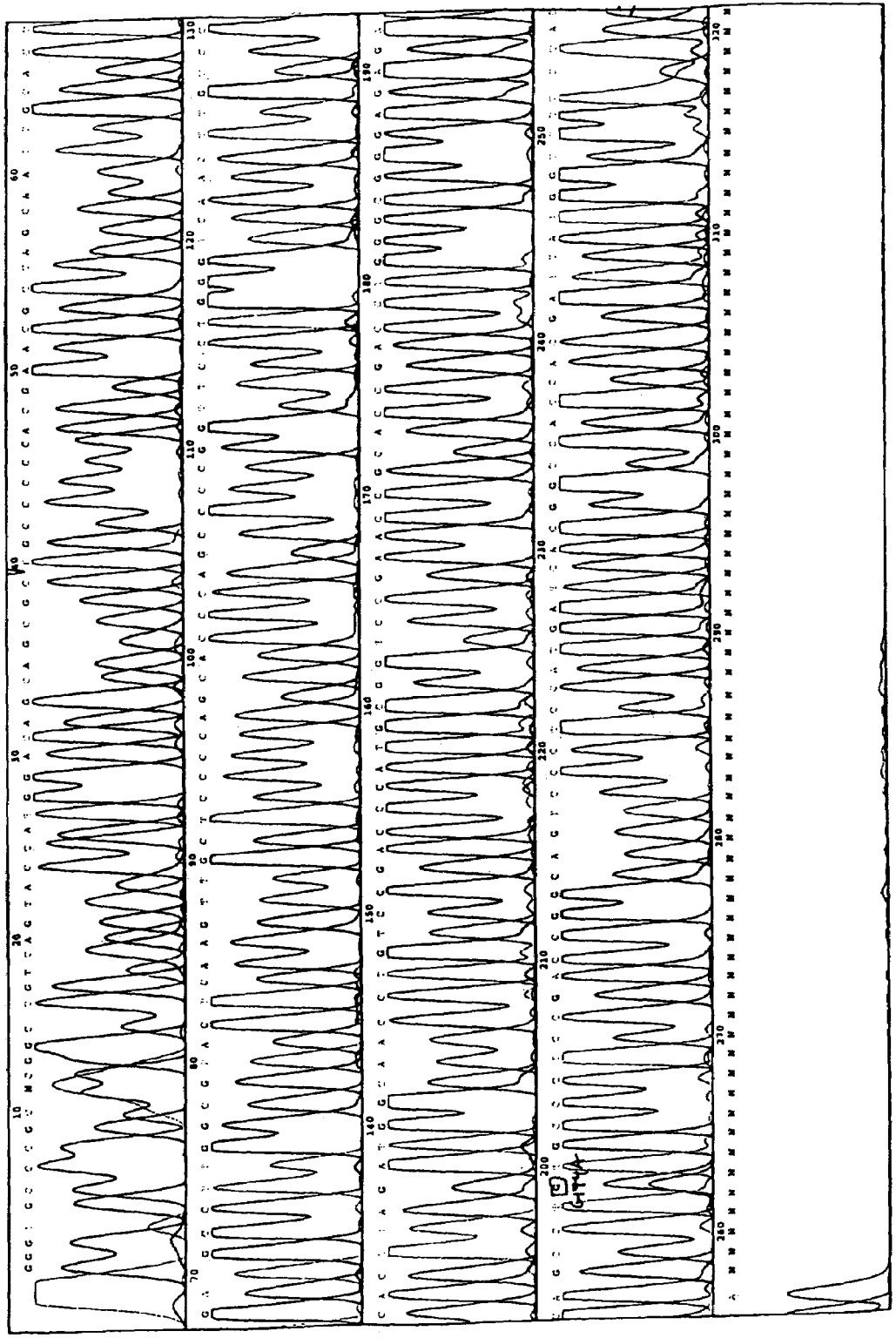
FIGS. 9A–9B: Electropherogram of the mu opioid receptor DNA from an individual heterozygous for the G174A single-nucleotide polymorphism.
Figure 9B:
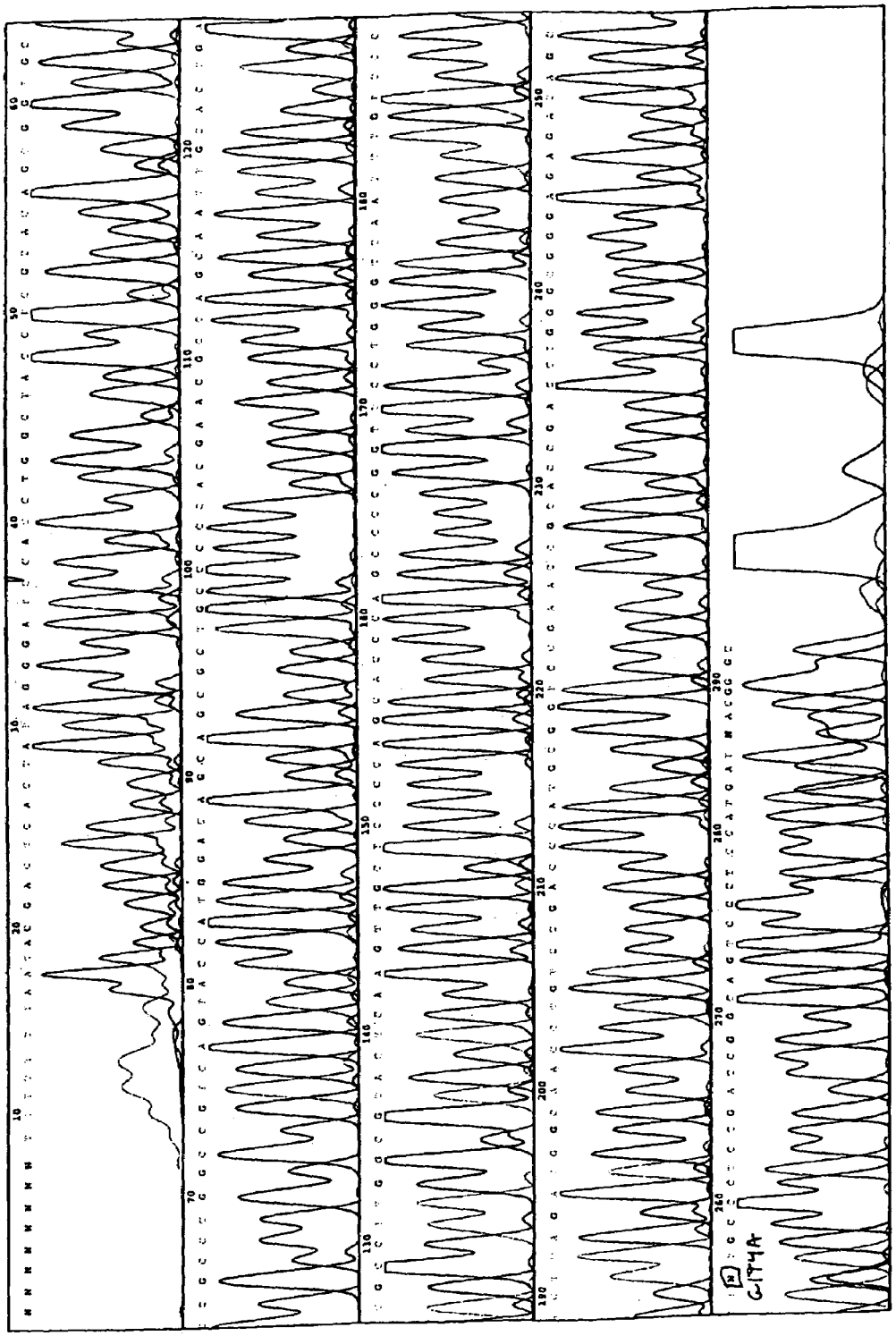
Figure 10A:
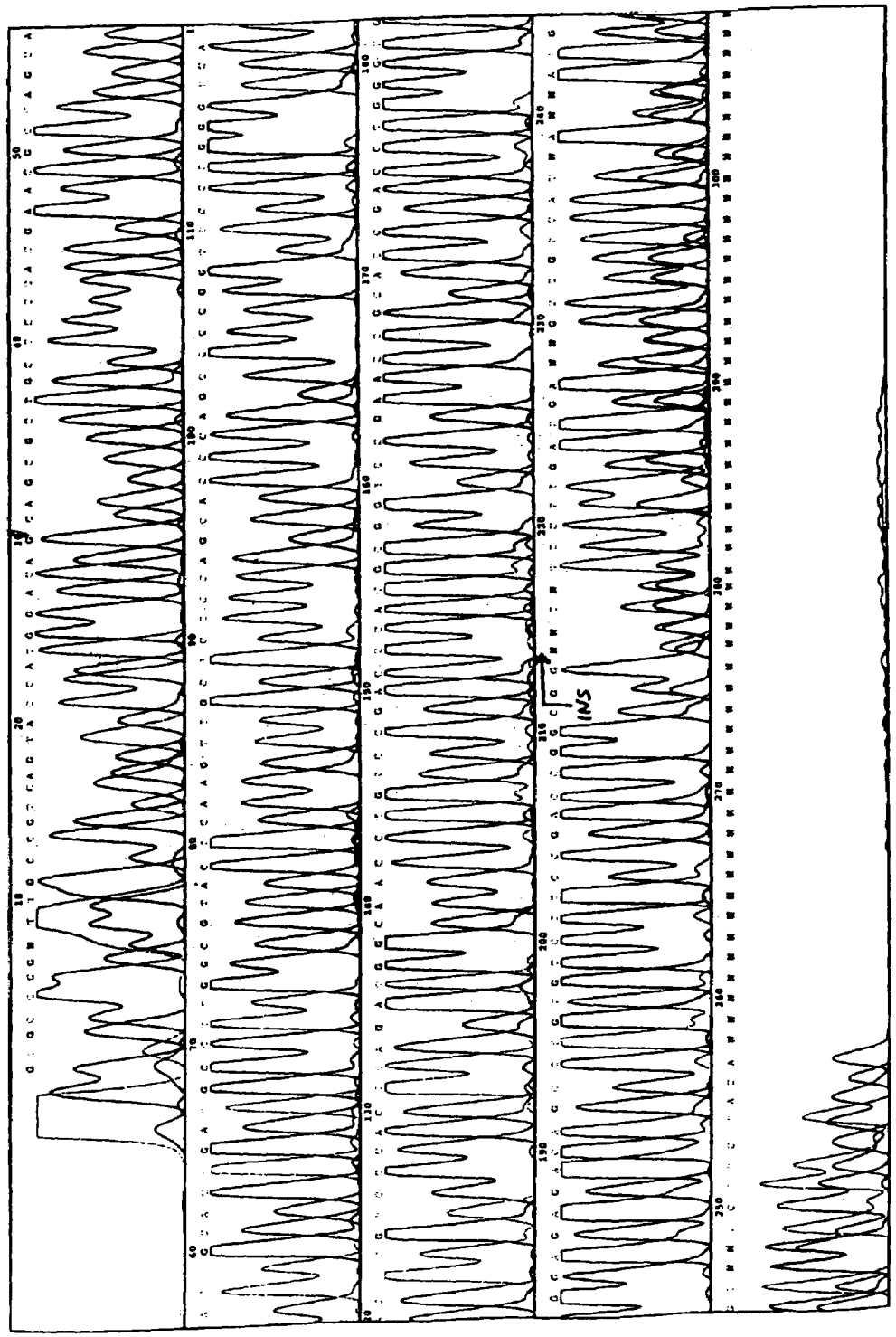
FIGS. 10A–10B: Electropherogram of the mu opioid receptor DNA from an individual heterozygous for the 187INS:GGC polymorphism, in which a GGC codon is inserted after position 187.
Figure 10B:
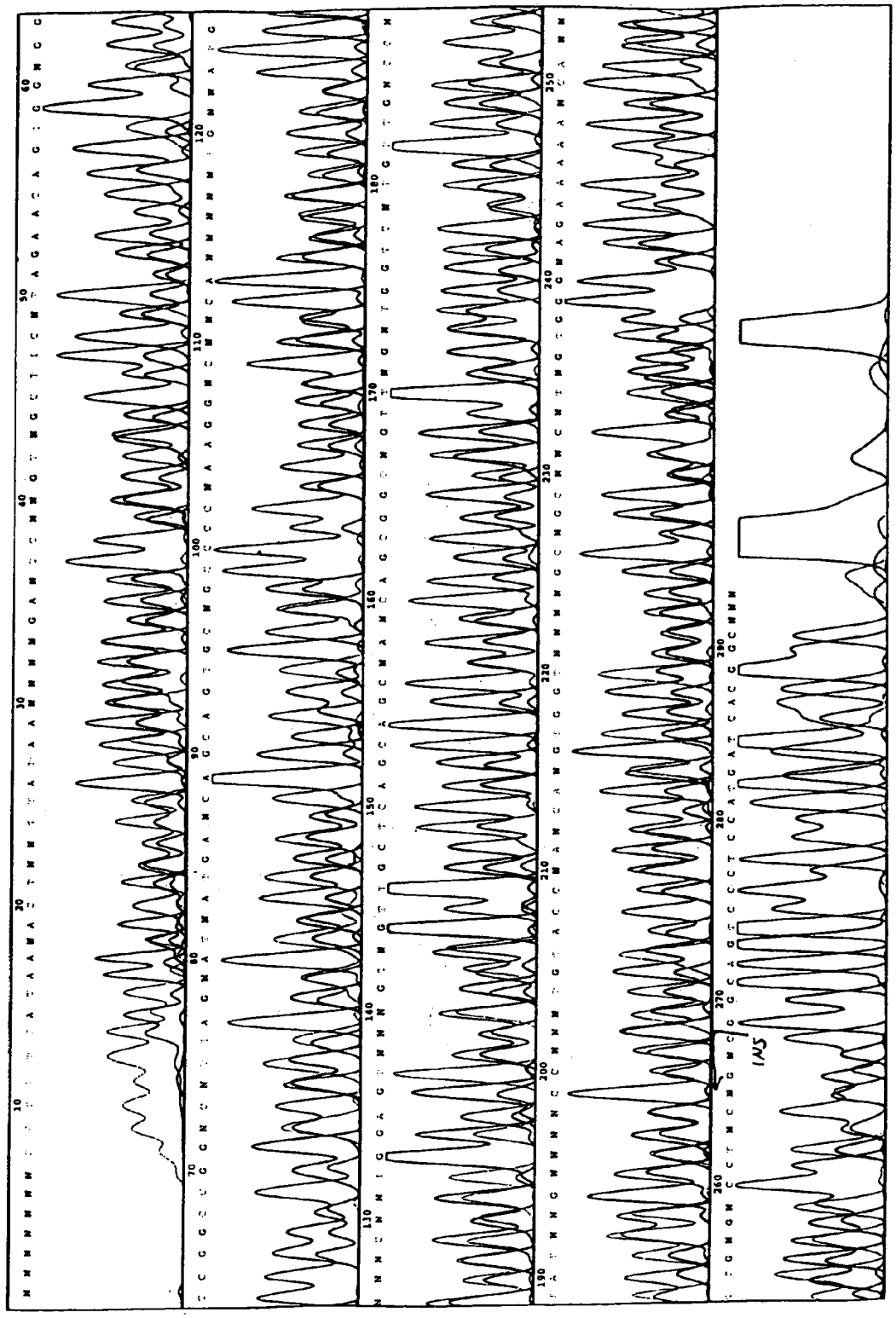
Figure 11A:
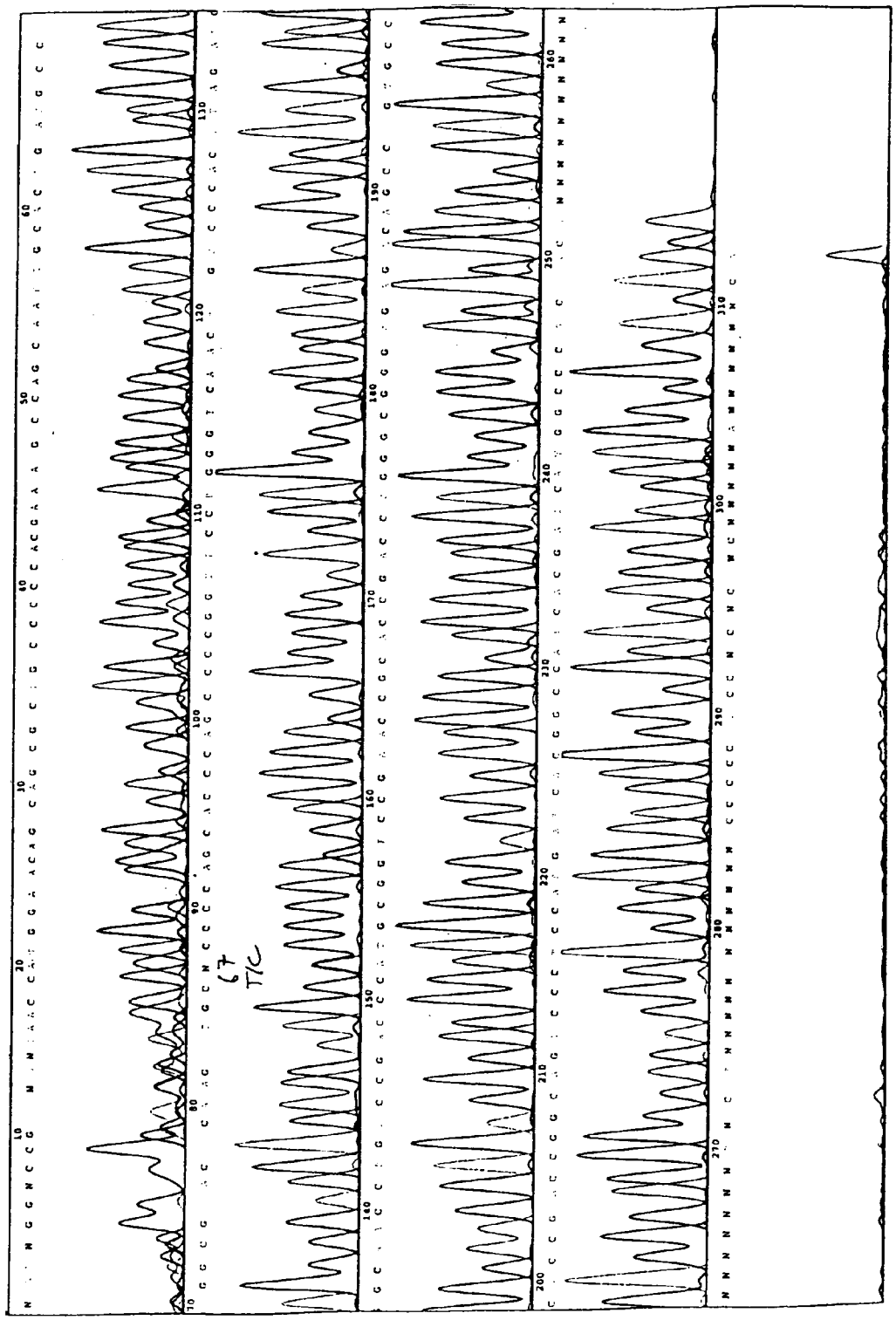
FIGS. 11A–11B: Electropherogram of the mu opioid receptor DNA from an individual heterozygous for the T67C (Ser23Pro) polymorphism.
Figure 11B:
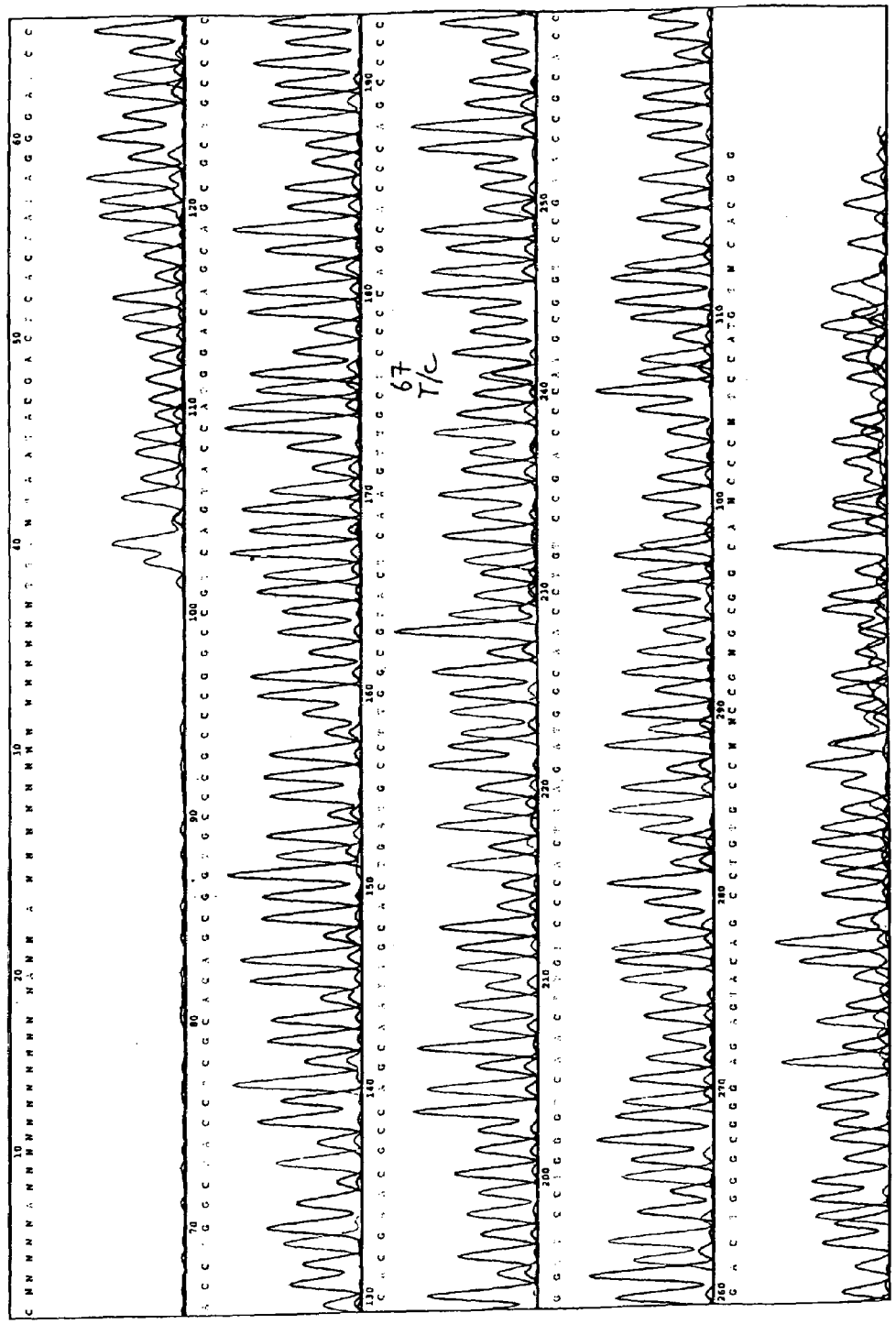

FIGS. 8A–8B show an electropherogram of the mu opioid receptor DNA from an individual heterozygous for the C153T single-nucleotide polymorphism. FIG. 8A is the sequence of the (+) strand; FIG. 9B the (−) strand. FIGS. 9A–9B show an electropherogram of the mu opioid receptor DNA from an individual heterozygous for the G174A single-nucleotide polymorphism. FIG. 9A is the sequence of the (+) strand; FIG. 9B the (−) strand. FIGS. 10A–10B show an electropherogram of the mu opioid receptor DNA from an individual heterozygous for the 187INS:GGC polymorphism, in which a GGC codon is inserted after position 187. FIG. 10A is the sequence of the (+) strand; FIG. 10B the (−) strand. FIGS. 11A–11B show an electropherogram of the mu opioid receptor DNA from an individual heterozygous for the T67C single-nucleotide polymorphism. FIG. 11A is the sequence of the (+) strand; FIG. 11B the (−) strand.

Based on these results, the sequence alterations in the four polymorphisms of the invention were obtained. FIGS. 1A–1B show the nucleic acid (1A) and protein (1B) sequence of the most common allele (i.e., wild type) of the mu opioid receptor (SEQ ID NO:1 and SEQ ID NO:2, respectively) (GENBANK accession number L25119). FIGS. 2A–2B show the DNA (2A, SEQ ID NO:3) and protein (2B, SEQ ID NO:4) sequence of the most common allele of the mu opioid receptor with the T67C polymorphism. As noted above, any of the other present or previously described mu opioid receptor polymorphisms may also be present; these and the following sequences merely show the wild-type DNA and protein sequences with the one polymorphism exemplified. FIG. 3A shows the DNA sequence (SEQ ID NO:5) of the most common allele of the mu opioid receptor with the T124A polymorphism. Likewise, FIG. 4 shows the DNA sequence (SEQ ID NO:6) of the most common allele of the mu opioid receptor with the C153T polymorphism, FIGS. 5A–5B show the DNA (5A, SEQ ID NO:7) and protein (5B, SEQ ID NO:8) sequence of the most common allele of the mu opioid receptor with the C174A polymorphism, and FIGS. 6A–6B show the DNA (6A, SEQ ID NO:7) and protein (6B, SEQ ID NO:8) sequence of the most common allele of the mu opioid receptor with the 187INS:GGC polymorphism.

By sequencing PCR-amplified DNA from the study subjects, it was determined that the previously reported sequence for the human mu opioid receptor (8,9) was the most common allele found in the study population. Five different polymorphisms were also identified. For the purpose of this study, the term "most common" or "prototypic" was used to denote the predominant mu opioid receptor allele and the corresponding receptor that was originally reported by cDNA cloning (8,9), and the term "variant" to denote the allelic genes/receptors containing polymorphic variations.

Study subjects and procedures. Addictive disease patients, specifically long-term heroin addicts currently in chronic methadone maintenance treatment, and normal control subjects with no history of any drug or alcohol abuse, and individuals with non-opiate drug abuse and dependence were extensively characterized with respect to drug abuse, the addictive diseases, psychological and psychiatric profiles, and medical and ethnic family backgrounds. Unrelated study subjects who were former heroin addicts were referred from methadone treatment clinics in the greater New York City area, primarily those associated with The Biology of Addictive Diseases Laboratory located at The Rockefeller University. These clinics are the Adolescent Development Program and Adult Clinic at the New York Hospital-Cornell Medical Center. Previously heroin-addicted patients admitted to the study conformed to the federally regulated criteria for admission to a methadone maintenance program, that is, one or more years of daily multiple-dose self-administration of heroin or other opiates with the development of tolerance, dependence, and drug-seeking behavior (38). Current or prior abuse of other drugs was not used as an exclusion criterion for this group as long as opioid abuse continued to be the primary diagnosis.

Unrelated healthy volunteer subjects were recruited primarily through posting of notices and newspaper advertisements or referral by physicians or staff at the Rockefeller University Hospital. Individuals with continuing drug or alcohol abuse or prior extended periods of regular abuse were also studied.

Both addictive disease patients and normal volunteers admitted to the study were assessed by a psychiatrist or research nurse with several psychiatric and psychological instruments as well as the Addiction Severity Index (39). Study subjects were also administered a detailed personal and medical and special addictive disease questionnaire as well as a family history medical and addictive disease questionnaire designed to provide information regarding substance abuse and major mental illness of first and second degree relatives. Study subjects provided detailed information regarding family origin and ethnic background, including country or geographic area of birth. This information was obtained for both the study subjects themselves and their immediate ancestors (parents, grandparents and great-grandparents), to the extent that the information was known by the study subjects. Study subjects were classified into five groups: African-American, Caucasian, Hispanic (Caribbean and Central or South American origin), Native North American, and Other. The detailed ancestral information collected by the family origin questionnaire allowed classification of study subjects into defined categories. Following psychiatric and behavioral assessment and informed consent and family history acquisition, venipuncture on the study subject was performed, and a blood specimen was taken. Blood samples were processed for DNA extraction and EBV transformation to create stable cell lines that were stored for future studies. All blood samples were coded; the psychiatrists and nurses who performed psychiatric and psychological assessments were blind to the genotypes of the study subjects, and the identity and categorization of the study subjects was unknown to the laboratory research personnel.

Exon amplification and sequencing. Sequences for the non-coding regions of the human mu opioid receptor gene were used to design PCR primers for the sequencing of the first exon. Exon 1 forward primer sequences were based on the 5'-untranslated region of the receptor (9). Only one reverse primer was used for exon 1. The PCR reactions were performed with 50–100 ng of genomic DNA. DNA polymorphisms were confirmed by both manual and automated sequencing on both strands, forward and reverse.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

1. Chen, Y., Mestek, A., Liu, J., Hurley, J. A. & Yu, L. Molecular cloning and functional expression of a mu-opioid receptor from rat brain. *Mol. Pharmacol.* 44, 8–12 (1996).
2. Wang, J. B., Johnson, P. S., Persico, A. M., Hawkins, A. L., Griffin, C. A. & Uhl, G. R. Human mu opioid receptor: cDNA and genomic clones, pharmacologic characterization and chromosomal assignment. *FEBS Lett.* 338, 217–222 (1994).
3. Berrettini, W. H., Hoehe, M. R., Ferrada, T. N. & Gottheil, E. (1997) *Addiction Biol.* 2, 303–308.
4. Kreek, M. J., Wardlaw, S. L., Hartman, N., Raghunath, J., Friedman, J., Schneider, B. & Frantz, A. G. (1983) *Life Sci.* 33 Suppl 1, 409–411.
5. Kreek, M. J., Ragunath, J., Plevy, S., Hamer, D., Schneider, B. & Hartman, N. (1984) *Neuropeptides* 5, 277–278.
6. Ragavan, V. V., Wardlaw, S. L., Kreek, M. J. & Frantz, A. G. (1983 *Neuroendocrinology* 37, 266–268.
7. Berrettini, W. H., Hoehe, M. R., Ferraro, T. N., DeMaria, P. A., and Gottheil, E., *Addiction Biology* 2:303–308 (1997).
8. McDonald et al., Effect of morphine and nalorphine on plasma hydrocortisone levels in man. *J. Pharmacol. Exp. Ther.* 125:241247 (1959).
9. Kreek, Medical safety and side effects of methadone in tolerant individuals. *JAMA* 223:665–668 (1973).
10. Kreek, 1973; Kreek et al., Circadian rhythms and levels of beta-endorphin, ACTH, and cortisol during chronic methadone maintenance treatment in humans. *Life Sci.* 33:409–411 (1983).
11 Kreek et al., Prolonged (24 hour) infusion of the opioid antagonist naloxone does not significantly alter plasma levels of cortisol and ACTH in humans. *Proceedings of the 7th International Congress on Endocrinology*, Elsevier Science, p. 1170, 1984
12. Taylor et al., Beta-endorphin suppresses adrenocroticotropin and cortisol levels in normal human subjects. *J. Clin. Endocrinol. Metab.* 57:592–596 (1983)
13. Reeck et al., 1987, *Cell* 50:667

What is claimed is:

1. An isolated nucleic acid, wherein said nucleic acid comprises the DNA sequence of SEQ ID NO:1, except that one or more of the following variations are present:
   a) the "T" at position 279 of SEQ ID NO: 1 is replaced with a "C";
   b) the "T" at position 336 of SEQ ID NO: 1 is replaced with an "A";
   c) the "C" at position 365 of SEQ ID NO: 1 is replaced with a "T";
   d) the "G" at position 386 of SEQ ID NO: 1 is replaced with an "A";
   e) the nucleotides "GGC" are inserted following position 401 of SEQ ID NO: 1.

2. The isolated nucleic acid of claim 1, detectably labeled.

3. An isolated nucleic acid encoding a human mu opioid receptor variant, wherein said variant comprises the amino acid sequence of SEQ ID NO: 2, except that one or more of the following variations is present in the encoded sequence:
   a) the serine at position 23 of SEQ ID NO: 2 is replaced with a proline;
   b) the serine at position 42 of SEQ ID NO: 2 is replaced with a threonine;
   c) the addition of a glycine residue following the glycine at position 63.

4. A cloning or expression vector comprising an isolated nucleic acid encoding a human mu opioid receptor variant and an origin of replication, wherein said nucleic acid comprises the DNA of claim 1.

5. An expression vector comprising an isolated nucleic acid encoding a human mu opioid receptor variant comprising the DNA sequence of claim 1.

6. A unicellular host transformed or transfected with an expression vector comprising an isolated nucleic acid encoding a human mu opioid receptor variant operatively associated with a promoter, wherein said nucleic acid comprises the DNA sequence of claim 1.

7. An isolated nucleic acid encoding a human mu opioid receptor variant, wherein said nucleic acid comprises the DNA sequence of claim 1 having at least two variations in SEQ ID NO:1, wherein at least two of the following variations are present:
   a) the "T" at position 279 of SEQ ID NO: 1 is replaced with a "C";
   b) the "T" at position 336 of SEQ ID NO: 1 is replaced with an "A";
   c) the "C" at position 365 of SEQ ID NO: 1 is replaced with a "T";
   d) the "G" at position 386 of SEQ ID NO: 1 is replaced with an "A";
   e) the nucleotides "GGC" are inserted following position 401 of SEQ ID NO: 1.

8. The isolated nucleic acid of claim 7 detectably labeled.

9. An isolated nucleic acid which encodes a variant human mu opioid receptor, wherein said variant comprises the amino acid sequence of SEQ ID NO: 2, except that two or more of the following variations is present in the encoded sequence:
   a) the serine at position 23 of SEQ ID NO: 2 is replaced with a proline;
   b) the serine at position 42 of SEQ ID NO: 2 is replaced with a threonine;
   c) the addition of a glycine residue following the glycine at position 63.

10. A cloning or expression vector comprising an isolated nucleic acid encoding a human mu opioid receptor variant and an origin of replication, wherein said nucleic acid comprises a DNA sequence of claim 1 having at least two variations in SEQ ID NO: 1 wherein the two variations are selected from the following variations:

a) the "T" at position 279 of SEQ ID NO: 1 is replaced with a "C";

b) the "T" at position 336 of SEQ ID NO: 1 is replaced with an "A";

c) the "C" at position 365 of SEQ ID NO: 1 is replaced with a "T";

d) the "G" at position 386 of SEQ ID NO: 1 is replaced with an "A";

e) the nucleotides "GGC" are inserted following position 401 of SEQ ID NO: 1.

11. A unicellular host transformed with an expression vector of claim 10.

* * * * *